(12) United States Patent
Chen et al.

(10) Patent No.: US 9,184,315 B2
(45) Date of Patent: Nov. 10, 2015

(54) PHOTOELECTRIC MATERIALS AND PREPARATION THEREOF

(75) Inventors: Yongsheng Chen, Tianjin (CN); Xiangjian Wan, Tianjin (CN); Yongsheng Liu, Tianjin (CN); Zhi Li, Tianjin (CN); Jiaoyan Zhou, Tianjin (CN); Fei Wang, Tianjin (CN); Guangrui He, Tianjin (CN); Guankui Long, Tianjin (CN)

(73) Assignee: NANKAI UNIVERSITY, Tianjin (CN)

( * ) Notice: Subject to any disclaimer, the term of this patent is extended or adjusted under 35 U.S.C. 154(b) by 0 days.

(21) Appl. No.: 14/003,734

(22) PCT Filed: Mar. 7, 2012

(86) PCT No.: PCT/CN2012/072060
§ 371 (c)(1),
(2), (4) Date: Nov. 15, 2013

(87) PCT Pub. No.: WO2012/119551
PCT Pub. Date: Sep. 13, 2012

(65) Prior Publication Data
US 2014/0142308 A1 May 22, 2014

(30) Foreign Application Priority Data

Mar. 8, 2011 (CN) .......................... 2011 1 0058165
Aug. 15, 2011 (CN) .......................... 2011 1 0235857

(51) Int. Cl.
| | |
|---|---|
| C07D 409/14 | (2006.01) |
| C07D 417/14 | (2006.01) |
| C07D 495/04 | (2006.01) |
| H01L 31/0216 | (2014.01) |
| C07D 333/22 | (2006.01) |
| C07D 333/24 | (2006.01) |
| C08G 61/12 | (2006.01) |
| H01B 1/12 | (2006.01) |
| H01L 51/00 | (2006.01) |
| H01L 51/42 | (2006.01) |

(52) U.S. Cl.
CPC ........ *H01L 31/02167* (2013.01); *C07D 333/22* (2013.01); *C07D 333/24* (2013.01); *C07D 409/14* (2013.01); *C07D 417/14* (2013.01); *C07D 495/04* (2013.01); *C08G 61/123* (2013.01); *C08G 61/126* (2013.01); *H01B 1/127* (2013.01); *H01L 51/0064* (2013.01); *H01L 51/0068* (2013.01); *H01L 51/0071* (2013.01); *H01L 51/0074* (2013.01); *H01L 51/0094* (2013.01); *C08G 2261/1642* (2013.01); *C08G 2261/1644* (2013.01); *C08G 2261/226* (2013.01); *C08G 2261/3223* (2013.01); *C08G 2261/3243* (2013.01); *C08G 2261/3246* (2013.01); *C08G 2261/344* (2013.01); *H01L 51/0036* (2013.01); *H01L 51/0037* (2013.01); *H01L 51/0053* (2013.01); *H01L 51/4253* (2013.01); *H01L 2251/308* (2013.01); *H01L 2251/53* (2013.01); *Y02E 10/549* (2013.01)

(58) Field of Classification Search
CPC ... C07D 409/14; C07D 417/14; C07D 495/04
USPC ................................................ 548/126, 453
See application file for complete search history.

(56) References Cited

U.S. PATENT DOCUMENTS

| | | | |
|---|---|---|---|
| 7,183,418 B2 * | 2/2007 | Heeney et al. .................. 549/50 |
| 2011/0004004 A1 | 1/2011 | Hao et al. | |
| 2011/0023964 A1 | 2/2011 | Kitazawa et al. | |
| 2011/0121273 A1 | 5/2011 | Jo et al. | |

FOREIGN PATENT DOCUMENTS

| | | | | |
|---|---|---|---|---|
| CA | 2 625 306 | * | 3/2008 | ........... C07D 333/28 |
| JP | 2008277489 | * | 11/2008 | ........... C07D 417/14 |
| WO | WO 2008/044585 | * | 10/2007 | .............. C08L 65/00 |
| WO | WO 2009/047104 | | 4/2009 | |
| WO | WO 2009/125647 | | 10/2009 | |
| WO | WO 2009/139339 | | 11/2009 | |

OTHER PUBLICATIONS

Deng, et al., Triphenylamine-containing linear D-A-D molecules with benzothiadiazole as acceptor unit for bulk-heterojunction organic solar cells, Organic Electronics, 12(4), 614-622 (2011).*
Deng, et al., Synthesis and photovoltaic properties of functional dendritic oligothiophenes, Journal of Polymer Science, Part A: Polymer Chemistry 49(8), 1865-1873 (2011).*
Steinberger, et al., A-D-A-D-A-type oligothiophenes for vacuum-deposited organic solar cells, Organic Letters (2011), 13(1), 90-93.*
Shiro, et al., Electronic Properties and Photovoltaic Performances of a Series of Oligothiophene Copolymers Incorporating Both Thieno[3,2-b]thiophene and 2,1,3-Benzothiadiazole Moieties, Macromolecular Rapid Communications 31(7), 651-656 (2010).*
Sakai, et al., Syntheses, Structures, Spectroscopic Properties, and -Dimeric Interactions of [n.n]Quinquethiophenophanes, J. of the American Chem. Soc., 127(22), 8082-8089 (2005).*
Li, et al., Synthesis of a benzothiadiazole/thiophene-based oligomer for bulk heterojunction photovoltaic cells, Synthetic Metals (2009), 159(3-4), 201-208.*
Cai et al., "N- and P-Channel Transport Behavior in Thin Film Transistors Based on Tricyanovinyl-Capped Oligothiophenes" J. Phys. Chem, B, vol. 110, No. 30, 2006, pp. 14590-14597.

* cited by examiner

Primary Examiner — Erich A Leeser
(74) Attorney, Agent, or Firm — Knobbe, Martens, Olson & Bear LLP

(57) ABSTRACT

Receptor type oligothiopene compounds, methods of preparing the compounds, and use of the compounds in photoelectric materials.

20 Claims, 10 Drawing Sheets

PHOTOELECTRIC MATERIALS AND PREPARATION THEREOF

This application is the U.S. National Phase under 35 U.S.C. §371 of International Application No. PCT/CN2012/072060, filed Mar. 7, 2012, designating the U.S., and published in Chinese as WO 2012/119551 on Sep. 13, 2012, which claims priority to Chinese Patent Application No. 201110058165.0 filed Mar. 8, 2011; and Chinese Patent Application No. 201110235857.8, filed Aug. 15, 2011, the entire contents of which are incorporated herein by reference.

FIELD

The present application relates to the field of material chemistry. In particular, the present application relates to the field of photoelectric materials.

BACKGROUND

Solar energy is an inexhaustible, clean, non-polluting and renewable energy for human beings. Comparing with inorganic solar cells, organic solar cells possess advantages such as light weight, low cost, solution processing, high mechanical flexibility, and capability of manufacturing large scale flexible devices.

SUMMARY

In an aspect, the present application relates to a donor-receptor type oligothiophene compound represented by the following general formula:

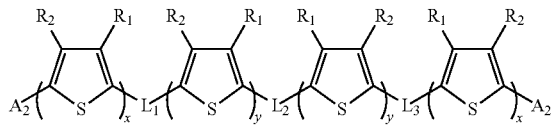

wherein x is an integer of 0 to 50, y is an integer of 1 to 50; $R_1$ and $R_2$ are each independently selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, wherein $R_1$ and $R_2$ may be identical or different, but $R_1$ and $R_2$ are not H simultaneously;

$L_1$, $L_2$ and $L_3$ are each independently selected from the group consisting of a bridged conjugated electron donor unit and a bridged conjugated electron receptor unit; and $A_2$ is a terminal receptor unit.

In another aspect, the present application relates to a donor-receptor type oligothiophene compound of general formulae (1) to (6):

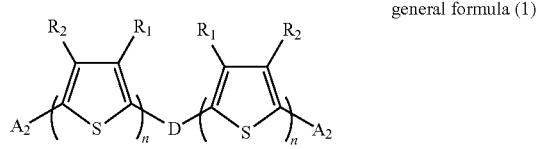
general formula (1)

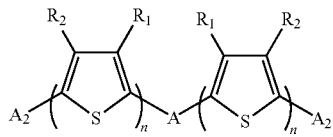
general formula (2)

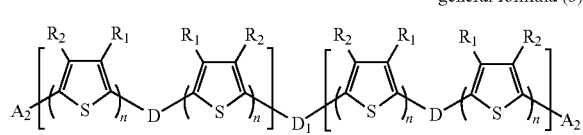
general formula (3)

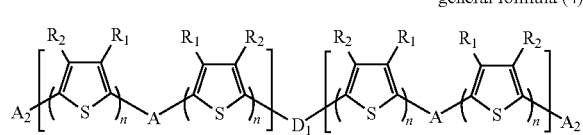
general formula (4)

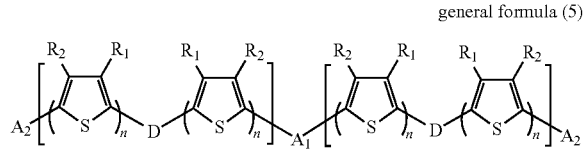
general formula (5)

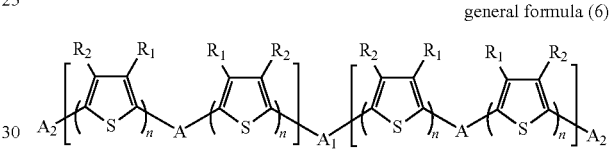
general formula (6)

wherein n is an integer of 1 to 50;

$R_1$ and $R_2$ are each independently selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, wherein $R_1$ and $R_2$ may be identical or different, but $R_1$ and $R_2$ are not H simultaneously;

D and $D_1$ are each independently a bridged conjugated electron donor unit;

A and $A_1$ are each independently a bridged conjugated electron receptor unit; and $A_2$ is a terminal receptor unit.

In yet another aspect, the present application relates to a process for preparing a donor-receptor type oligothiophene compound comprising a receptor terminal of general formulae (1) to (6), comprising carrying out a Knoevenagel condensation reaction of a donor bridged oligothiophene comprising a receptor terminal with a receptor terminal monomer through a bisaldehyde group donor bridged oligothiophene in the presence of a solvent and a catalyst to obtain the compound.

In still another aspect, the present application relates to a process for preparing a donor-receptor type oligothiophene compound of general formulae (1) to (6), comprising carrying out a Knoevenagel condensation reaction of a donor bridged oligothiophene comprising a small molecule dye terminal with an organic small molecule dye monomer through a bisaldehyde group donor bridged oligothiophene in the presence of a solvent and a catalyst to obtain the compound.

In yet another aspect, the present application relates to use of a donor-receptor type oligothiophene compound comprising a receptor terminal of general formulae (1) to (6) in the manufacture of a field effect transistor.

In still another aspect, the present application relates to use of a donor-receptor type oligothiophene compound comprising a receptor terminal of general formulae (1) to (6) in the manufacture of a photovoltaic device.

In yet another aspect, the present application relates to a triode device comprising an active layer having a donor-receptor type oligothiophene compound comprising a receptor terminal of general formulae (1) to (6).

In still another aspect, the present application relates to a photovoltaic device comprising an active layer having a donor-receptor type oligothiophene compound comprising a receptor terminal of general formulae (1) to (6).

In yet another aspect, the present application relates to a process for manufacturing a field effect transistor, comprising providing a donor-receptor type oligothiophene compound comprising a receptor terminal of general formulae (1) to (6).

In still another aspect, the present application relates to a process for manufacturing a photovoltaic device, comprising providing a donor-receptor type oligothiophene compound comprising a receptor terminal of general formulae (1) to (6).

In other aspects, the present application relates to a compound selected from the group consisting of:

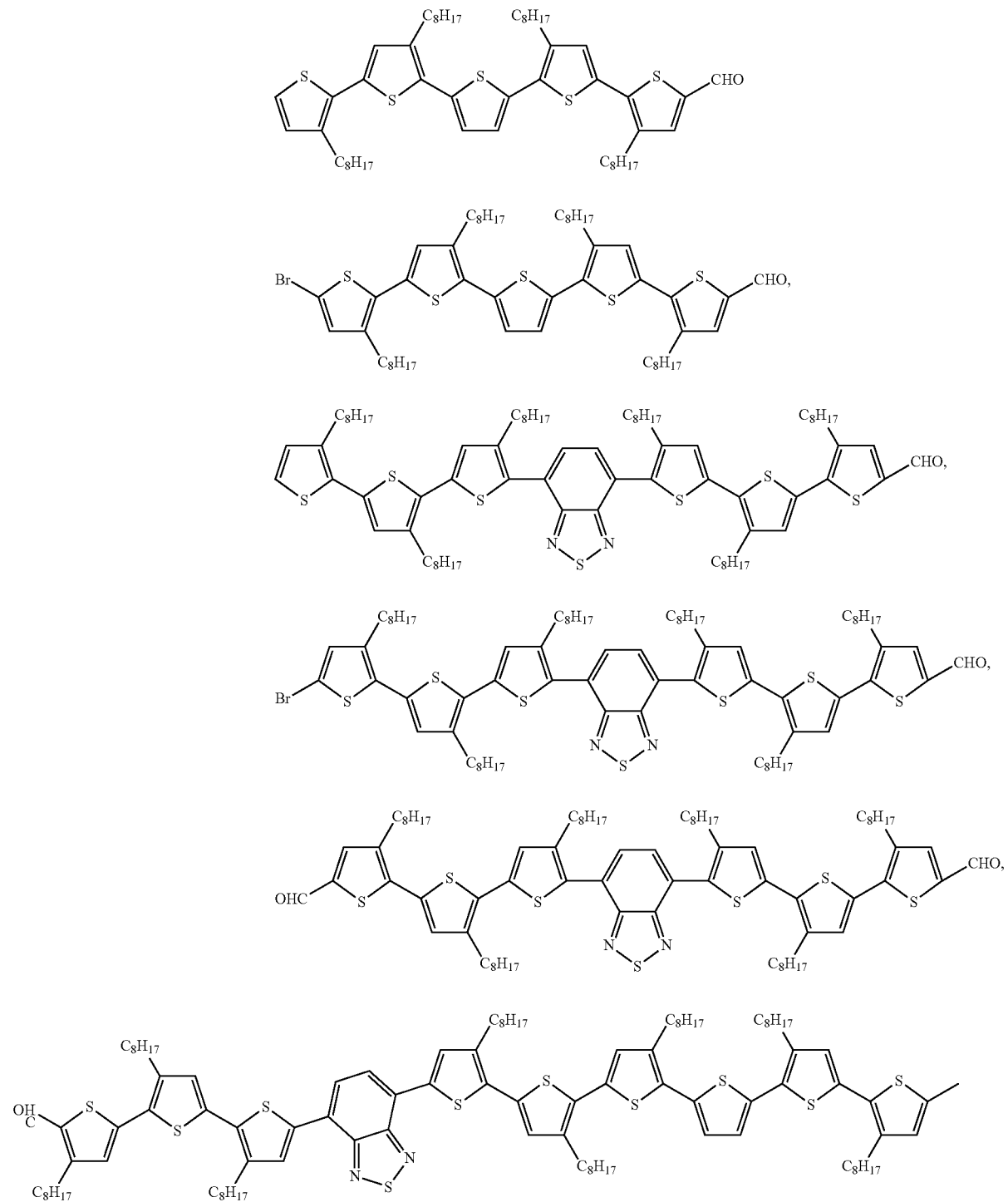

-continued
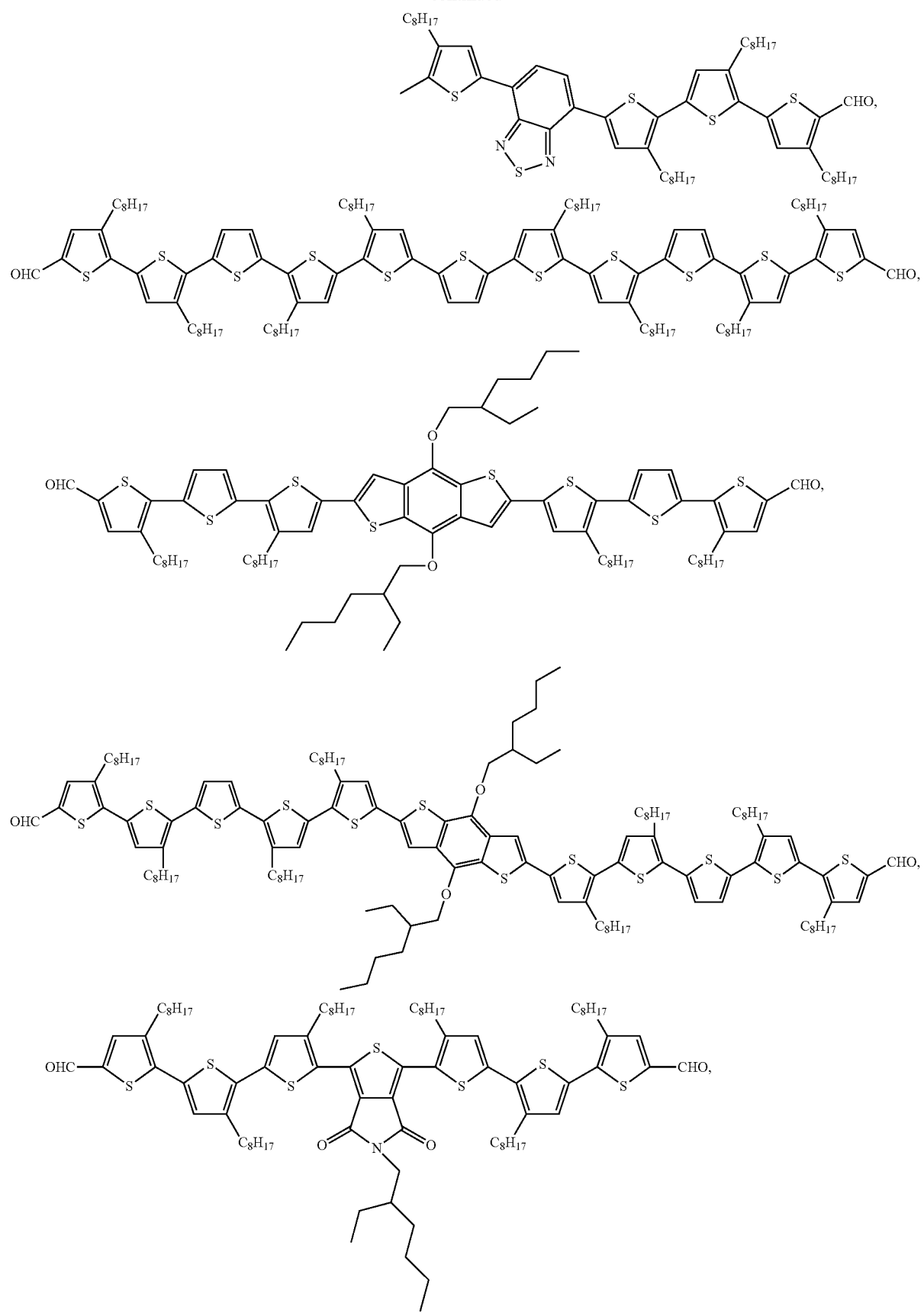

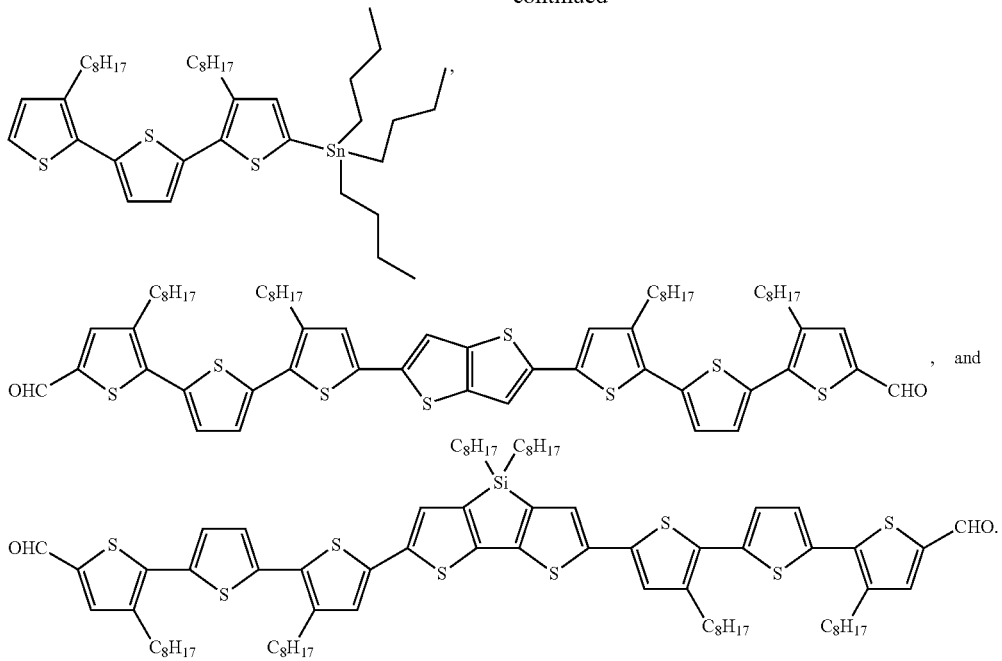

DETAIL DESCRIPTION

Figure 1:
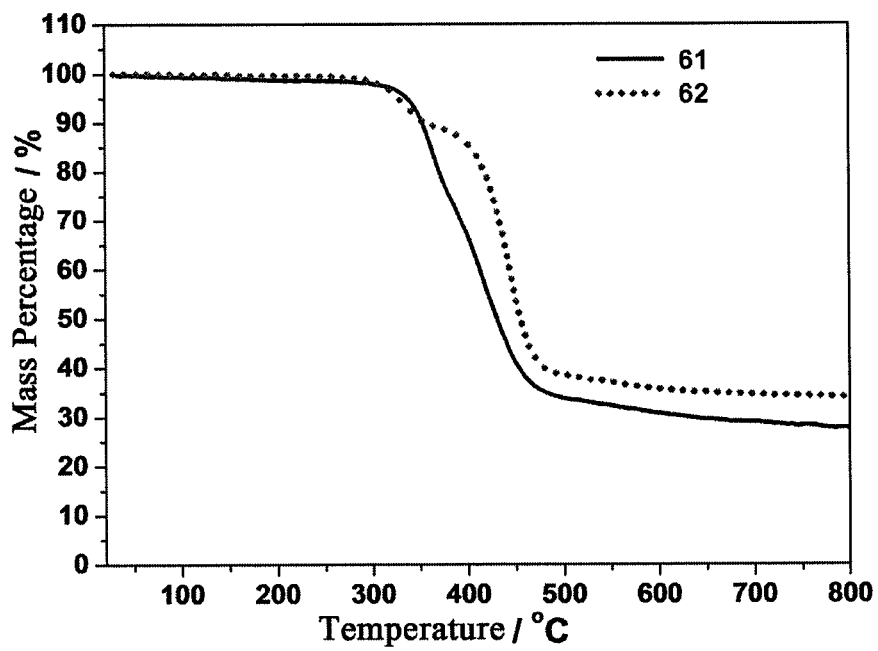
FIG. 1 is thermal gravimetric analysis (TGA) curves of the compounds in Examples 2 and 3 in the present application.
Figure 2:
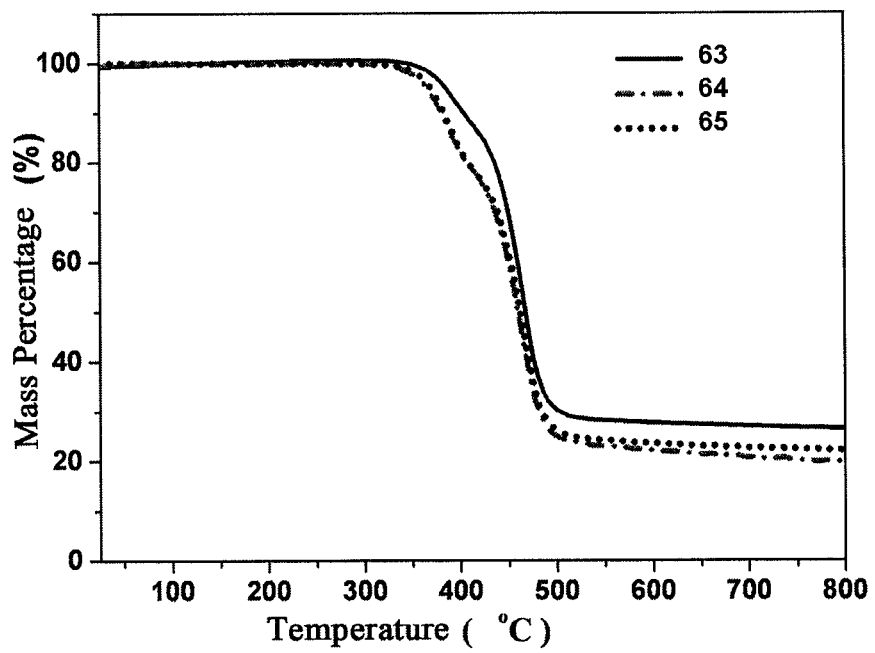
FIG. 2 is thermal gravimetric analysis (TGA) curves of the compounds in Examples 4, 5 and 6 in the present application.

In the following description, certain specific details are included to provide a thorough understanding of various disclosed embodiments. One skilled in the relevant art, however, will recognize that the embodiments may be practiced without one or more these specific details, or with other methods, components, materials, etc.

Unless the context required otherwise, throughout the specification and claims which follows, the terms "comprise" and "include" are to be construed in an open, inclusive sense, which shall be construed as "include, but not limited to".

Reference throughout this specification to "one embodiment", or "an embodiment", or "in another embodiment", or "in some embodiments" means that a particular referent feature, structure or characteristic described in connection with the embodiment is included in at least one embodiment. Therefore, the appearance of the phrases "in one embodiment" or "in the embodiment" or "in another embodiment" or "in some embodiments" in various places throughout this specification are not necessarily all referring to the same embodiment. Moreover, the particular features, structures or characteristics may be combined in any suitable manner in one or more embodiments.

DEFINITION

Certain chemical groups named herein are preceded by a shorthand notion indicating the total number of carbon atoms that are to be found in the indicated chemical groups. For example, $C_7$-$C_{12}$ alkyl describes an alkyl, as defined below, having a total of 7 to 12 carbon atoms, and $C_4$-$C_{12}$ cycloalkylalkyl describes a cycloalkylalkyl, as defined below, having a total 4 to 12 carbon atoms. The total number of carbon atoms in the shorthand notation does not include carbons that may exist in the substituents of the groups described.

Accordingly, as used in the specification and appended claims, unless specified to the contrary, the following terms have the meanings indicated:

The term "alkyl" as used herein refers to a linear- or branched-chain hydrocarbon chain group having 1 to 30 carbon atoms, especially 1 to 12 or 1 to 8 carbon atoms, which consists of carbon atoms and hydrogen atoms and connects with the rest of the molecular via a single bond, such as methyl, ethyl, n-propyl, 1-methylethyl (isopropyl), n-butyl, n-pentyl, 1,1-dimethylethyl (t-butyl), octyl groups etc.

In some embodiments, alkyl is $C_1$-$C_{30}$ alkyl. In some embodiments, alkyl is $C_1$-$C_{12}$ alkyl. In some embodiments, alkyl is $C_1$-$C_8$ alkyl.

The alkyl group may be optionally substituted, i.e. substituted or unsubstituted. Where substituted, the substituted group(s) is(are) individually and independently selected from the group consisting of cycloalkyl, aryl, heteroaryl, hetero alicyclic, hydroxy, hydro carboxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, —NR'R" or amino including mono- and bi-substituted amino group, and the protected derivatives thereof.

In some embodiments, $C_1$-$C_{30}$ alkyl is substituted with a halogen.

The term "cycloalkyl" as used herein refers to a saturated stable non-aromatic monocyclic or bicyclic hydrocarbyl group having 3 to 15 carbon atoms, especially 3 to 30 carbon atoms, which only consists of carbon and hydrogen atoms and connects with the rest of the molecule via a single bond, such as cyclopropyl, cyclobutyl, cyclopentyl, cyclohexyl, cyclodecyl etc.

In some embodiments, cycloalkyl is $C_3$-$C_{30}$ cycloalkyl. In some embodiments, cycloalkyl is $C_3$-$C_{12}$ cycloalkyl. In some embodiments, cycloalkyl is $C_3$-$C_8$ cycloalkyl.

The cycloalkyl group may be optionally substituted, i.e. substituted or unsubstituted. Where substituted, the substituted group(s) is(are) individually and independently selected from the group consisting of cycloalkyl, aryl, heteroaryl, hetero alicyclic, hydroxy, hydro carboxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, —NR'R" or amino including mono- and bi-substituted amino group, and the protected derivatives thereof.

In some embodiments, $C_3$-$C_{30}$ cycloalkyl is substituted with a halogen.

The term "alkoxy" as used herein refers to the formula —OR, wherein R is an alkyl group defined as above, e.g. methoxy, ethoxy, n-propoxy, 1-methylethoxy (isopropoxy), n-butoxy, iso-butoxy, sec-butoxy, t-butyoxy, amoxy, t-amoxy, etc. The alkyl moiety of the alkoxy group can be optionally substituted, as defined in the above alkyl portion.

In some embodiments, alkoxy is $C_1$-$C_{30}$ alkoxy. In some embodiments, alkoxy is $C_1$-$C_{12}$ alkoxy. In some embodiments, alkoxy is $C_1$-$C_8$ alkoxy.

In some embodiments, $C_1$-$C_{30}$ alkoxy is substituted with a halogen.

The term "carboxylic ester group" as used herein refers to the formula RC(=O)OR'—, wherein R is hydrocarbyl or hydrogen, and R' is hydrocarbyl.

In some embodiments, carboxylic ester group is $C_1$-$C_{30}$ carboxylic ester group. In some embodiments, carboxylic ester group is $C_1$-$C_{12}$ carboxylic ester group. In some embodiments, carboxylic ester group is $C_1$-$C_8$ carboxylic ester group.

The term "halogen" as used herein refers to bromine, chlorine, fluorine or iodine.

The term "receptor" as used herein refers to a molecule capable of receiving electrons.

The term "conjugated electron donor" as used herein refers to a conjugated molecule capable of donating electrons.

The term "conjugated electron receptor" as used herein refers to a conjugated molecule capable of receiving an electron.

The term "organic small molecule dye" as used herein refers to an organic small molecule compound which can dye a fiber or other substances and possess strong absorption in the visible region.

SPECIFIC EMBODIMENTS

In an aspect, the present application relates to a donor-receptor type oligothiophene compound represented by the following general formula:

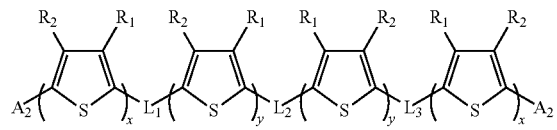

wherein x is an integer of 0 to 50, y is an integer of 1 to 50;

$R_1$ and $R_2$ are each independently selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, wherein $R_1$ and $R_2$ may be identical or different, but $R_1$ and $R_2$ are not H simultaneously;

$L_1$, $L_2$ and $L_3$ are each independently selected from a bridged conjugated electron donor unit and a bridged conjugated electron receptor unit; and $A_2$ is a terminal receptor unit.

In another aspect, the present application relates to a donor-receptor type oligothiophene compound of general formulae (1) to (6):

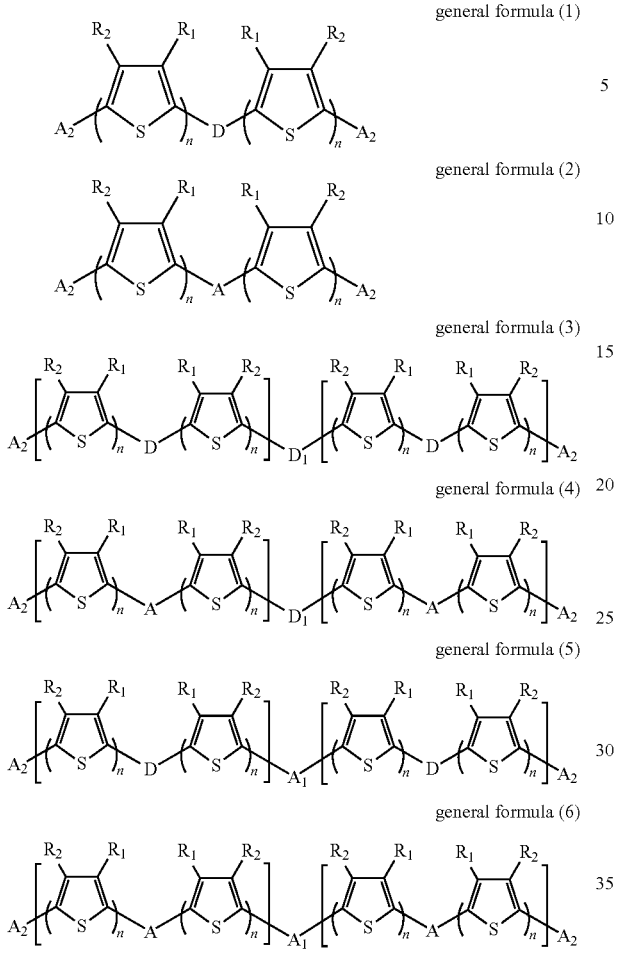

general formula (1)
general formula (2)
general formula (3)
general formula (4)
general formula (5)
general formula (6)

wherein n is an integer of 1 to 50;

$R_1$ and $R_2$ are each independently selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, wherein $R_1$ and $R_2$ may be identical or different, but $R_1$ and $R_2$ are not H simultaneously;

D and $D_1$ are each independently a bridged conjugated electron donor unit;

A and $A_1$ are each independently a bridged conjugated electron receptor unit; and $A_2$ is a terminal receptor unit.

In some embodiments, in the donor-receptor type oligothiophene compound comprising a receptor terminal of general formulae (1) to (6), D and $D_1$ are each independently selected from group 7 to group 20:

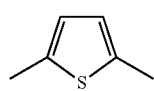

7

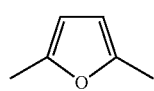

8

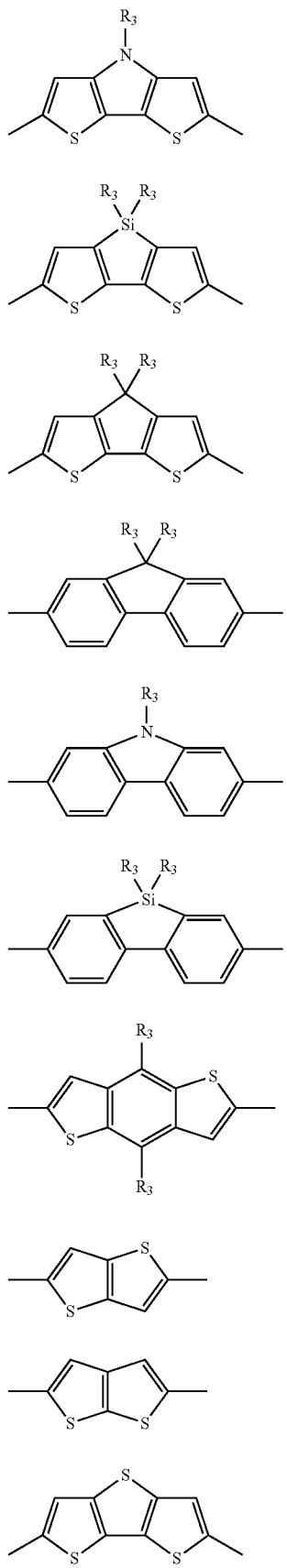

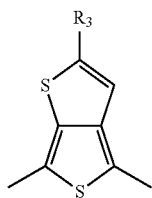

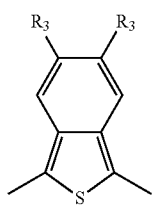

wherein $R_3$ is selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof.

In some embodiments, in the donor-receptor type oligothiophene compound comprising a receptor terminal of general formulae (1) to (6), A and $A_1$ are each independently selected from group 21 to group 30:

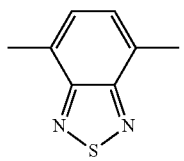

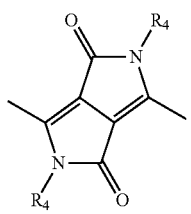

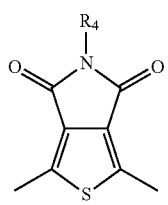

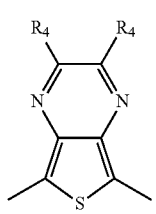

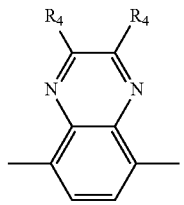

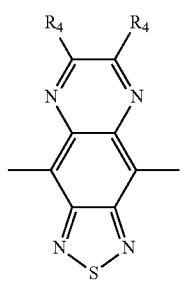

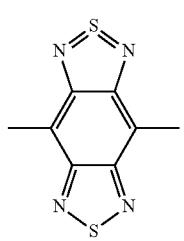

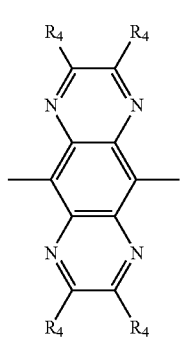

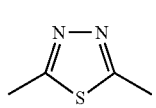

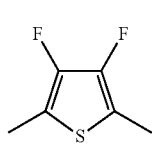

wherein $R_4$ is selected from the group consisting of $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof.

In some embodiments, in the donor-receptor type oligothiophene compound comprising a receptor terminal of general formulae (1) to (6), $A_2$ is an organic small molecule dye group.

In some embodiments, in the donor-receptor type oligothiophene compound comprising a receptor terminal of general formulae (1) to (6), $A_2$ is selected from group 31 to group 60:

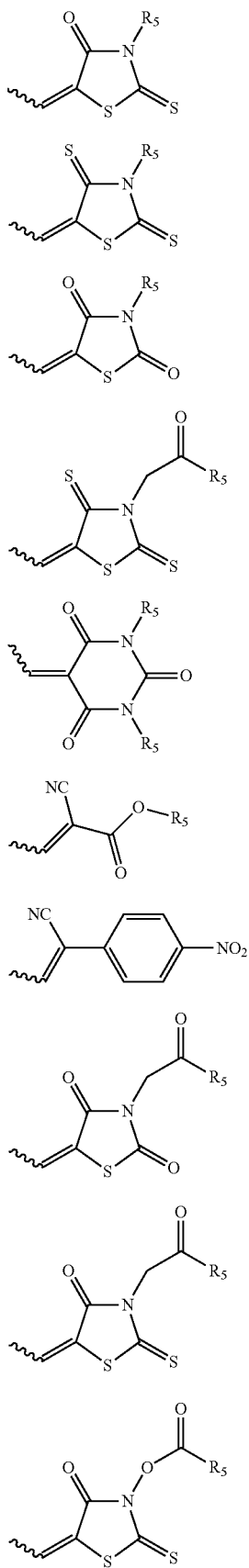
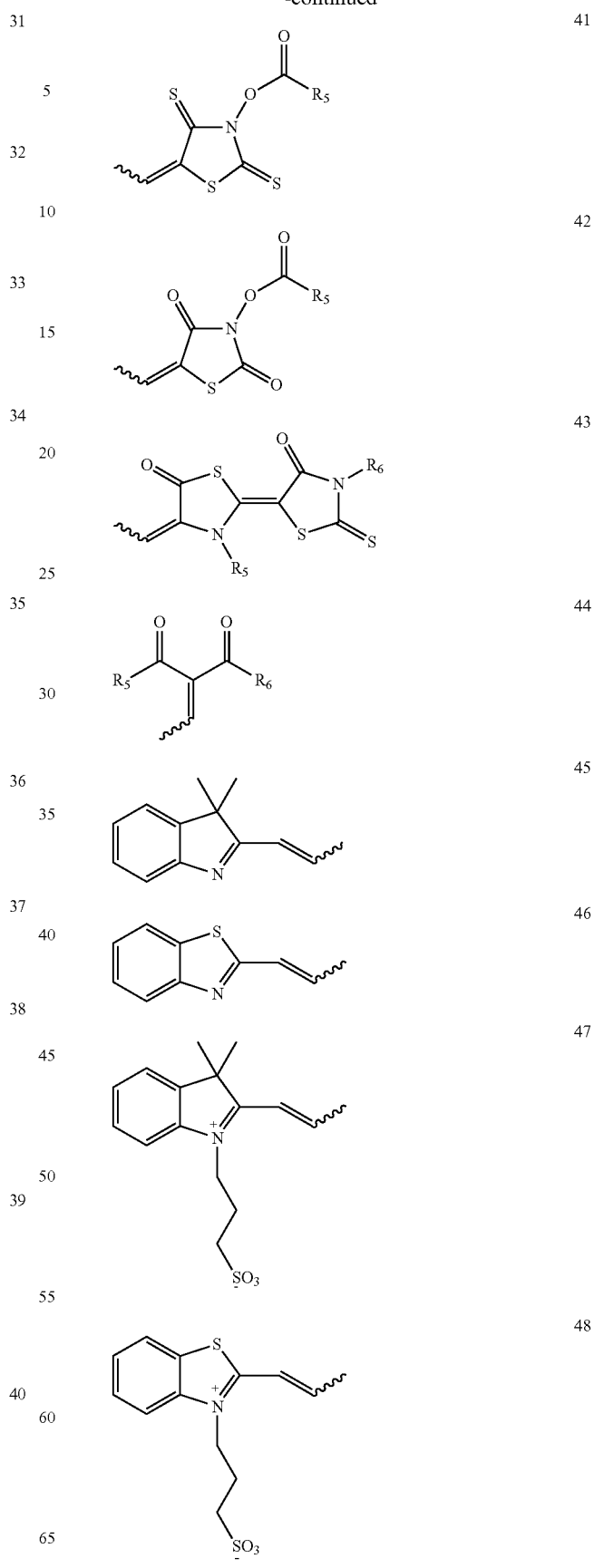

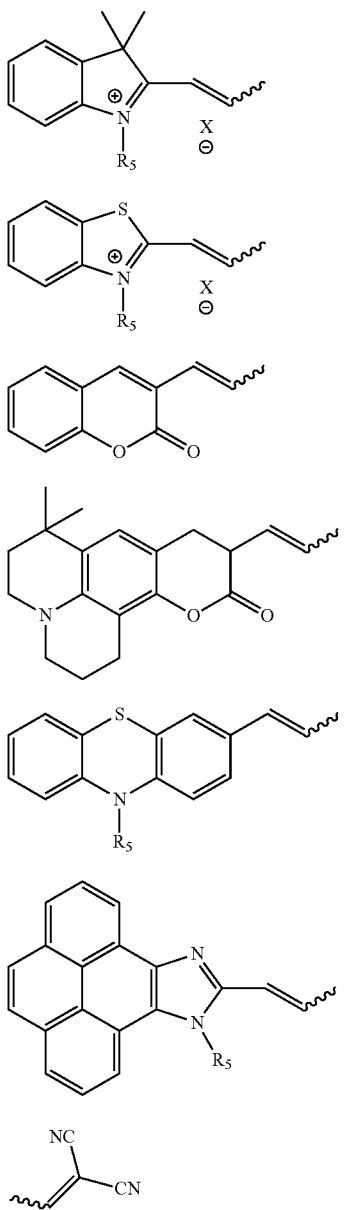

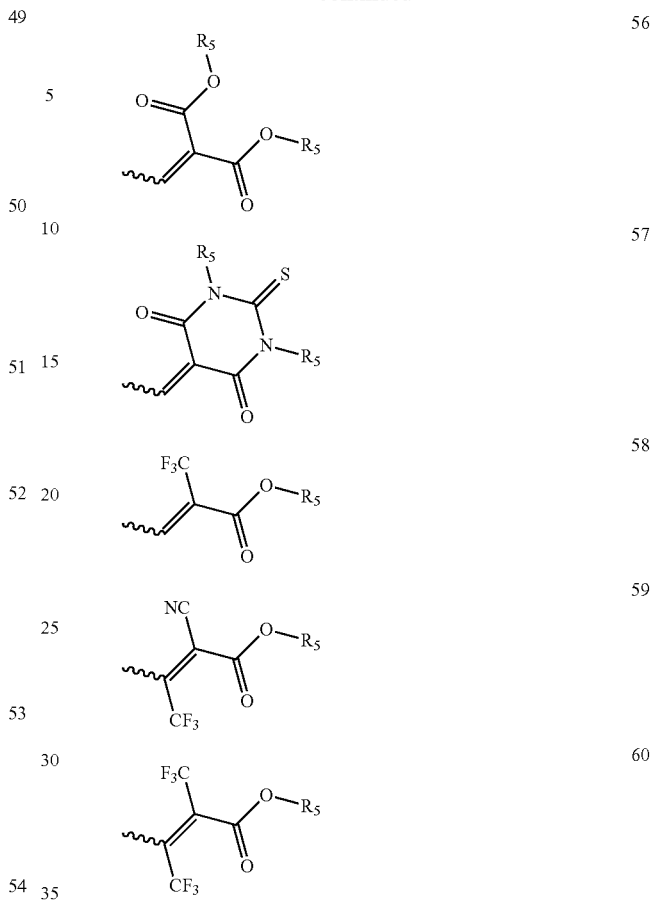

wherein $R_5$ and $R_6$ are each independently selected from the group consisting of $C_1$-$C_{30}$ alkyl, $C_3$-$C_{30}$ cycloalkyl, $C_1$-$C_{30}$ alkoxy and halo-substituted derivatives thereof, and $X^-$ is an anion such that $A_2$ can be a neutral group, when $A_2$ is group 55, n in the general formula (1) is 4 or more.

In some embodiments, when $A_2$ is group 55, n in the general formula (1) is not 3.

In some embodiments, the compound has a structure selected from the group consisting of:

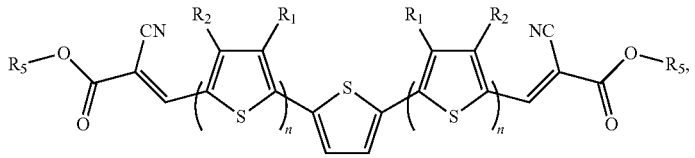

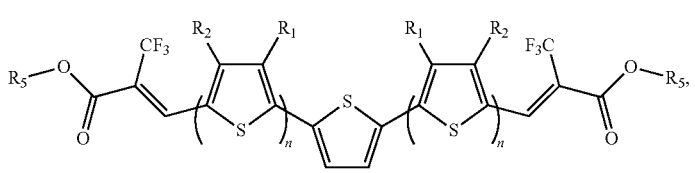

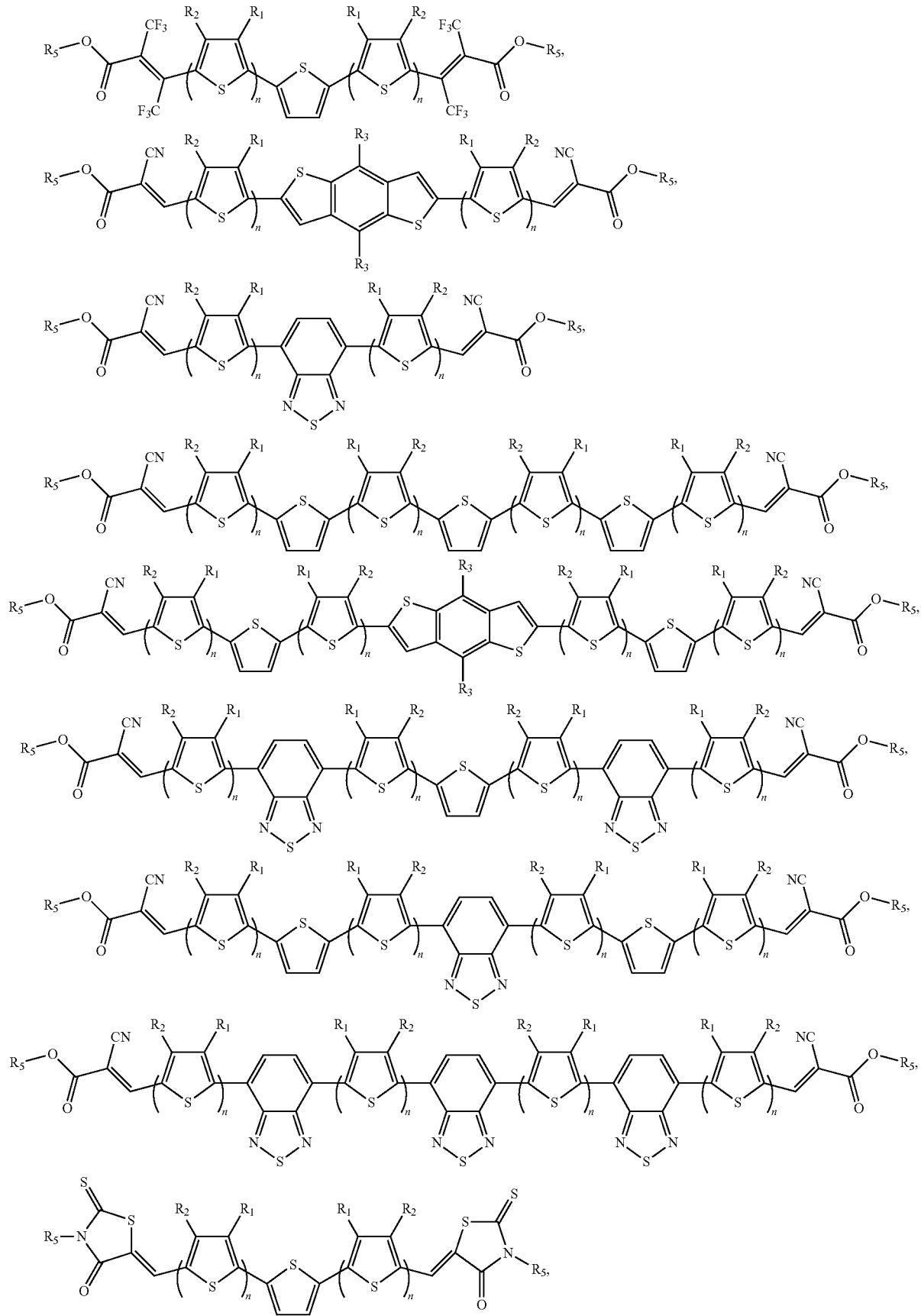

-continued
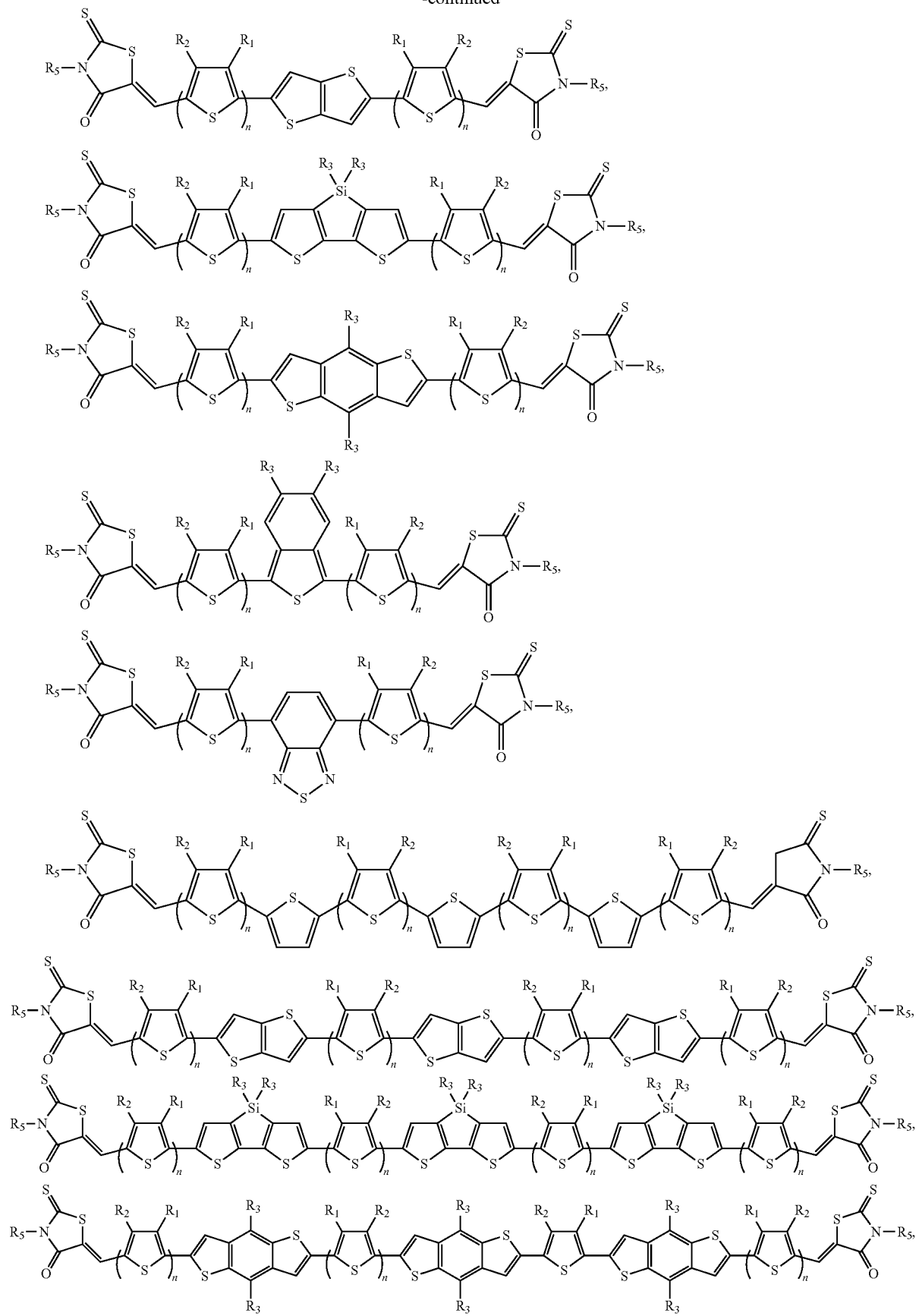

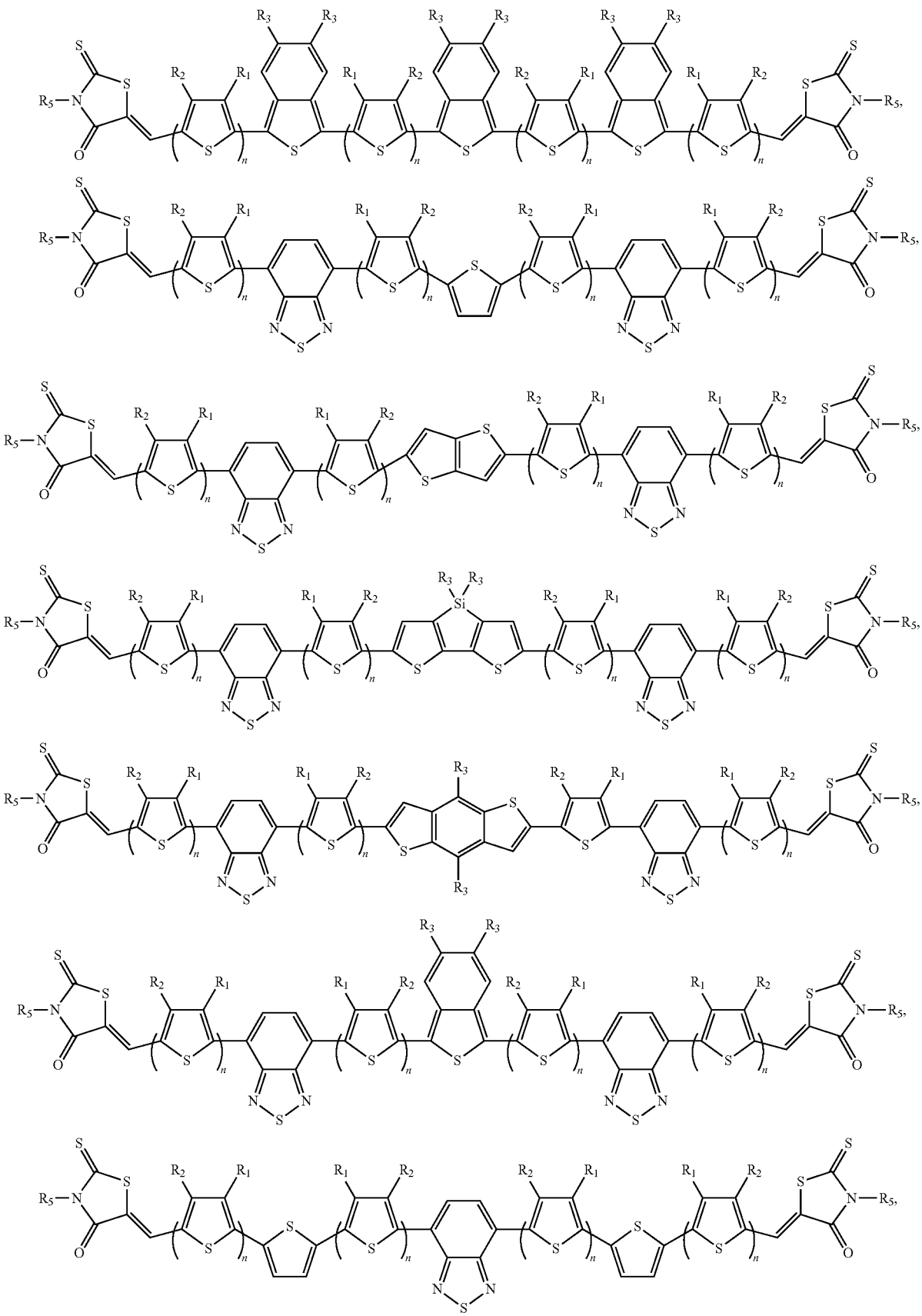

-continued

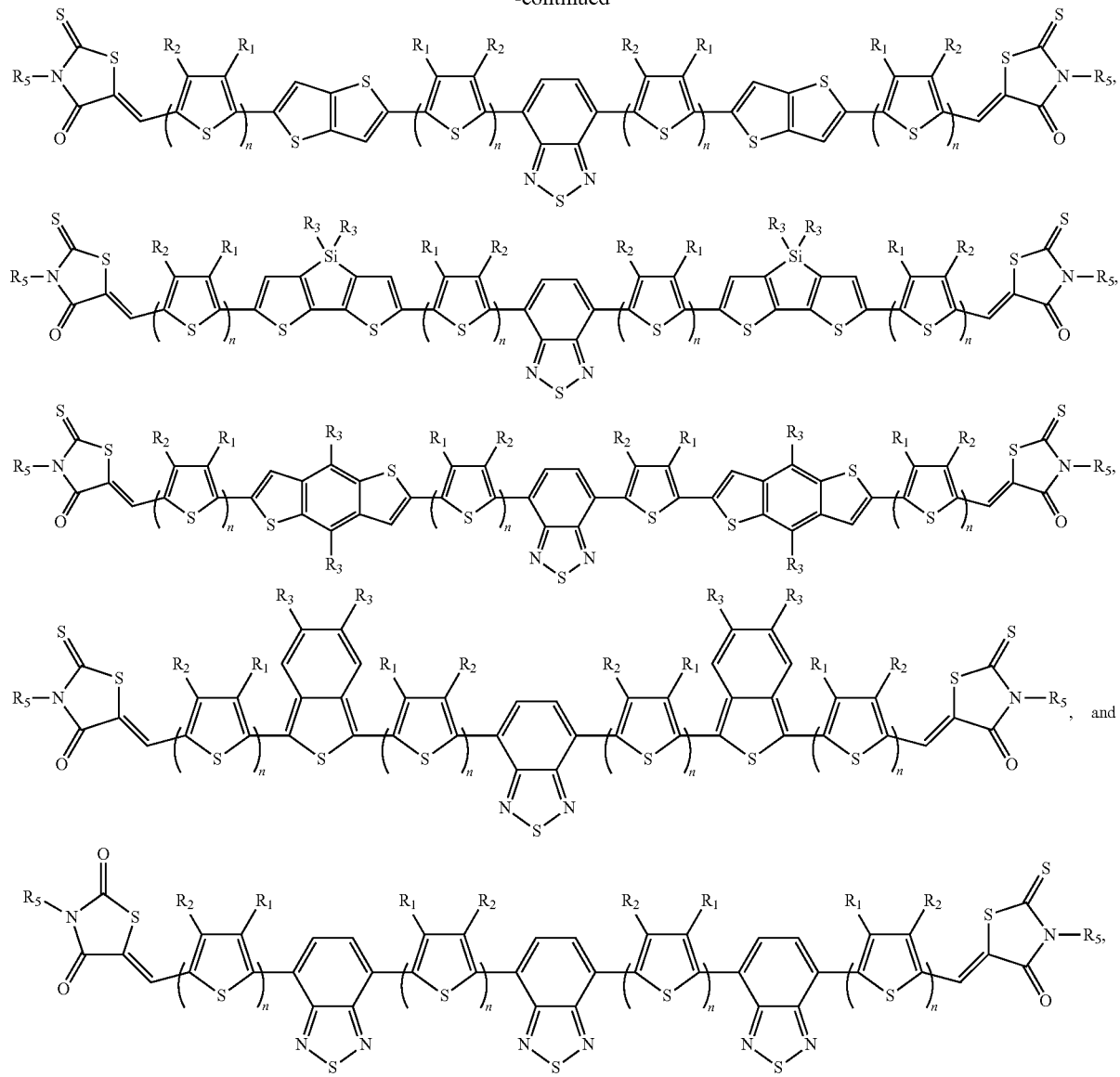

wherein n is an integer of 1 to 50;

$R_1$ and $R_2$ are each independently selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, wherein $R_1$ and $R_2$ may be identical or different, but $R_1$ and $R_2$ are not H simultaneously;

$R_3$ is selected from the group consisting of H, $C_1$-$C_{30}$ alkyl, $C_3$-$C_{30}$ cycloalkyl, $C_1$-$C_{30}$ alkoxy and halo-substituted derivatives thereof, and $R_5$ is selected from the group consisting of $C_1$-$C_{30}$ alkyl, $C_3$-$C_{30}$ cycloalkyl, $C_1$-$C_{30}$ alkoxy and halo-substituted derivatives thereof.

In some embodiments, in the donor-receptor type oligothiophene compound comprising a receptor terminal of general formulae (1) to (6), D and $D_1$ are each selected from the group consisting of group 7, group 10, group 15, group 16 and group 20, wherein $R_3$ is selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof.

In some embodiments, in the donor-receptor type oligothiophene compound comprising a receptor terminal of general formulae (1) to (6), A and $A_1$ are each independently selected from the group consisting of group 21 and group 23, wherein $R_4$ is selected from the group consisting of $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof.

In some embodiments, in the donor-receptor type oligothiophene compound comprising a receptor terminal of general formulae (1) to (6), $A_2$ is selected from the group consisting of group 31, group 35, group 36, group 40, group 43, group 44, group 47 and group 55, wherein $R_5$ and $R_6$ are each independently selected from the group consisting of $C_1$-$C_{30}$ alkyl, $C_3$-$C_{30}$ cycloalkyl, $C_1$-$C_{30}$ alkoxy and halo-substituted derivatives thereof.

In some embodiments, in the donor-receptor type oligothiophene compound comprising a receptor terminal of general formulae (1) to (6), D and $D_1$ are each independently selected from the group consisting of group 7, group 10, group 15, group 16 and group 20, A and $A_1$ are each independently selected from the group consisting of group 21 and group 23, and $A_2$ is selected from the group consisting of group 31, group 35, group 36, group 40, group 43, group 44, group 47 and group 55, wherein $R_3$ is selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, $R_4$ is selected from the group consisting of $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, and $R_5$ and $R_6$ are each independently selected from the group consisting of $C_1$-$C_{30}$ alkyl, $C_3$-$C_{30}$ cycloalkyl, $C_1$-$C_{30}$ alkoxy and halo-substituted derivatives thereof.

In some embodiments, in the donor-receptor type oligothiophene compound comprising a receptor terminal of general formulae (1) to (6), n is an integer of 1 to 30. In some embodiments, in the donor-receptor type oligothiophene compound comprising a receptor terminal of general formulae (1) to (6), n is an integer of 1 to 10.

In some embodiments, in the donor-receptor type oligothiophene compound comprising a receptor terminal of general formulae (1) to (6), $X^-$ is selected from the group consisting of halogen ion, $BF_4^-$, $PF_6^-$, $SO_3^-$ and $CF_3SO_3^-$.

In some embodiments, the donor-receptor type oligothiophene compound of general formulae (1) to (6) is selected from the group consisting of:

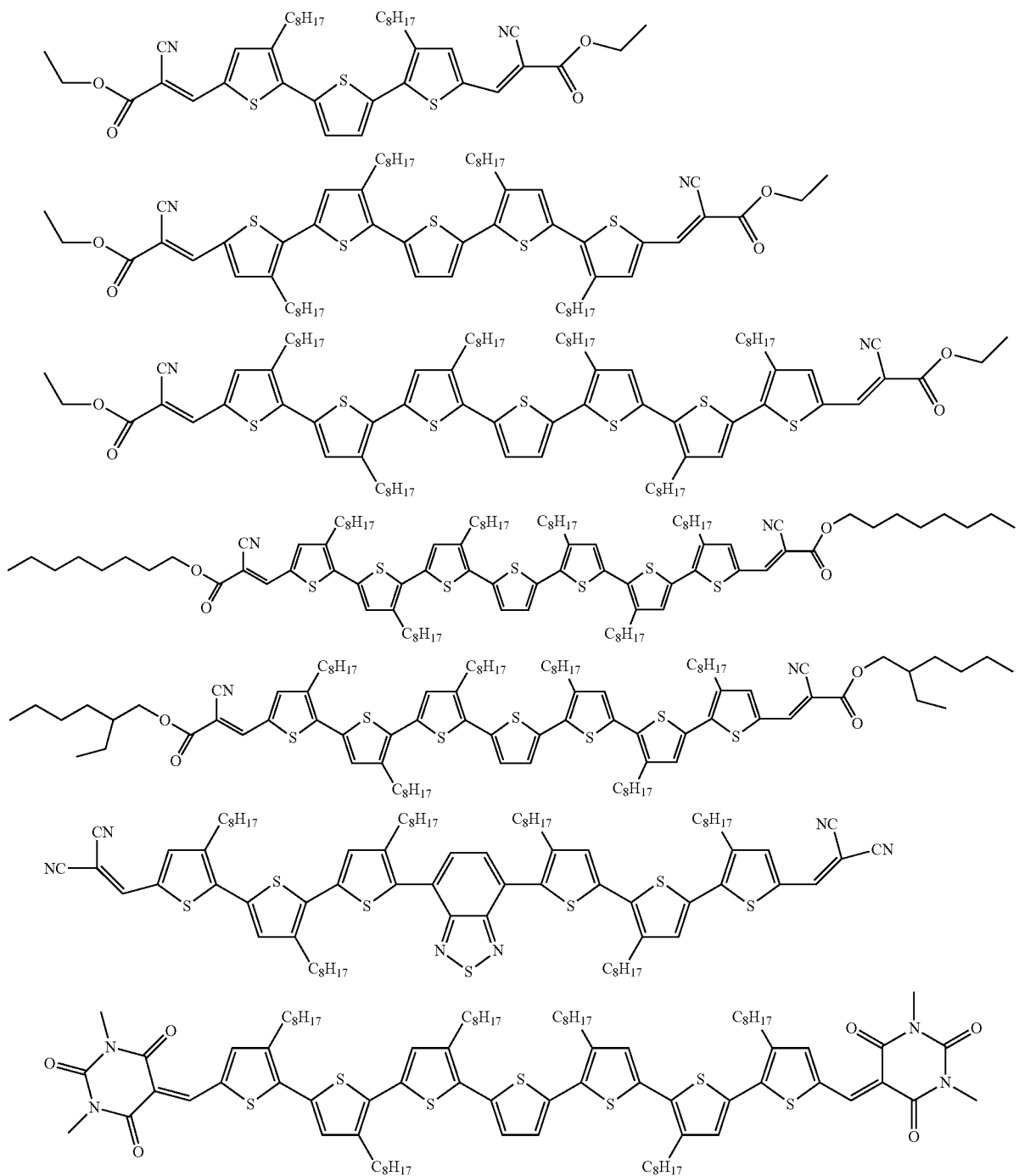

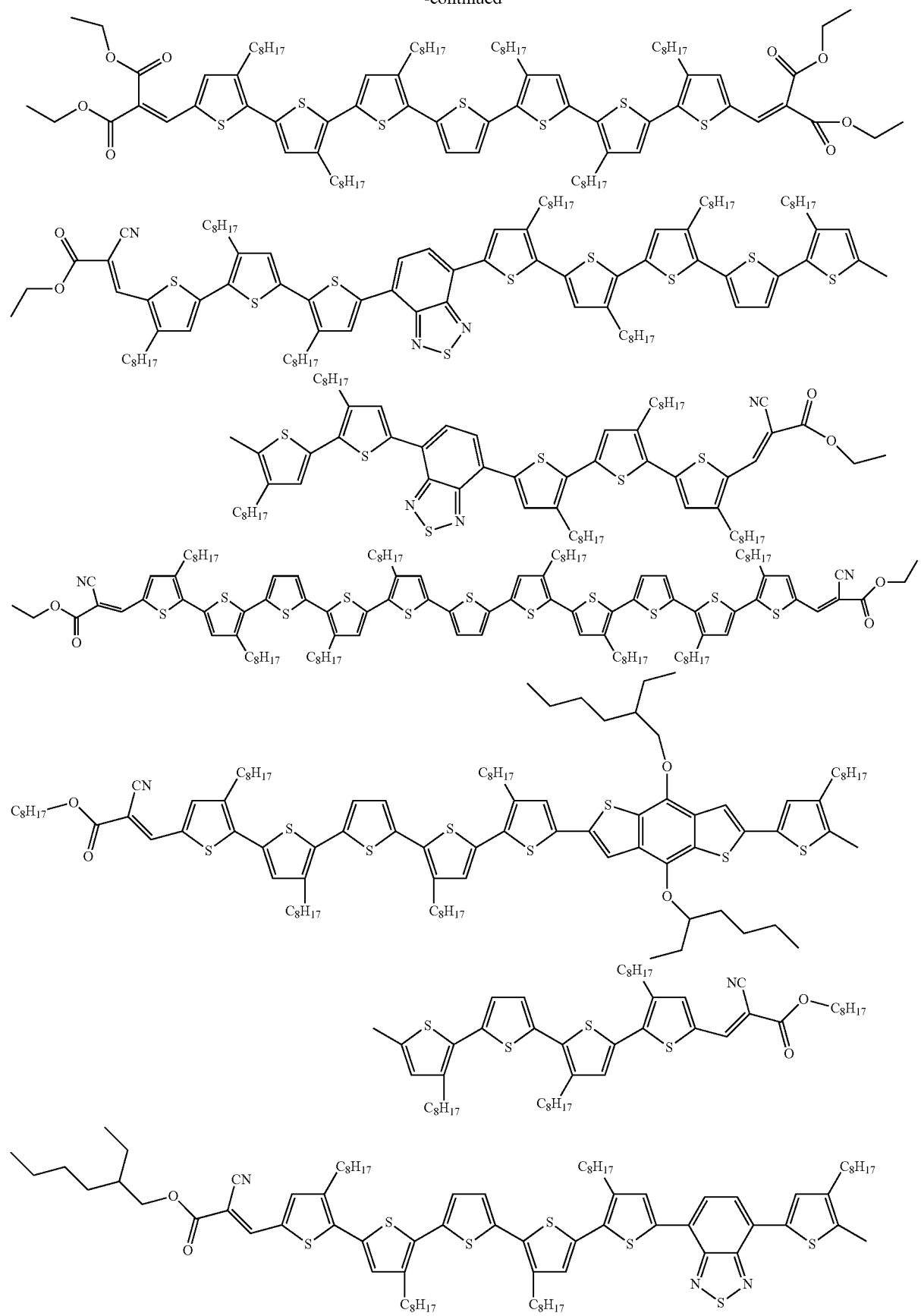

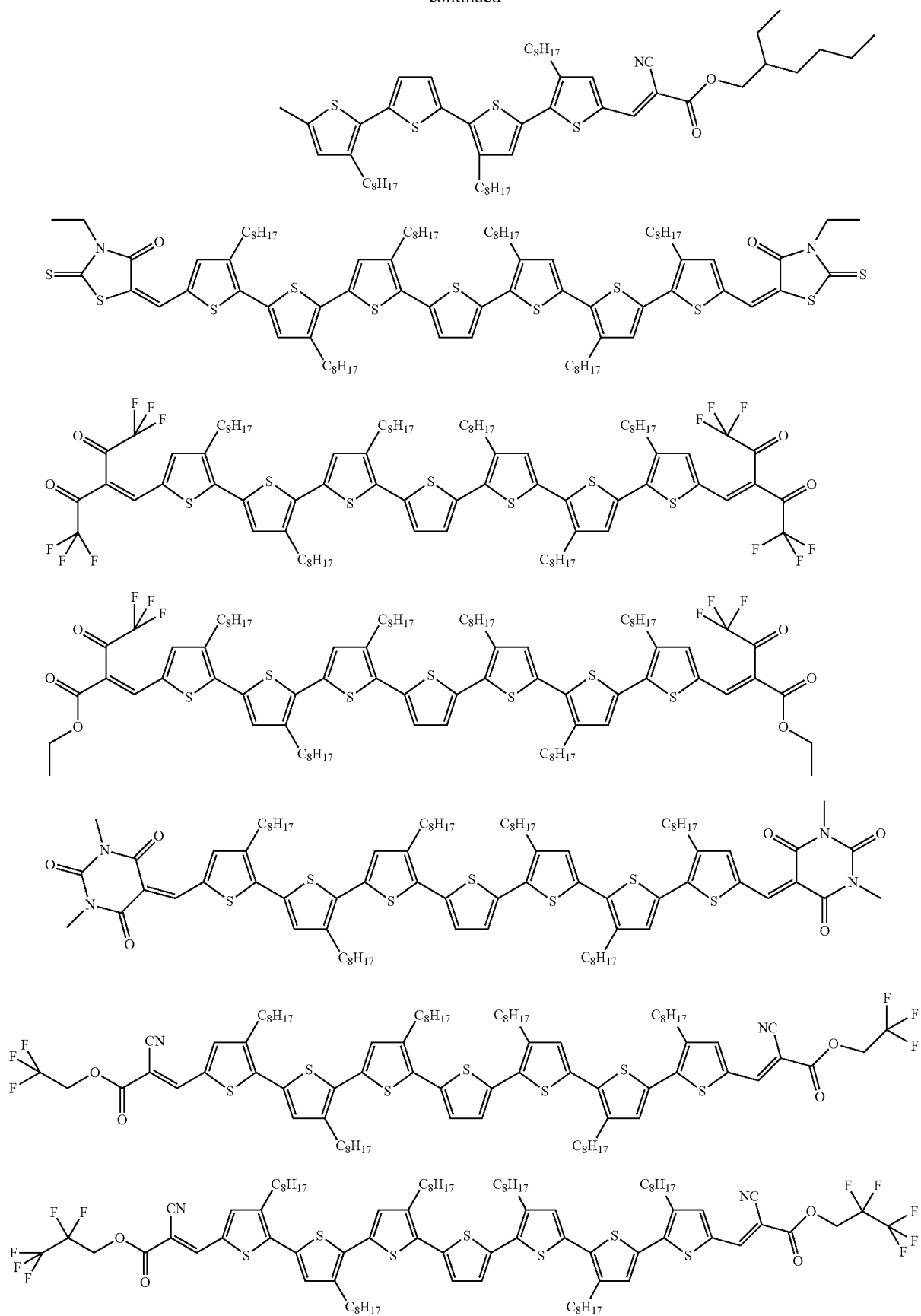

-continued
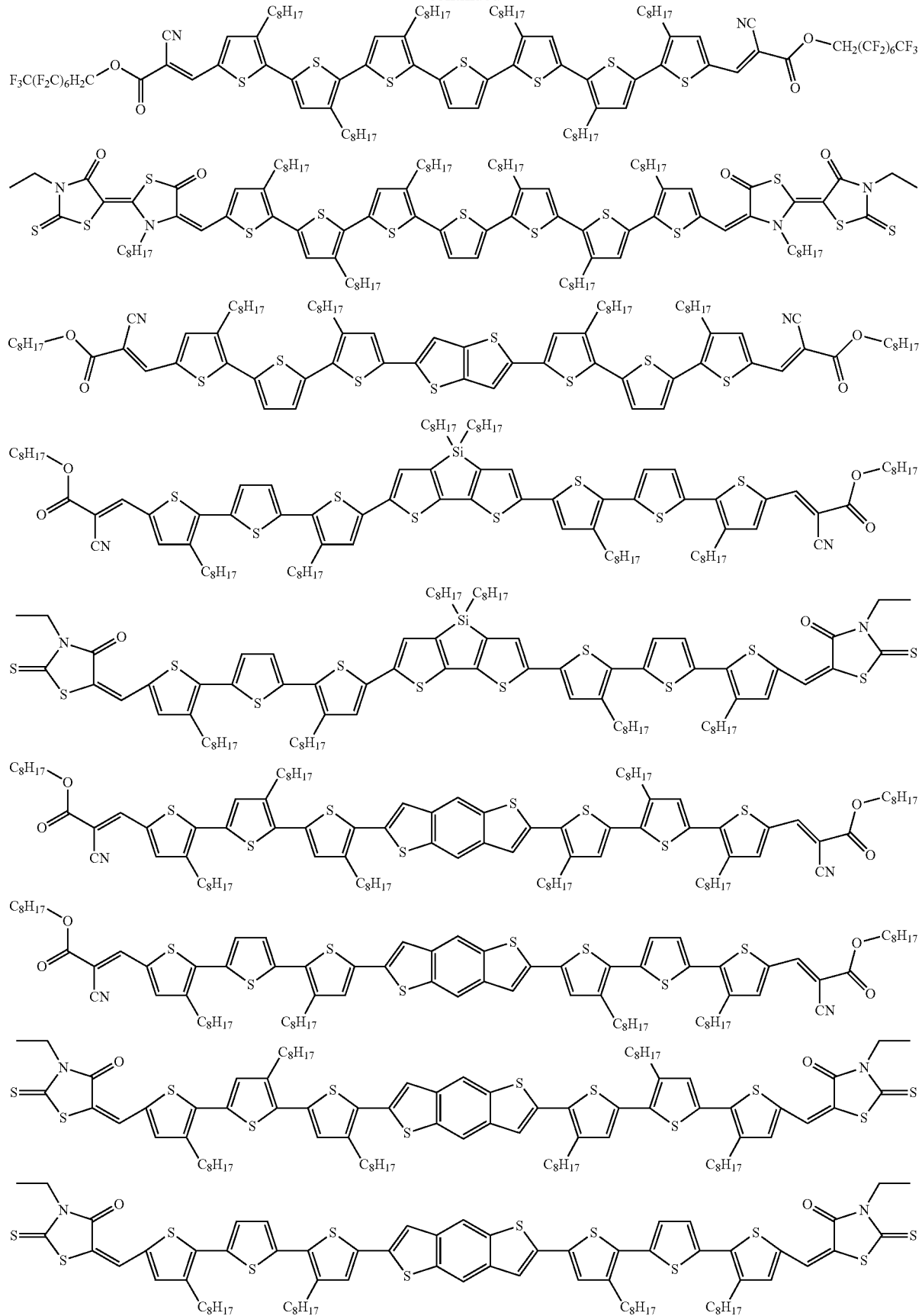

-continued
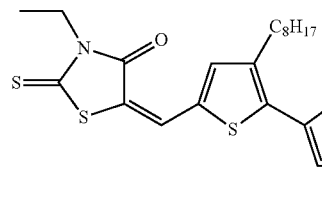
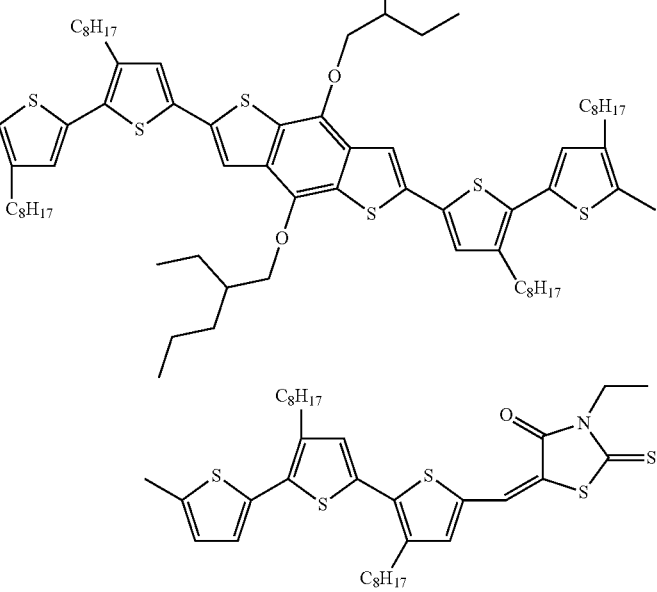
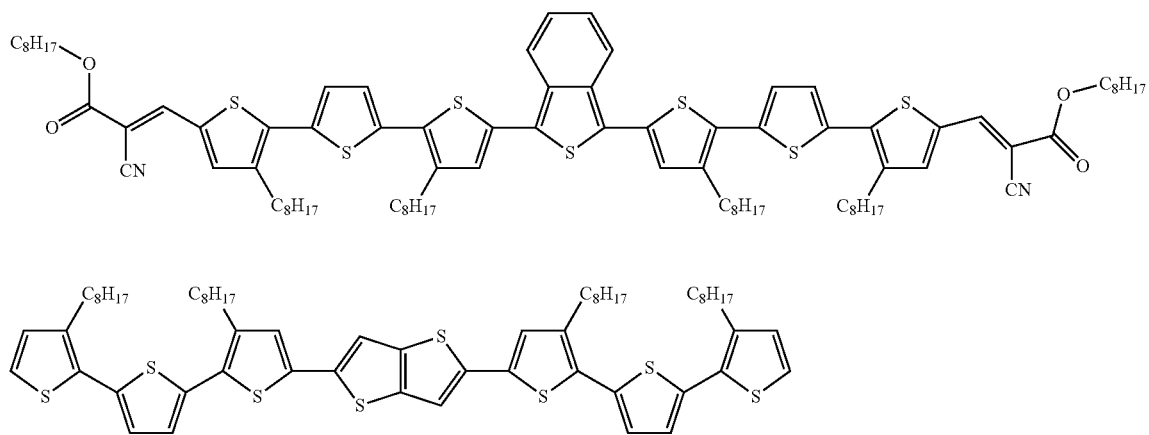
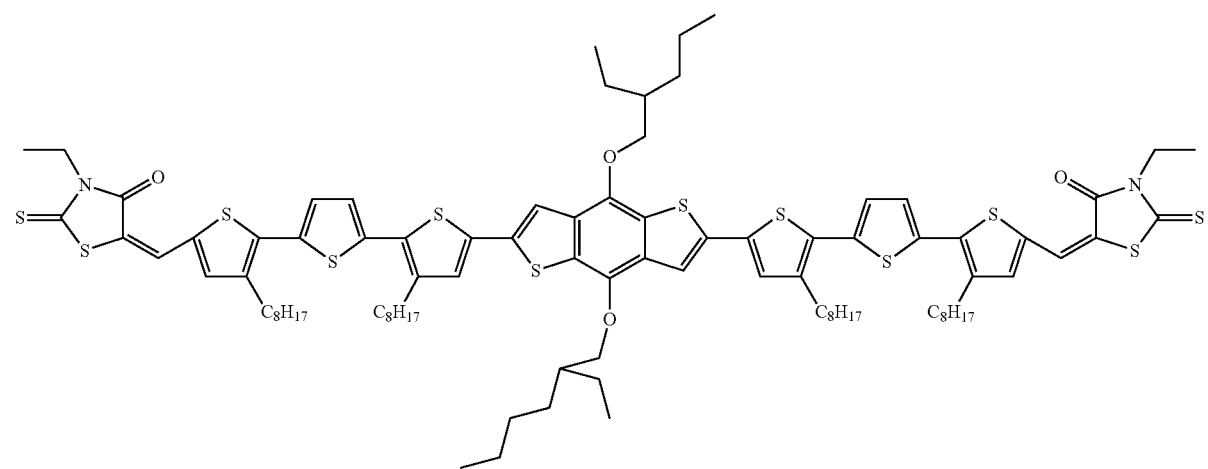

37 38
-continued
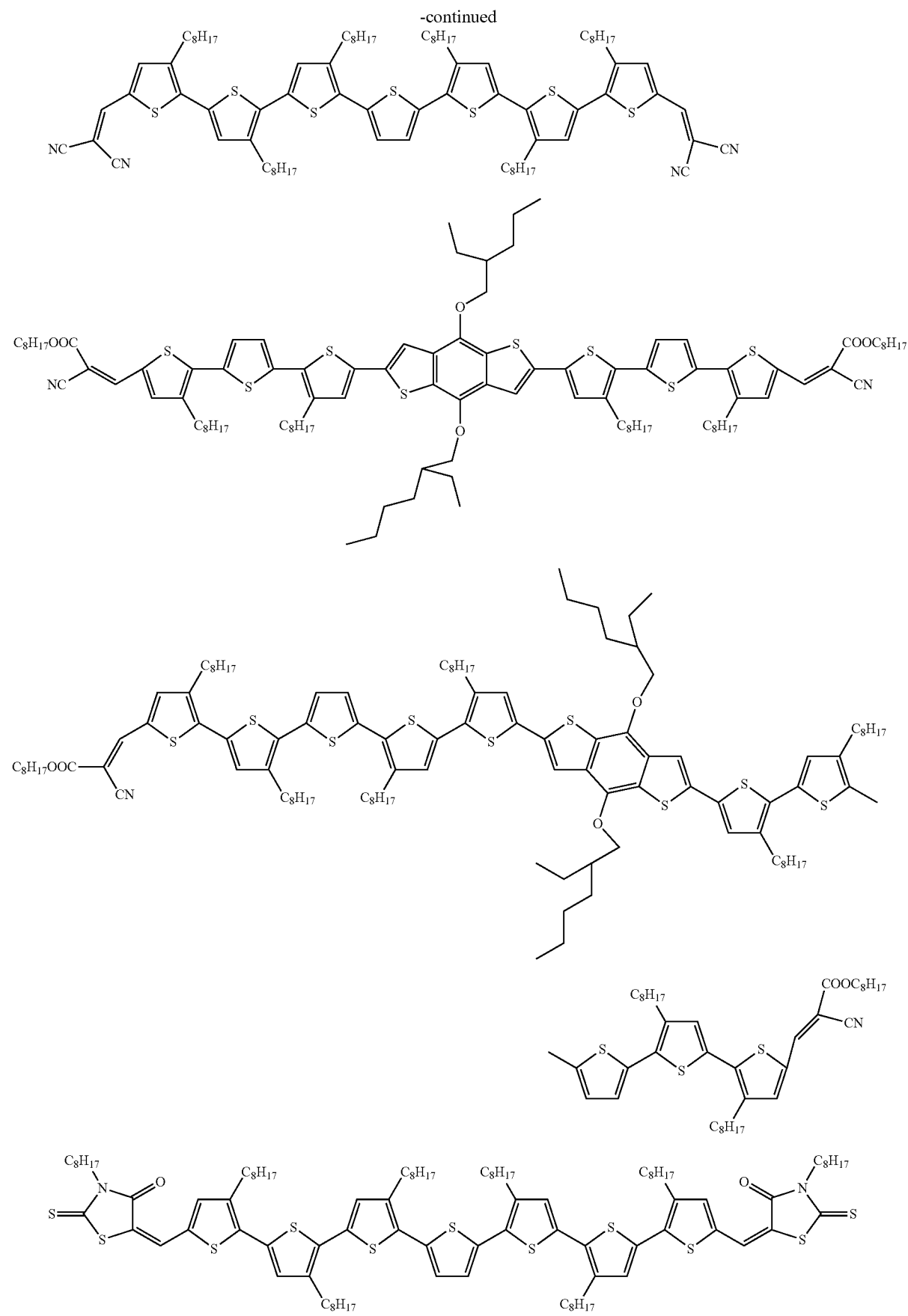

-continued
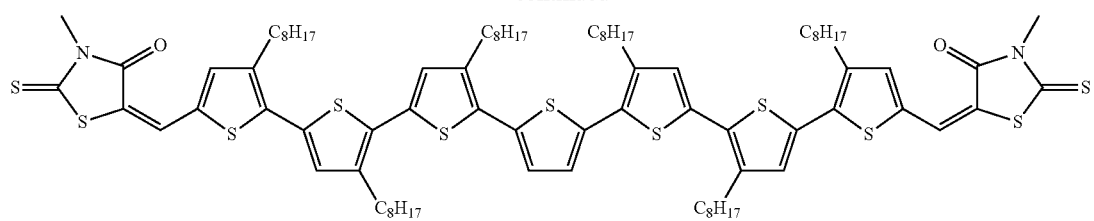
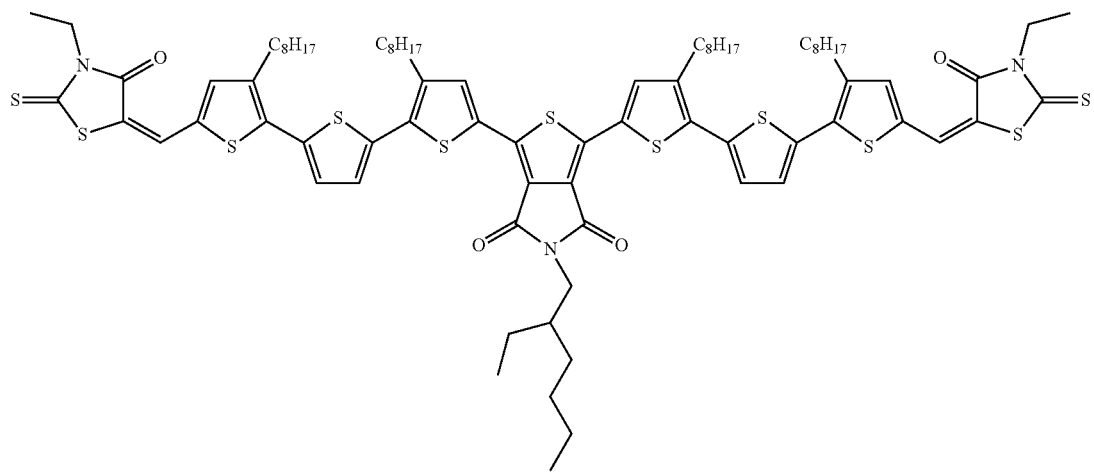
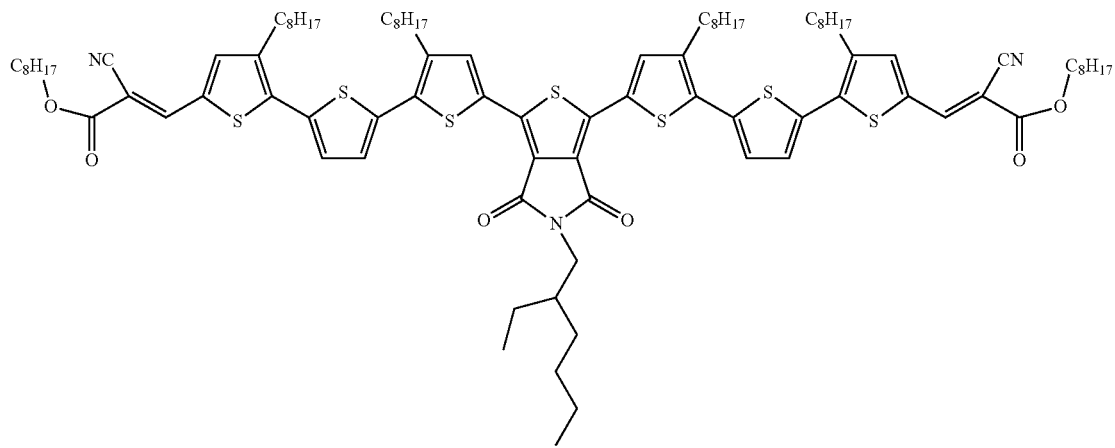
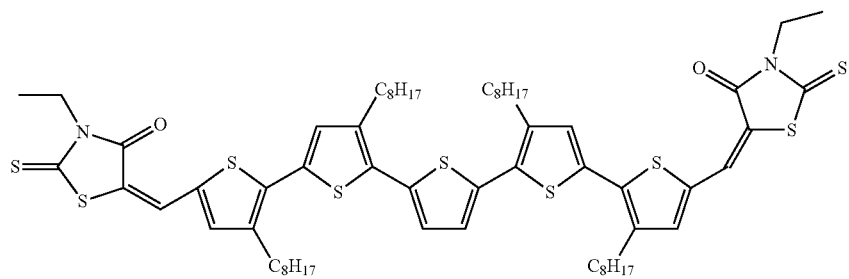

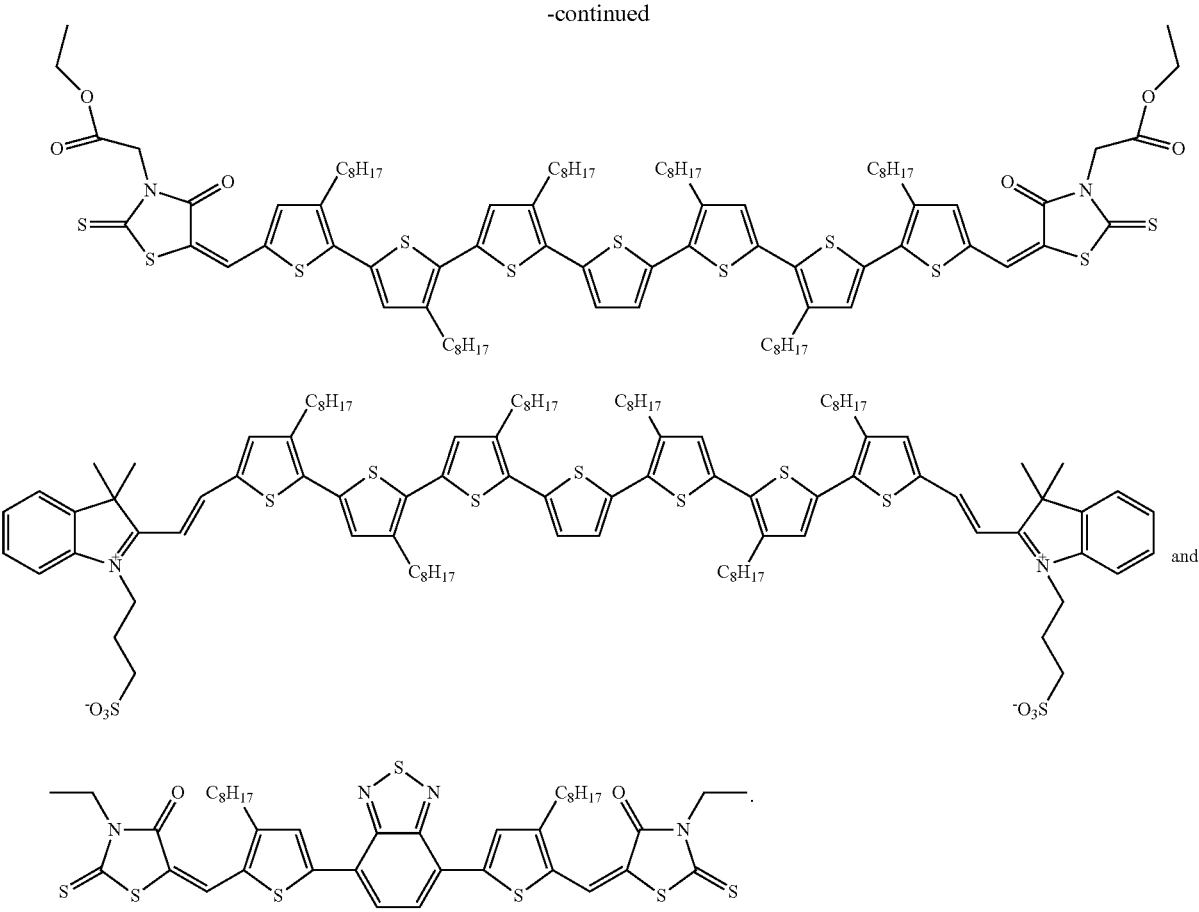

In another aspect, the present application relates to a process for preparing a donor-receptor type oligothiophene compound comprising a receptor terminal of general formulae (1) to (6), comprising carrying out a Knoevenagel condensation reaction of a donor bridged oligothiophene comprising a receptor terminal with a receptor end group monomer through a bisaldehyde group donor bridged oligothiophene in the presence of a solvent and a catalyst to obtain the compound.

In some embodiments, the solvent used in the process for preparing the donor-receptor type oligothiophene compound comprising a receptor terminal of general formulae (1) to (6) is a polar solvent. In some embodiments, the solvent used in the process for preparing the donor-receptor type oligothiophene compound comprising a receptor terminal of general formulae (1) to (6) is trichloromethane.

In some embodiments, the catalyst used in the process for preparing the donor-receptor type oligothiophene compound comprising a receptor terminal of general formulae (1) to (6) is an alkaline compound.

Exemplary alkaline compounds that can be used in the present application include, but are not limited to, sodium carbonate, sodium hydride, potassium carbonate, potassium tert-butoxide, triethylamine, N,N-dimethylpyridine, sodium hydride and diisopropyl ethylamine.

In some embodiments, the catalyst used in the process for preparing the donor-receptor type oligothiophene compound comprising a receptor terminal of general formulae (1) to (6) is alkylamine.

Exemplary alkylamines that can be used in the present application include, but are not limited to, triethylamine, N,N-dimethylpyridine and diisopropyl ethylamine.

In some embodiments, the catalyst used in the process for preparing the donor-receptor type oligothiophene compound comprising a receptor terminal of general formulae (1) to (6) is triethylamine.

In some embodiments, the amount of the catalyst used in the process for preparing the donor-receptor type oligothiophene compound comprising a receptor terminal of general formulae (1) to (6) is 0.1-20 mol %.

In some embodiments, the process for preparing the donor-receptor type oligothiophene compound comprising a receptor terminal of general formulae (1) to (6) is carried out under protective gas. In some embodiments, the process for preparing the donor-receptor type oligothiophene compound comprising a receptor terminal of general formulae (1) to (6) is carried out under argon gas.

In some embodiments, the process for preparing the donor-receptor type oligothiophene compound comprising a receptor terminal of general formula (1) is outlined as follows:

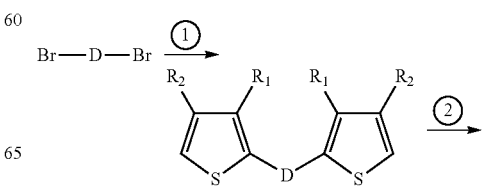

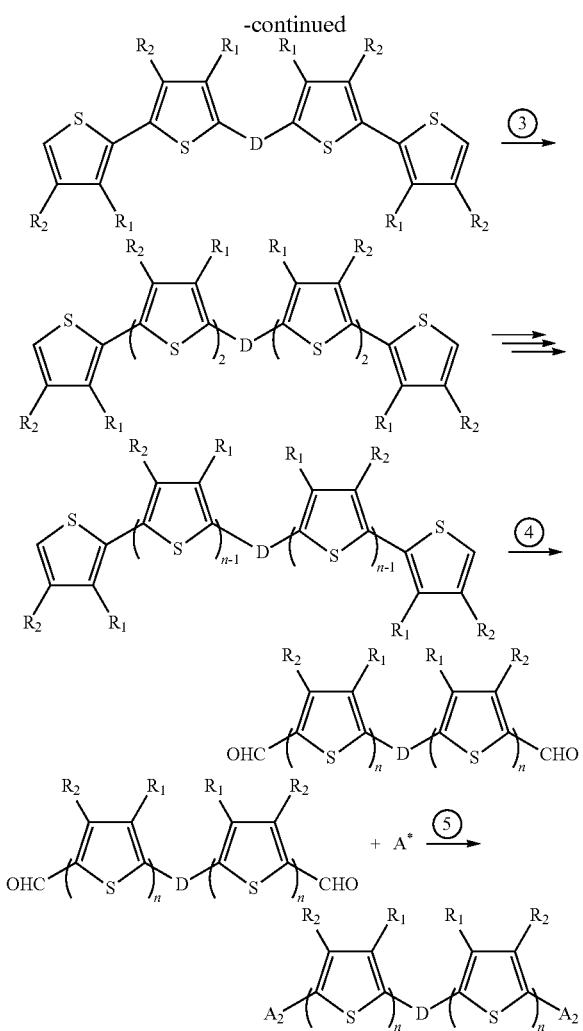

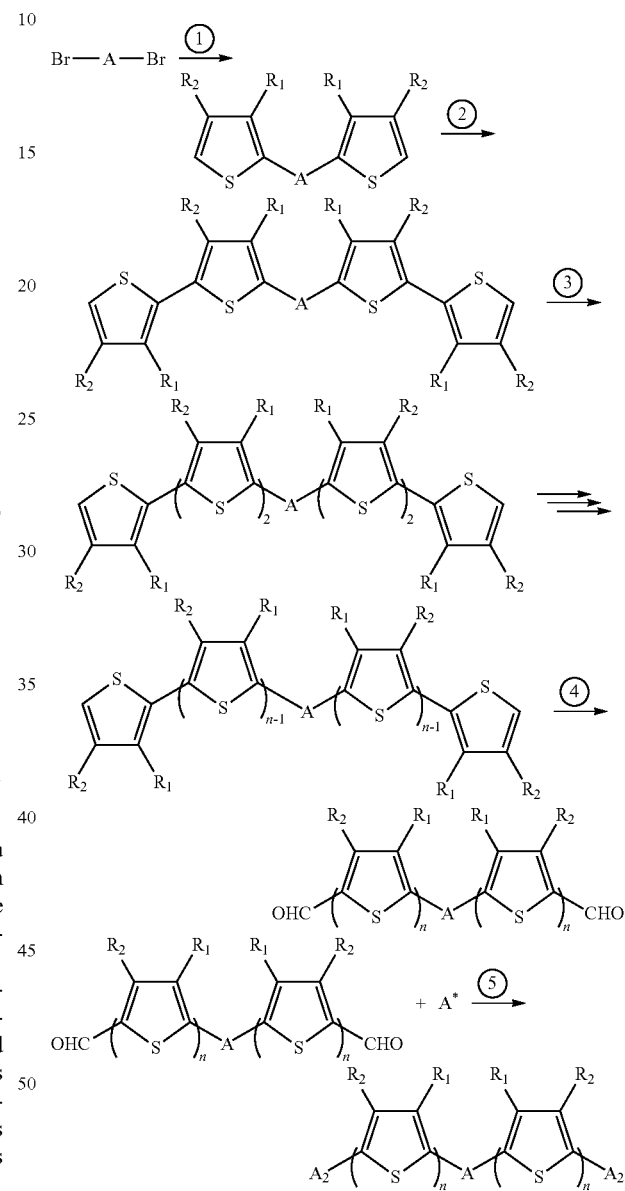

wherein step ☐: the starting material is refluxed with a Grignard reagent of 2-bromo-3(and/or-4)-alkylthiophene in ethyl ether for 1 to 7 days under argon gas protection in the presence of Ni(dppp)Cl$_2$ as a catalyst without water and oxygen;

step ☐: the donor bridged oligothiophene is firstly brominated with NBS (the molar ratio of donor bridged oligothiophene to NBS is 1:2) in a mixture of trichloromethane and glacial acetic acid (1:1 vol/vol), and the resultant product is refluxed with a Grignard reagent of 2-bromo-3(and/or-4)-alkylthiophene in ethyl ether for 1 to 7 days under argon gas protection in the presence of Ni(dppp)Cl$_2$ (0.1-20 mol %) as a catalyst without water and oxygen;

step ☐: the donor bridged oligothiophene is firstly brominated with NBS (the molar ratio of donor bridged oligothiophene to NBS is 1:2) in a mixture of trichloromethane and glacial acetic acid (1:1 vol/vol), and the resultant product is refluxed with a Grignard reagent of 2-bromo-3(and/or-4)-alkylthiophene in ethyl ether for 1 to 7 days under argon gas protection in the presence of Ni(dppp)Cl$_2$ (0.1-20 mol %) as a catalyst without water and oxygen;

step ☐: POCl$_3$ is firstly reacted with DMF in an ice bath to give a Vilsmeier reagent, the Vilsmeier reagent in an excessive amount is added dropwise into the oligothiophene in 1,2-dichloroethane, and the mixture is heated under reflux for 1 to 7 days; and step ☐: the resultant mixture is reacted with excessive receptor terminal monomer A* in a solvent of trichloromethane for 1 to 7 days at room temperature, under argon gas protection in the presence of triethylamine (0.1-20 mol %) as a catalyst.

In some embodiments, the process for preparing the donor-receptor type oligothiophene compound comprising a receptor terminal of general formula (2) is outlined as follows.

wherein step ☐: the starting material is refluxed with 2-(trimethylstannyl)-3-alkylthiophene in toluene for 1 to 7 days under argon gas protection in the presence of Pd(PPh$_3$)$_4$ (0.1-20 mol %) as a catalyst without water and oxygen;

step ☐: the receptor bridged oligothiophene is firstly brominated with NBS (the molar ratio of receptor bridged oligothiophene to NBS is 1:2) in a mixture of trichloromethane and glacial acetic acid (1:1 vol/vol), and the resultant product is refluxed with 2-(trimethylstannyl)-3-alkylthiophene in toluene for 1 to 7 days under argon gas protection in the presence of Pd(PPh$_3$)$_4$ (0.1-20 mol %) as a catalyst without water and oxygen;

step □: the receptor bridged oligothiophene is firstly brominated with NBS (the molar ratio of receptor bridged oligothiophene to NBS is 1:2) in a mixture of trichloromethane and glacial acetic acid (1:1 vol/vol), and the resultant product is refluxed with 2-(trimethylstannyl)-3-alkylthiophene in toluene for 1 to 7 days under argon gas protection in the presence of Pd(PPh$_3$)$_4$ (0.1-20 mol %) as a catalyst without water and oxygen;

step □: POCl$_3$ is firstly reacted with DMF in an ice bath to give a Vilsmeier reagent, the Vilsmeier reagent in an excessive amount is added dropwise into the receptor bridged oligothiophene in 1,2-dichloroethane, and the mixture is heated under reflux for 1 to 7 days; and step □: the resultant mixture is reacted with excessive receptor terminal monomer A* in a solvent of trichloromethane for 1-7 days at room temperature, under argon gas protection in the presence of triethylamine (0.1-20 mol %) as a catalyst.

In some embodiments, the process for preparing the donor-receptor type oligothiophene compound comprising a receptor terminal of general formula (3) is outlined as follows.

step □: the donor bridged oligothiophene is firstly brominated with NBS (the molar ratio of donor bridged oligothiophene to NBS is 1:1) in a mixture of trichloromethane and glacial acetic acid (1:1 vol/vol);

step □: a mixture of bromide and distannyl monomer of D (the molar ratio of bromide to distannyl monomer of D is 1:0.5) in a solvent of toluene is reacted with heating and refluxing for 1 to 7 days under argon gas protection in the presence of Pd(PPh$_3$)$_4$ (0.1-20 mol %) as a catalyst without water and oxygen;

step □: to bromide and bis(pinacolato)diboron of D (the molar ratio of bromide to bis(pinacolato)diboron of D is 1:0.5) in a solvent of toluene is added a suitable amount of an aqueous solution of K$_2$CO$_3$ (2 mol/L), and the resultant mixture is heated with reflux for 1 to 7 days under argon gas protection in the presence of Pd(PPh$_3$)$_4$ (0.1-20 mol %) as a catalyst; and

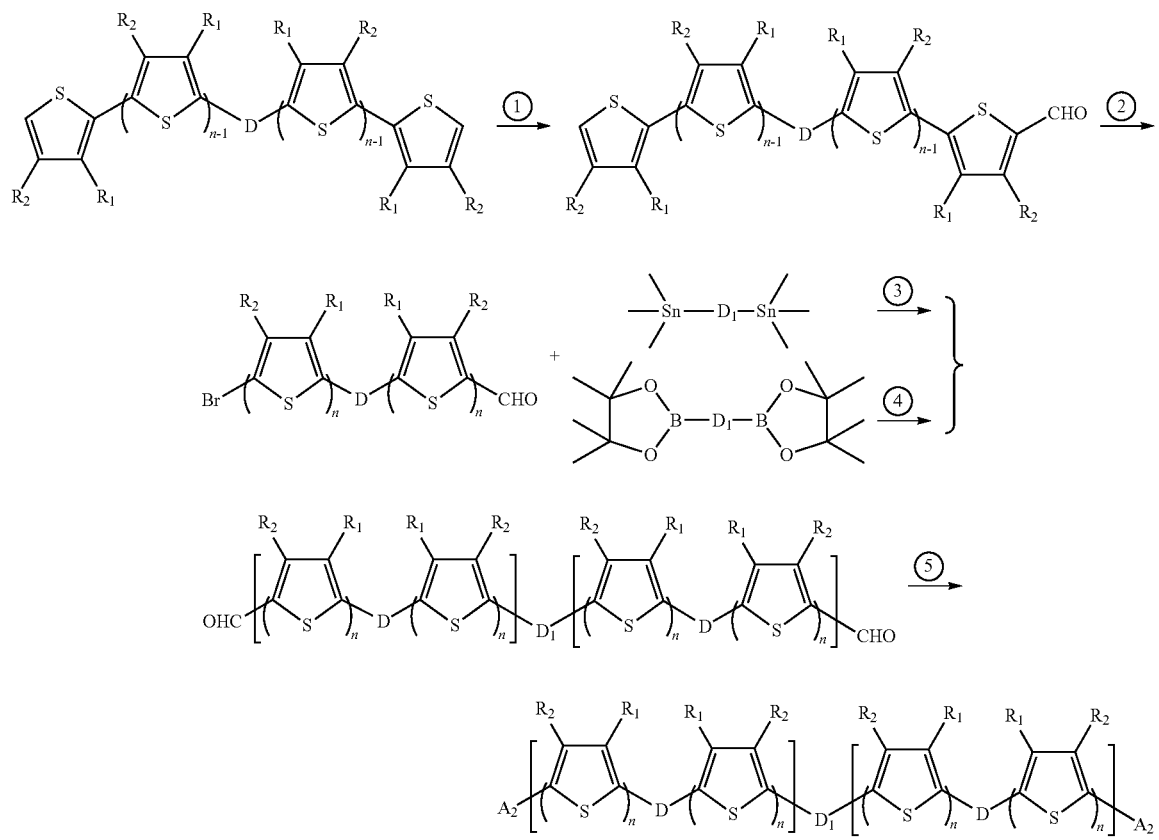

in the above formulae, D and D$_1$ may be identical or different, wherein step □: POCl$_3$ is firstly reacted with DMF in an ice bath to give a Vilsmeier reagent, the Vilsmeier reagent is added dropwise into the donor bridged oligothiophene in 1,2-dichloroethane (the molar ratio of oligothiophene and Vilsmeier reagent is 1:0.5), and the mixture is heated under reflux for 1 to 7 days;

step □: the resultant mixture is reacted with excessive receptor terminal monomer in a solvent of trichloromethane for 1 to 7 days at room temperature, under argon gas protection in the presence of triethylamine (0.1-20 mol %) as a catalyst.

In some embodiments, the process for preparing the donor-receptor type oligothiophene compound comprising a receptor terminal of general formula (4) is outlined as follows.

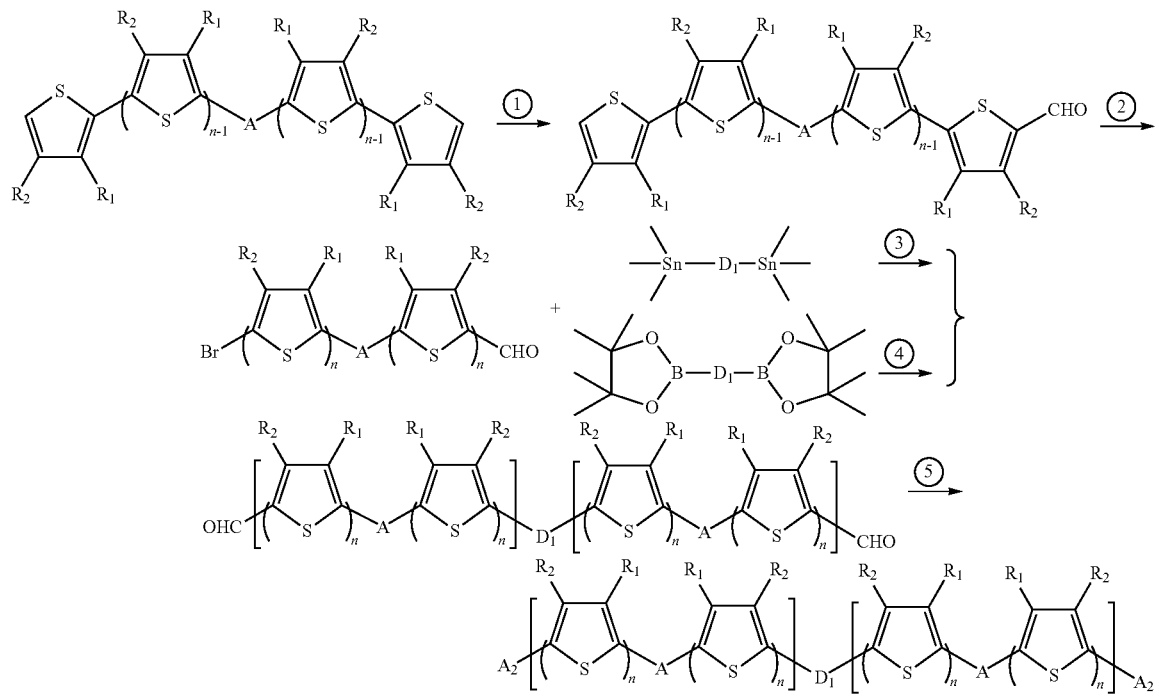

wherein step □: POCl₃ is firstly reacted with DMF in an ice bath to give a Vilsmeier reagent, the Vilsmeier reagent is added dropwise into a solution of the receptor bridged oligothiophene in 1,2-dichloroethane (the molar ratio of receptor bridged oligothiophene and Vilsmeier reagent is 1:0.5), and the resultant mixture is heated under reflux for 1 to 7 days;

step □: the receptor bridged oligothiophene is firstly brominated with NBS (the molar ratio of donor bridged oligothiophene to NBS is 1:1) in a mixture of trichloromethane and glacial acetic acid (1:1 vol/vol);

step □: a mixture of bromide and distannyl monomer of D (the molar ratio of bromide to distannyl monomer of D is 1:0.5) in a solvent of toluene is heated with reflux for 1 to 7 days under argon gas protection in the presence of Pd(PPh₃)₄ (0.1-20 mol %) as a catalyst without water and oxygen;

step □: to bromide and bis(pinacolato)diboron of D (the molar ratio of bromide to bis(pinacolato)diboron of D is 1:0.5) in a solvent of toluene is added a suitable amount of an aqueous solution of K₂CO₃ (2 mol/L), and the resultant mixture is heated with reflux for 1 to 7 days under argon gas protection in the presence of Pd(PPh₃)₄ (0.1-20 mol %) as a catalyst; and step □: the resultant mixture is reacted with excessive receptor terminal monomer in a solvent of trichloromethane for 1 to 7 days at room temperature, under argon gas protection in the presence of triethylamine (0.1-20 mol %) as a catalyst.

In some embodiments, the process for preparing the donor-receptor type oligothiophene compound comprising a receptor terminal of general formula (5) is outlined as follows.

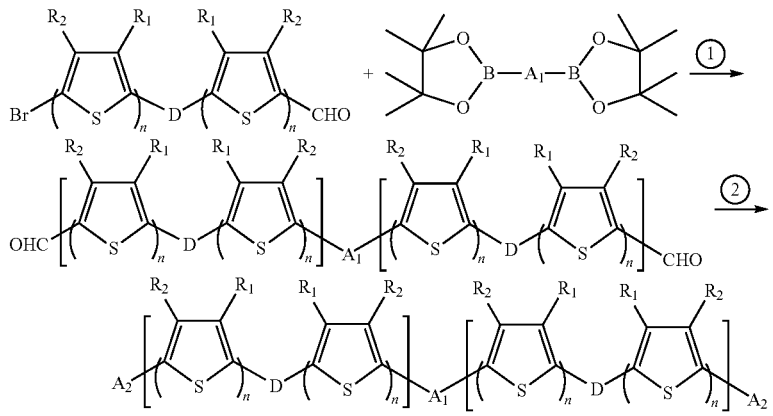

wherein step □: to bromide and bis(pinacolato)diboron monomer of A (the molar ratio of bromide to bis(pinacolato)diboron monomer of A is 1:0.5) in a solvent of toluene is added a suitable amount of an aqueous solution of K₂CO₃ (2 mol/L), and the resultant mixture is heated with reflux for 1 to 7 days under argon gas protection in the presence of Pd(PPh$_3$)$_4$ (0.1-20 mol %) as a catalyst; and step □: the resultant mixture is reacted with excessive receptor terminal monomer in a solvent of trichloromethane for 1 to 7 days at room temperature, under argon gas protection in the presence of triethylamine (0.1-20 mol %) as a catalyst.

In some embodiments, the process for preparing the donor-receptor type oligothiophene compound comprising a receptor terminal of general formula (6) is outlined as follows.

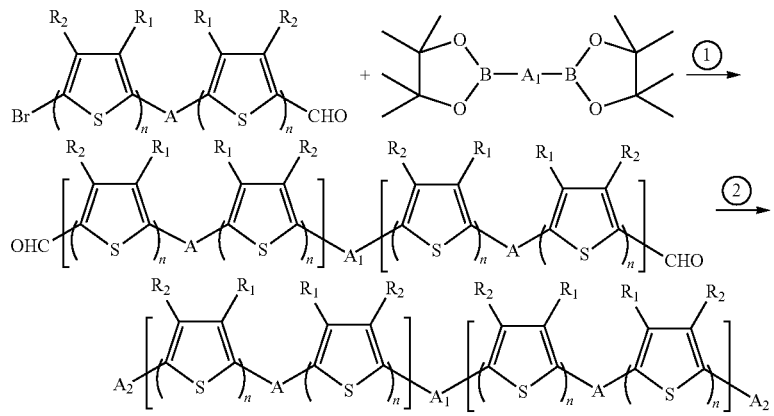

in the above formulae, A and A$_1$ may be identical or different, wherein step □: to bromide and bis(pinacolato)diboron monomer of A (the molar ratio of bromide to bis(pinacolato) diboron monomer of A is 1:0.5) in a solvent of toluene is added a suitable amount of an aqueous solution of K$_2$CO$_3$ (2 mol/L), and the resultant mixture is heated with reflux for 1 to 7 days under argon gas protection in the presence of Pd(PPh$_3$)$_4$ (0.1-20 mol %) as a catalyst; and step □: the resultant mixture is reacted with excessive receptor terminal monomer in a solvent of trichloromethane for 1 to 7 days at room temperature, under argon gas protection in the presence of triethylamine (0.1-20 mol %) as a catalyst.

In another aspect, the present application relates to a process for preparing a donor-receptor type oligothiophene compound of general formulae (1) to (6), comprising carrying out a Knoevenagel condensation reaction of a donor bridged oligothiophene comprising a small molecule dye terminal with an organic small molecule dye monomer through a bisaldehyde group donor bridged oligothiophene in the presence of a solvent and a catalyst to obtain the compound.

In some embodiments, the catalyst used in the process for preparing the donor-receptor type oligothiophene compound of general formulae (1) to (6) is an acidic catalyst. In some embodiments, the catalyst used in the process for preparing the donor-receptor type oligothiophene compound of general formulae (1) to (6) is a weak acidic catalyst.

Exemplary examples of weak acidic catalysts that can be used in the process for preparing the donor-receptor type oligothiophene compound of general formulae (1) to (6) in the present application include, but are not limited to, ammonium acetate, ammonium propionate and ammonium butyrate.

In some embodiments, the catalyst used in the process for preparing the donor-receptor type oligothiophene compound of general formulae (1) to (6) is ammonium acetate.

In some embodiments, the solvent used in the process for preparing the donor-receptor type oligothiophene compound of general formulae (1) to (6) is an acidic solution. In some embodiments, the solvent used in the process for preparing the donor-receptor type oligothiophene compound of general formulae (1) to (6) is a weak acidic solution.

Exemplary examples of weak acidic solutions that can be used in the process for preparing the donor-receptor type oligothiophene compound of general formulae (1) to (6) in the present application include, but are not limited to, acetic acid, propionic acid and butyric acid.

In some embodiments, the solvent used in the process for preparing the donor-receptor type oligothiophene compound of general formulae (1) to (6) is acetic acid.

In some embodiments, the amount of the catalyst used in the process for preparing the donor-receptor type oligothiophene compound of general formulae (1) to (6) is excessive. In some embodiments, the amount of the catalyst used in the process for preparing the donor-receptor type oligothiophene compound of general formulae (1) to (6) is 10-30 mol %. In some embodiments, the amount of the catalyst used in the process for preparing the donor-receptor type oligothiophene compound of general formulae (1) to (6) is 20 mol %.

In some embodiments, the process for preparing the donor-receptor type oligothiophene compound of general formula (1) is outlined as follows.

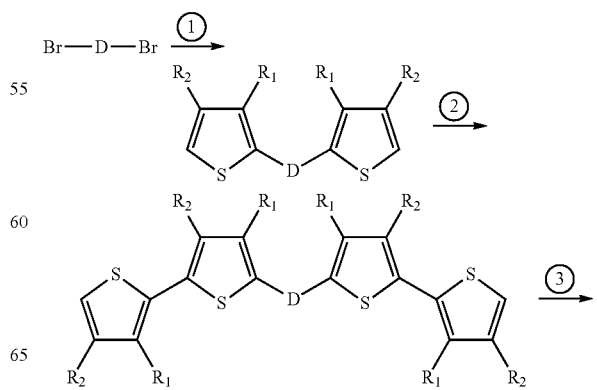

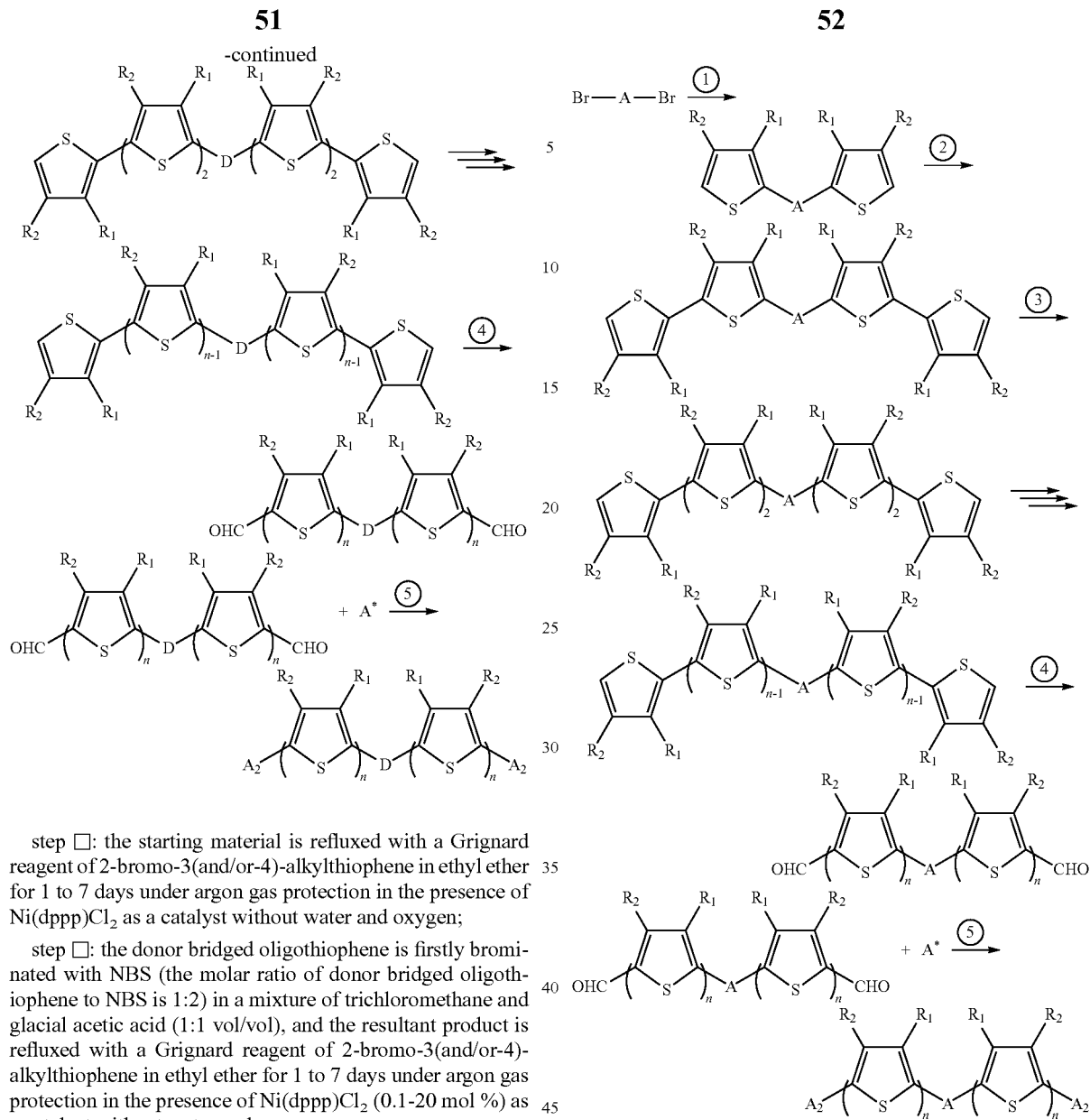

step ☐: the starting material is refluxed with a Grignard reagent of 2-bromo-3(and/or-4)-alkylthiophene in ethyl ether for 1 to 7 days under argon gas protection in the presence of Ni(dppp)Cl$_2$ as a catalyst without water and oxygen;

step ☐: the donor bridged oligothiophene is firstly brominated with NBS (the molar ratio of donor bridged oligothiophene to NBS is 1:2) in a mixture of trichloromethane and glacial acetic acid (1:1 vol/vol), and the resultant product is refluxed with a Grignard reagent of 2-bromo-3(and/or-4)-alkylthiophene in ethyl ether for 1 to 7 days under argon gas protection in the presence of Ni(dppp)Cl$_2$ (0.1-20 mol %) as a catalyst without water and oxygen;

step ☐: the donor bridged oligothiophene is firstly brominated with NBS (the molar ratio of donor bridged oligothiophene to NBS is 1:2) in a mixture of trichloromethane and glacial acetic acid (1:1 vol/vol), and the resultant product is refluxed with a Grignard reagent of 2-bromo-3(and/or-4)-alkylthiophene in ethyl ether for 1 to 7 days under argon gas protection in the presence of Ni(dppp)Cl$_2$ (0.1-20 mol %) as a catalyst without water and oxygen;

step ☐: POCl$_3$ is firstly reacted with DMF in an ice bath to give a Vilsmeier reagent, the Vilsmeier reagent in an excessive amount is added dropwise into the donor bridged oligothiophene in 1,2-dichloroethane, and the resultant mixture is heated under reflux for 1 to 7 days; and step ☐: the resultant mixture and excessive receptor terminal monomer A* in a solvent of acetic acid is heated and refluxed for 24 h in the presence of ammonium acetate (20 mol %) as a catalyst.

In some embodiments, the process for preparing the donor-receptor type oligothiophene compound of general formula (2) is outlined as follows.

wherein step ☐: the starting material is refluxed with 2-(trimethylstannyl)-3(and/or-4)-alkylthiophene in toluene for 1-7 days under argon gas protection in the presence of Pd(PPh$_3$)$_4$ (0.1-20 mol %) as a catalyst without water and oxygen;

step ☐: the receptor bridged oligothiophene is firstly brominated with NBS (the molar ratio of receptor bridged oligothiophene to NBS is 1:2) in a mixture of trichloromethane and glacial acetic acid (1:1 vol/vol), and the resultant product is refluxed with 2-(trimethylstannyl)-3(and/or-4)-alkylthiophene or 2-(tributylstannyl)-3(and/or-4)-alkylthiophene in toluene for 1 to 7 days under argon gas protection in the presence of Pd(PPh$_3$)$_4$ (0.1-20 mol %) as a catalyst without water and oxygen;

step ☐: the receptor bridged oligothiophene is firstly brominated with NBS (the molar ratio of receptor bridged oligothiophene to NBS is 1:2) in a mixture of trichloromethane and glacial acetic acid (1:1 vol/vol), and the resultant product is refluxed with 2-(trimethylstannyl)-3(and/or-4)-alkylthiophene or 2-(tributylstannyl)-3(and/or-4)-alkylthiophene in toluene for 1 to 7 days under argon gas protection in the presence of Pd(PPh$_3$)$_4$ (0.1-20 mol %) as a catalyst without water and oxygen;

step ☐: POCl$_3$ is firstly reacted with DMF in an ice bath to give a Vilsmeier reagent, the Vilsmeier reagent in an excessive amount is added dropwise into the receptor bridged oligothiophene in 1,2-dichloroethane, and the resultant mixture is heated under reflux for 1 to 7 days; and step ☐: the resultant mixture and excessive receptor terminal monomer A* in a solvent of acetic acid is heated and refluxed for 24 h in the presence of ammonium acetate (20 mol %) as a catalyst.

In some embodiments, the process for preparing the donor-receptor type oligothiophene compound of general formula (3) is outlined as follows.

step ☐: the donor bridged oligothiophene is firstly brominated with NBS (the molar ratio of donor bridged oligothiophene to NBS is 1:1) in a mixture of trichloromethane and glacial acetic acid (1:1 vol/vol);

step ☐: a mixture of bromide and distannide monomer of D (the molar ratio of bromide to distannide monomer of D is 1:0.5) in a solvent of toluene is heated with reflux for 1-7 days under argon gas protection in the presence of Pd(PPh$_3$)$_4$ (0.1-20 mol %) as a catalyst without water and oxygen;

step ☐: to bromide and bis(pinacolato)diboron of D (the molar ratio of bromide to bis(pinacolato)diboron of D is 1:0.5) in a solvent of toluene is added a suitable amount of an aqueous solution of K$_2$CO$_3$ (2 mol/L), and the resultant mixture is heated with reflux for 1 to 7 days under argon gas protection in the presence of Pd(PPh$_3$)$_4$ (0.1-20 mol %) as a catalyst; and

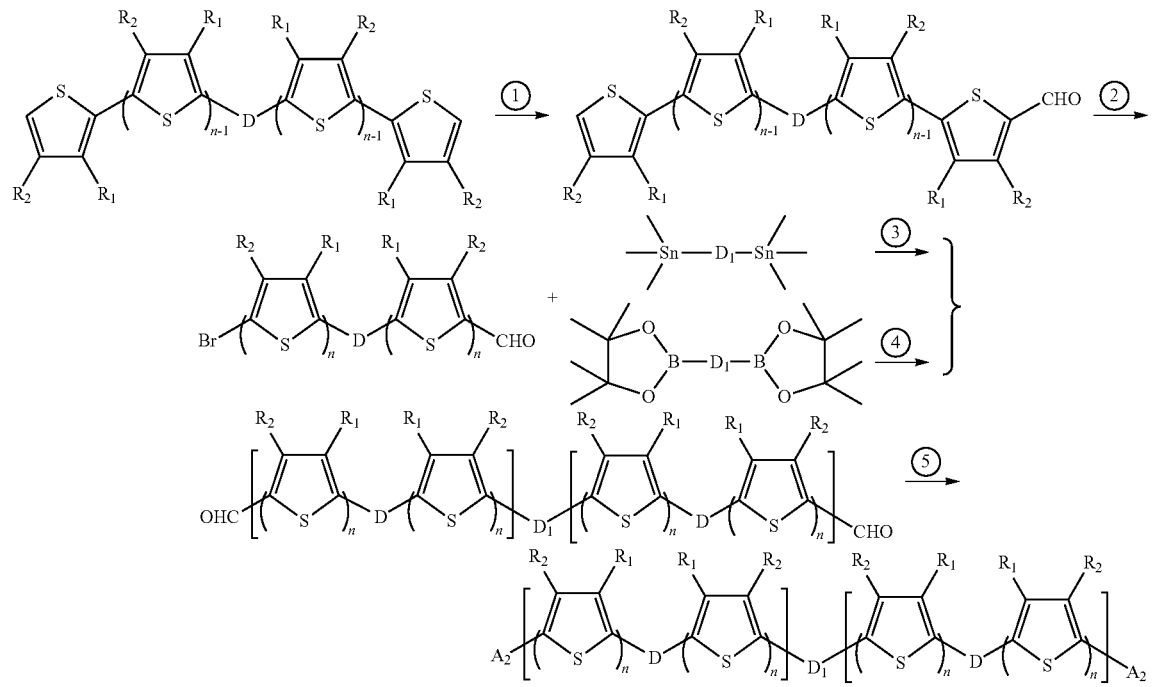

in the above formulae, D and D$_1$ may be identical or different, step ☐: POCl$_3$ is firstly reacted with DMF in an ice bath to give a Vilsmeier reagent, the Vilsmeier reagent is added dropwise into the donor bridged oligothiophene in 1,2-dichloroethane (the molar ratio of oligothiophene and Vilsmeier reagent is 1:0.5), and the resultant mixture is heated under reflux for 1 to 7 days;

step ☐: the resultant mixture and excessive receptor terminal monomer A* in a solvent of acetic acid is heated and refluxed for 24 h in the presence of ammonium acetate (20 mol %) as a catalyst.

In some embodiments, the process for preparing the donor-receptor type oligothiophene compound of general formula (4) is outlined as follows.

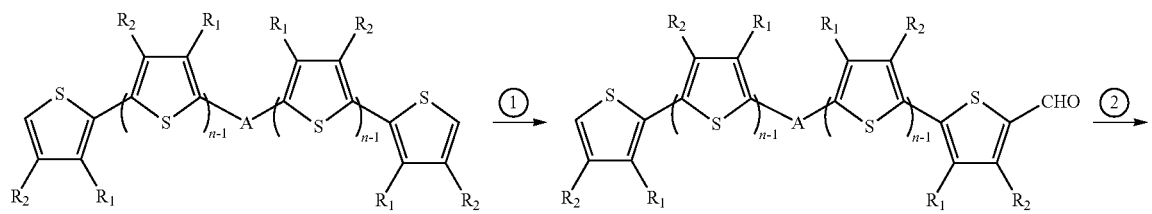

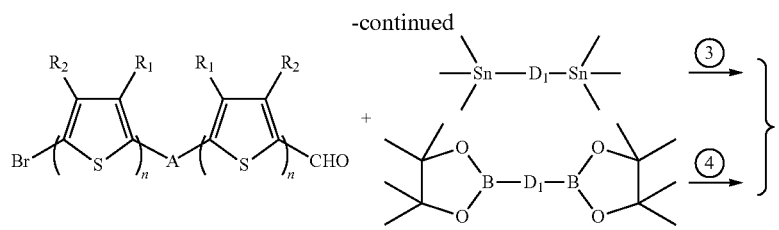

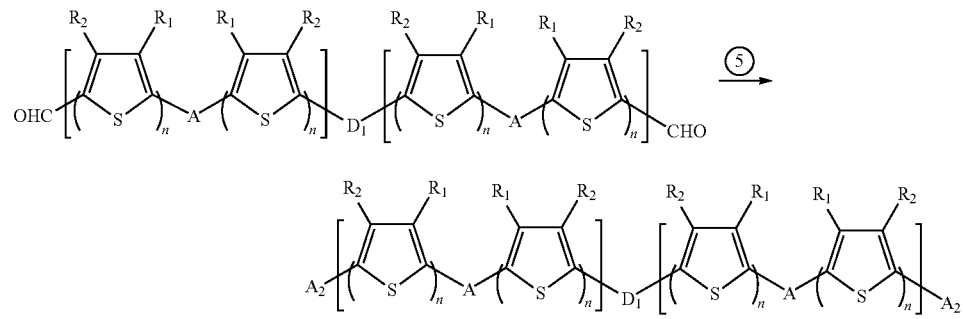

step □: POCl₃ is firstly reacted with DMF in an ice bath to give a Vilsmeier reagent, the Vilsmeier reagent is added dropwise into the receptor bridged oligothiophene in 1,2-dichloroethane (the molar ratio of receptor bridged oligothiophene and Vilsmeier reagent is 1:0.5), and the resultant mixture is heated under reflux for 1 to 7 days;

step □: the receptor bridged oligothiophene is firstly brominated with NBS (the molar ratio of donor bridged oligothiophene to NBS is 1:1) in a mixture of trichloromethane and glacial acetic acid (1:1 vol/vol);

step □: a mixture of bromide and distannide monomer of D (the molar ratio of bromide to distannide monomer of D is 1:0.5) in a solvent of toluene is heated with reflux for 1 to 7 days under argon gas protection in the presence of Pd(PPh₃)₄ (0.1-20 mol %) as a catalyst without water and oxygen;

step □: to bromide and bis(pinacolato)diboron of D (the molar ratio of bromide to bis(pinacolato)diboron of D is 1:0.5) in a solvent of toluene is added a suitable amount of an aqueous solution of K₂CO₃ (2 mol/L), and the resultant mixture is heated with reflux for 1 to 7 days under argon gas protection in the presence of Pd(PPh₃)₄ (0.1-20 mol %) as a catalyst; and step □: the resultant mixture and excessive receptor terminal monomer A* in a solvent of acetic acid is heated and refluxed for 24 h in the presence of ammonium acetate (20 mol %) as a catalyst.

In some embodiments, the process for preparing the donor-receptor type oligothiophene compound of general formula (5) is outlined as follows.

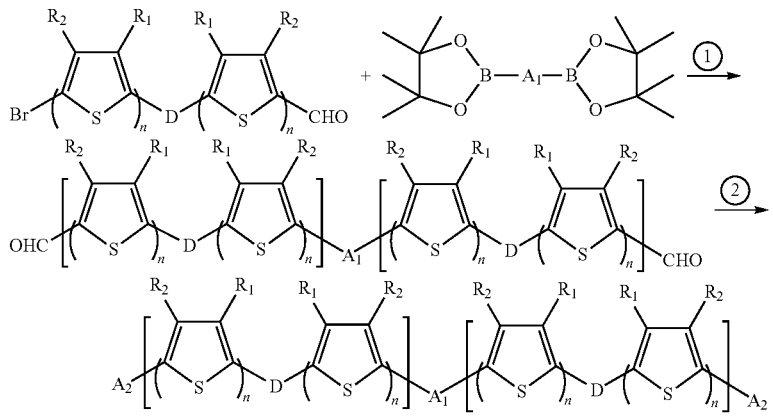

step □: to bromide and bis(pinacolato)diboron monomer of A₁ (the molar ratio of bromide to bis(pinacolato)diboron monomer of A₁ is 1:0.5) in a solvent of toluene is added a suitable amount of an aqueous solution of K₂CO₃ (2 mol/L), and the resultant mixture is heated with reflux for 1 to 7 days under argon gas protection in the presence of Pd(PPh₃)₄ (0.1-20 mol %) as a catalyst; and step □: the resultant mixture and excessive receptor terminal monomer A* in a solvent of acetic acid is heated and refluxed for 24 h in the presence of ammonium acetate (20 mol %) as a catalyst.

In some embodiments, the process for preparing the donor-receptor type oligothiophene compound of general formula (6) is outlined as follows.

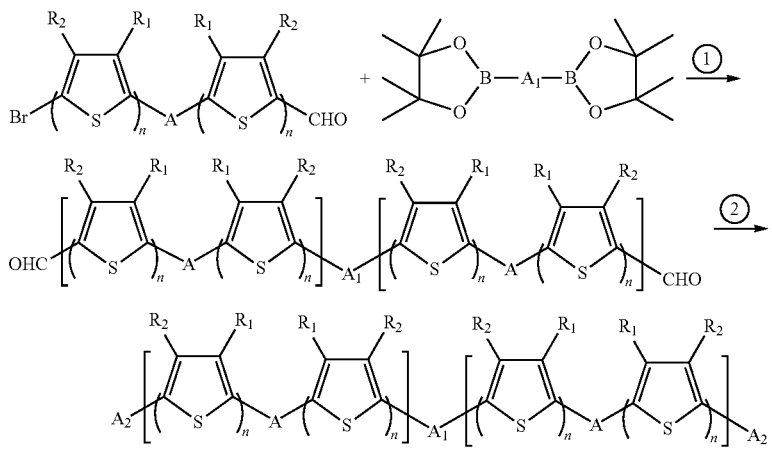

in the above formulae, A and $A_1$ may be identical or different, step ☐: to bromide and bis(pinacolato)diboron monomer of A (the molar ratio of bromide to bis(pinacolato)diboron monomer of A is 1:0.5) in a solvent of toluene is added a suitable amount of an aqueous solution of $K_2CO_3$ (2 mol/L), and the resultant mixture is heated with reflux for 1 to 7 days under argon gas protection in the presence of $Pd(PPh_3)_4$ (0.1-20 mol %) as a catalyst; and step ☐: the resultant mixture and excessive receptor terminal monomer A* in a solvent of acetic acid is heated and refluxed for 24 h in the presence of ammonium acetate (20 mol %) as a catalyst.

In yet another aspect, the present application relates to use of a donor-receptor type oligothiophene compound comprising a receptor terminal of general formulae (1) to (6) in the manufacture of a field effect transistor.

In still another aspect, the present application relates to use of a donor-receptor type oligothiophene compound comprising a receptor terminal of general formulae (1) to (6) in the manufacture of a photovoltaic device.

In some embodiments, the photovoltaic device manufactured with the donor-receptor type oligothiophene compound comprising a receptor terminal of general formulae (1) to (6) is a solar cell device.

In some embodiments, the photovoltaic device manufactured with the donor-receptor type oligothiophene compound comprising a receptor terminal of general formulae (1) to (6) is a photoactive layer in a solar cell device.

In yet another aspect, the present application relates to a triode device comprising an active layer having a donor-receptor type oligothiophene compound of general formulae (1) to (6).

In still another aspect, the present application relates to a photovoltaic device comprising an active layer having a donor-receptor type oligothiophene compound of general formulae (1) to (6).

In some embodiments, the solar cell device comprises a photoactive layer having a receptor-donor type oligothiophene compound of general formulae (1) to (6).

In yet another aspect, the present application relates to a process for manufacturing a field effect transistor, comprising providing a donor-receptor type oligothiophene compound comprising a receptor terminal of general formulae (1) to (6).

In still another aspect, the present application relates to a process for manufacturing a photovoltaic device, comprising providing a donor-receptor type oligothiophene compound comprising a receptor terminal of general formulae (1) to (6).

In other aspects, the present application relates to a compound selected from the group consisting of:

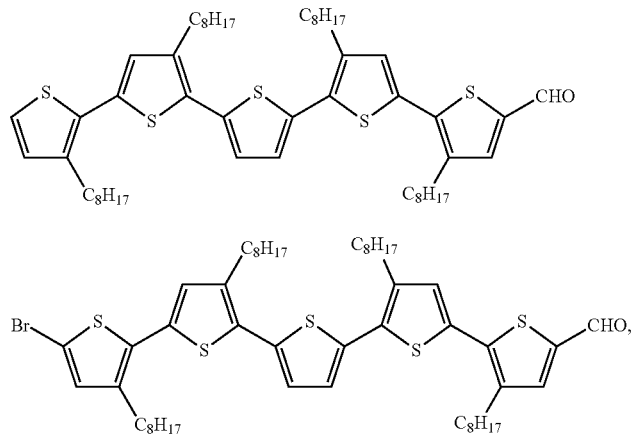

-continued
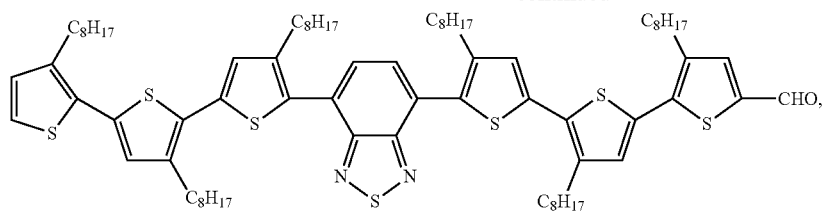
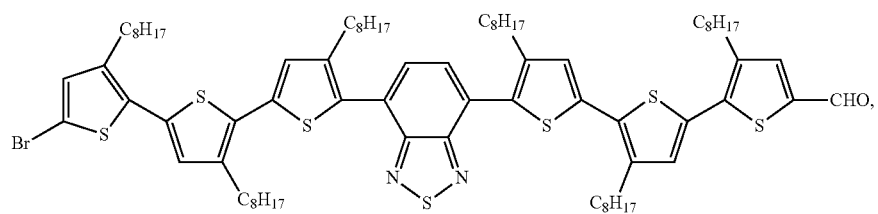
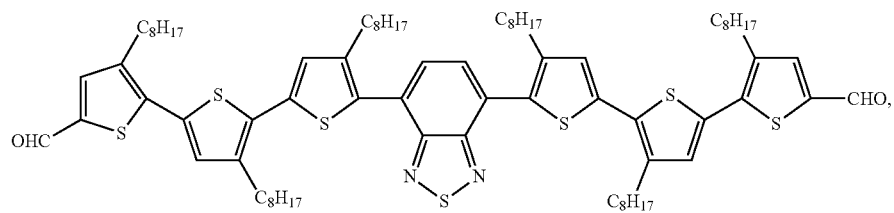
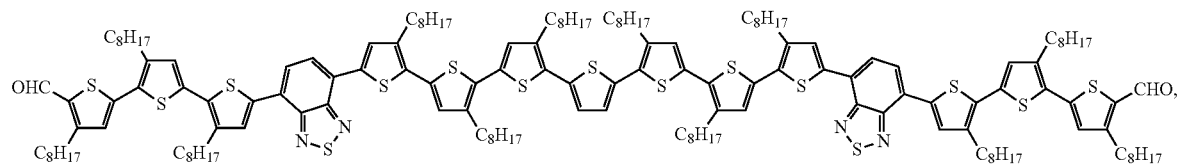
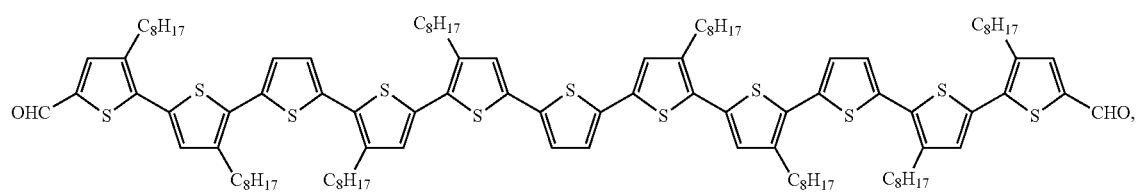
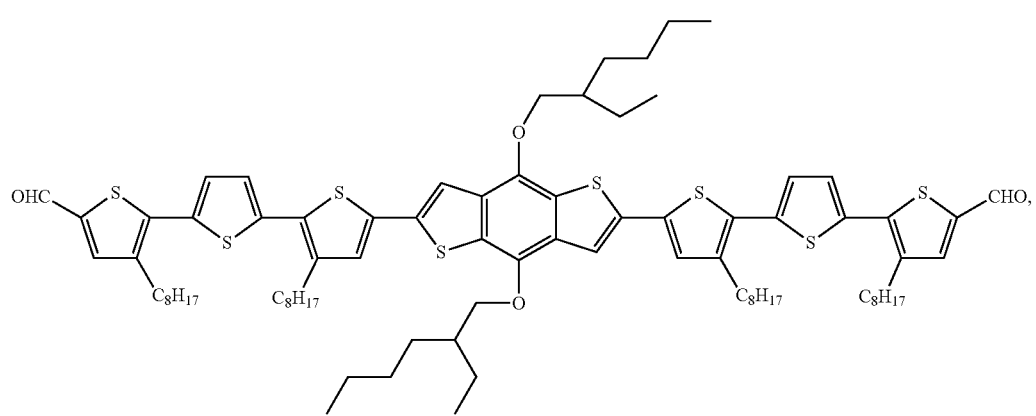

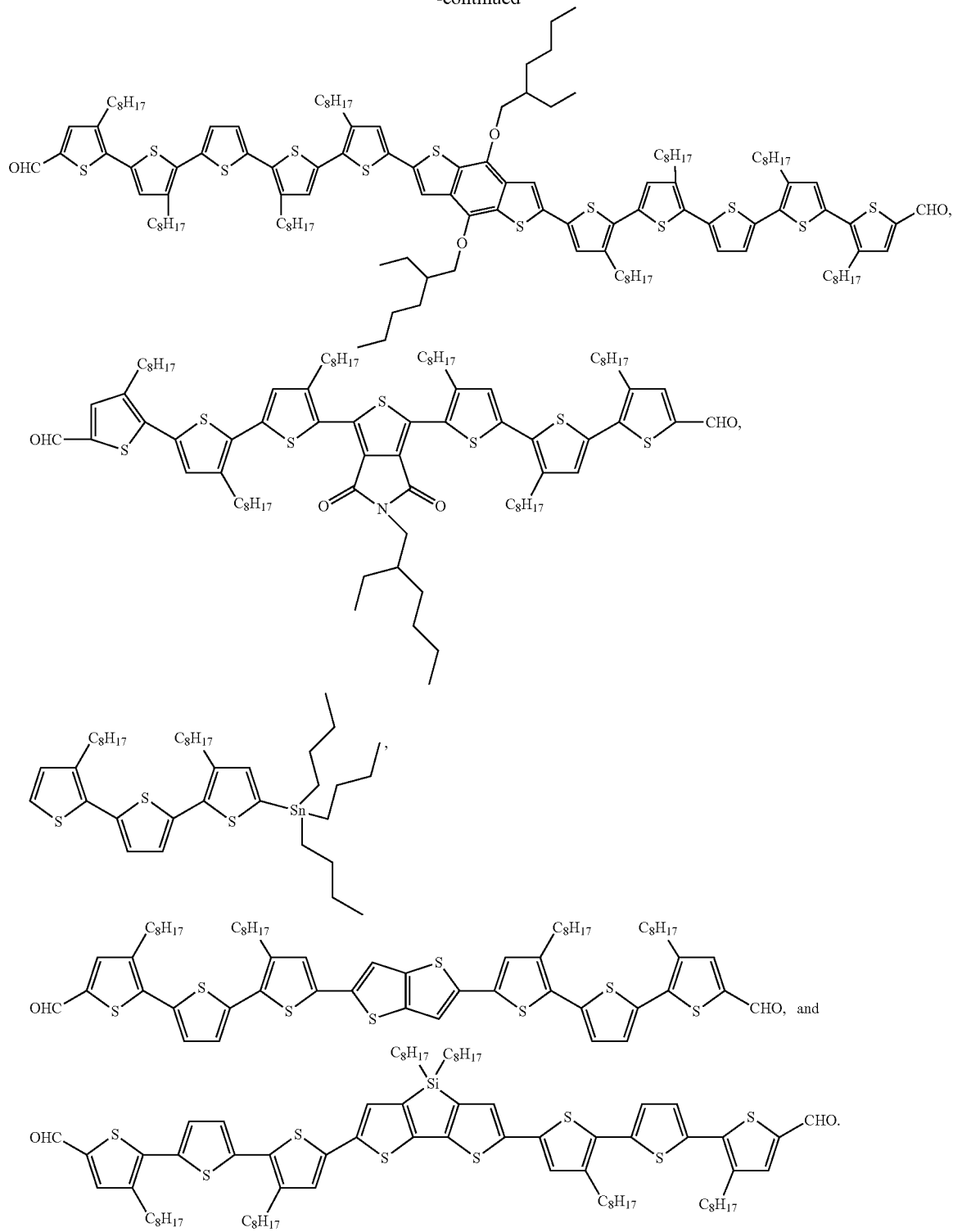

In the donor-receptor type oligothiophene photovoltaic materials comprising a receptor terminal of the present application, the donor-receptor type oligothiophene photovoltaic materials of the present application possess higher hole mobility due to higher hole mobility of oligothiophene.

The donor-receptor type oligothiophene photovoltaic materials comprising a receptor terminal of the present application possess the combined advantages of polymers and common conjugated small molecules, i.e. possess advantages such as accurate molecular weight, controlled structure, easiness to purify comparing with common polymers, and possess better solubility, capability of forming thin films, advantage to the manufacture of field effect transistors and photovoltaic device including solar cell devices comparing with common conjugated small molecules.

In the donor-receptor type oligothiophene compounds comprising organic small molecule dye terminals of the present application, such donor-receptor type oligothiophene compounds of the present application possess higher hole mobility and molar absorption coefficient due to higher hole mobility of oligothiophene and high electron-withdrawing and molar absorption coefficient of organic small molecule dyes.

The donor-receptor type oligothiophene compounds comprising organic small molecule dye terminals of the present application possess the combined advantages of polymers and conjugated small molecules, i.e. possess advantages such as accurate molecular weight, controlled structure, easiness to purify comparing with common polymers, and possess better solubility, possibility of salvation, capability of forming thin films, advantage to the manufacture of high performance field effect transistors and photovoltaic devices including solar cell devices comparing with common conjugated small molecules.

Organic thin film solar cells manufactured with the donor-receptor type oligothiophene compounds comprising organic small molecule dye terminals of the present application possess properties of high molar absorption coefficient of dye-sensitized cells and retain properties of forming flexible thin layers of organic solar cells.

Hereafter, detailed illustration will be carried out through the following examples referring to accompanying figures for better understanding of the various aspects and advantages of the present invention. However, it will be appreciated that the following examples are non-limiting and only for illustrating some embodiments of the present invention.

EXAMPLES

Example 1

Synthesis of Oligothiophene Precursors

1) Synthesis of 2-bromo-3-octylthiophene

To a 250 mL of two-ported flask filled with 3-octylthiophene (10.00 g, 50.93 mmol) was added 60 mL of DMF. A solution of NBS (9.26 g, 52.03 mmol) in 60 mL of DMF was added dropwise in an iced saline bath. After addition was completed, the mixture was warmed to the room temperature and then stirred at this temperature overnight. The reaction was stopped and the resultant product was poured into 200 mL of water. The mixture was extracted with dichloromethane (60 mL×4). The organic phase was washed with aqueous potassium hydroxide solution (2 M, 100 mL), saturated saline (100 mL) and water (100 mL×2), successively. The organic phase was dried over anhydrous sodium sulfate. The solvent was removed under reduced pressure. The resultant product was separated with chromatographic column, in which eluant was petroleum ether, to give a liquid as oil (12.60 g, yield: 89%).

The structure of product was indicated as follows:

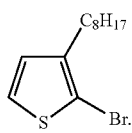

2) Synthesis of 3,3"-dioctyl-2,2':5',2"-trithiophene (3T)

Under argon gas protection, to a 100 mL of two-ported flask filled with magnesium chips (704 mg, 28.96 mmol) was added 20 mL of ethyl ether and was slowly added dropwise a mixed solution of 2-bromo-3-octylthiophene (4.00 g, 14.56 mmol), 1,2-dibromoethane (1.37 g, 7.28 mmol) and ethyl ether (20 mL). After addition was completed, the mixture was heated under reflux for 4 h and cooled to room temperature. The resultant Grignard reagent was slowly added dropwise to a mixed solution of Ni(dppp)Cl$_2$ (177 mg, 0.326 mmol), 2,5-dibromothiophene (1.40 g, 5.56 mmol) and 25 mL of ethyl ether (25 mL). After addition was completed, the mixture was heated under reflux for 18 h. After cooling to room temperature, 20 mL of diluted hydrochloric acid (2 M) was added to the mixture. The resultant mixture was poured into 200 mL of water and extracted with dichloromethane (100 mL×3). The organic phase was washed with aqueous sodium carbonate solution (2 M, 100 mL), saturated saline (100 mL) and water (100 mL), successively. The organic phase was dried over anhydrous sodium sulfate. After the solvent was removed under reduced pressure, the resultant product was separated with chromatographic column, in which petroleum ether was eluant, to give a liquid as pale yellow oil (2.30 g, yield: 84%).

The structure of product was indicated as follows:

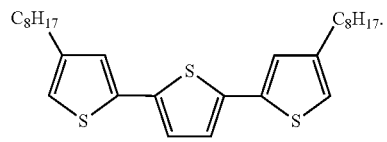

3) Synthesis of 5-tributylstannyl-3,3"-dioctyl-2,2':5', 2"-trithiophene (BS3T)

Under argon gas protection, to a 250 mL of three-ported flask filled with trithiophene (3.65 g, 7.72 mmol) was added 100 mL of THF. The mixture was cooled to −78° C. A solution of n-BuLi in n-hexane (3.3 ml, 2.4 M, 2.92 mmol) was added in the mixture. The resultant mixture was warmed to −40° C. and reacted for 1 h. After cooling to −78° C., to the product was added tributylstannyl chloride (3.02 g, 9.26 mmol). The mixture was stirred at room temperature overnight. The reactants were poured into 100 mL of water and extracted with ethyl acetate (30 mL×3). The organic phase was washed with water (100 mL), saturated saline (100 mL) and water (100 mL), successively. The organic phase was dried over anhydrous sodium sulfate. The solvent was removed under reduced pressure to give a liquid as orange yellow oil (4.83 g, yield: 82%).

The structure of product was indicated as follows:

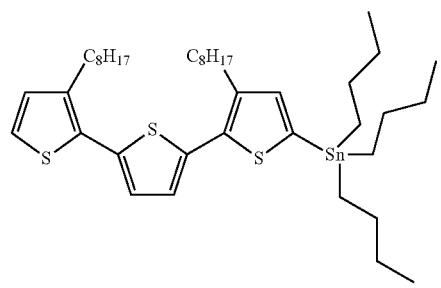

4) Synthesis of 5,5"-dibromo-3,3"-dioctyl-2,2':5',2"-trithiophene (3TBr₂)

To a 250 mL of two-ported flask filled with trithiophene 1 (1.20 g, 2.54 mmol) were added 30 mL of chloroform and 30 mL of glacial acetic acid. The mixture was cooled to 0° C. NBS (0.96 g, 5.39 mmol) was added in batch in about 20 min. After stirring at room temperature for 3 h, the reactants were poured into 100 mL of water and extracted with dichloromethane (100 mL×3). The organic phase was washed with aqueous sodium carbonate solution (2 M, 100 mL), saturated saline (100 mL) and water (100 mL), successively. The organic phase was dried over anhydrous sodium sulfate. After the solvent was removed under reduced pressure, the resultant product was separated with chromatographic column, in which petroleum ether was eluant, to give a liquid as yellow oil (1.60 g, yield: 100%).

The structure of the liquid was indicated as follows:

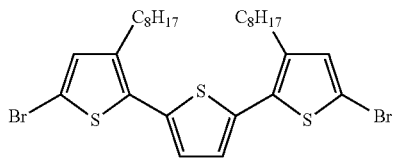

5) Synthesis of 3,3',3''',3''''-tetraoctyl-2,5':2',5'':2'',2''':5''',2''''-pentathiophene (5T)

Under argon gas protection and at room temperature, to a 100 mL of two-ported flask filled with magnesium powders (0.36 g, 14.48 mmol) was added dropwise a mixed solution of 2-bromo-3-octylthiophene (2.00 g, 7.28 mmol), 1,2-dibromoethane (0.34 g, 1.82 mmol) and ethyl ether (20 mL). After addition was completed, the mixture was heated under reflux for 4 h. Under argon gas protection, the resultant Grignard reagent was added dropwise to a mixed solution of dibromotrithiophene 2 (1.54 g, 2.44 mmol), Ni(dppp)Cl₂ (90 mg, 0.17 mmol) and ethyl ether (20 mL) in about half hour. The mixture was heated under reflux for 20 h and cooled to room temperature. To the mixture was added diluted hydrochloric acid (20 mL, 1 M) while stirring for 5 min. The reaction solution was poured into 100 mL of water and extracted with dichloromethane (100 mL×3). The organic phase was washed with water (100 mL), saturated saline (100 mL) and water (100 mL), successively. The organic phase was dried over anhydrous sodium sulfate. After the solvent was removed under reduced pressure, the resultant product was separated with chromatographic column, in which petroleum ether was eluant, to give a liquid as golden yellow oil (1.75 g, yield 83%).

The structure of product was indicated as follows:

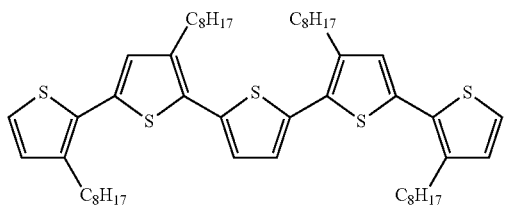

6) Synthesis of 5,5''''-dibromo-3,3',3'''3''''-tetraoctyl-2,5':2',5'':2'',2''':5''',2''''-pentathiophene (5TBr₂)

To a 250 mL of two-ported flask filled with pentathiophene 3 (1.15 g, 1.33 mmol) were added 30 mL of chloroform and 30 mL of glacial acetic acid. The mixture was cooled to 0° C. NBS (0.50 g, 2.81 mmol) was added in batch in about 20 min. After stirring at room temperature for 3 h, the reactants were poured into 100 mL of water and extracted with dichloromethane (100 mL×3). The organic phase was washed with aqueous sodium carbonate solution (2 M, 100 mL), saturated saline (100 mL) and water (100 mL), successively. The organic phase was dried over anhydrous sodium sulfate. After the solvent was removed under reduced pressure, the resultant product was separated with chromatographic column, in which petroleum ether was eluant, to give a liquid as yellow oil (1.22 g, yield: 90%).

The structure of product was indicated as follows:

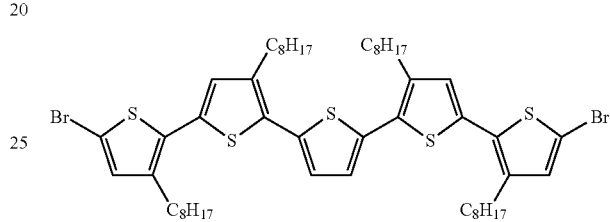

7) Synthesis of 3,3',3'',3''',3''',3''''''-hexaoctyl-2,5':2',5'':2'',2''':5''',2'''':5'''',2'''''-heptathiophene (7T)

At room temperature, to a 100 mL of two-ported flask filled with magnesium powders (0.18 g, 7.24 mmol) was added 15 mL of ethyl ether. A mixed solution of 2-bromo-3-octylthiophene (1.00 g, 3.64 mmol), 1,2-dibromoethane (0.17 g, 0.91 mmol) and ethyl ether (15 mL) was added. After addition was completed, the mixture was heated under reflux for 4 h. Under argon gas protection, the resultant Grignard reagent was added dropwise to a mixed solution of dibromopemtathiophene 4 (1.24 g, 1.22 mmol), Ni(dppp)Cl₂ (59 mg, 0.11 mmol) and ethyl ether (20 mL) in about half hour. The mixture was heated under reflux for 20 h and cooled to room temperature. To the mixture was added diluted hydrochloric acid (20 mL, 1 M) while stirring for 5 min. The reaction solution was poured into 100 mL of water and extracted with dichloromethane (100 mL×3). The organic phase was washed with water (100 mL), saturated saline (100 mL) and water (100 mL), successively. The organic phase was dried over anhydrous sodium sulfate. After the solvent was removed under reduced pressure, the resultant product was separated with chromatographic column, in which petroleum ether was eluant, to give a liquid as golden yellow oil (1.09 g, yield: 72%).

The structure of product was indicated as follows:

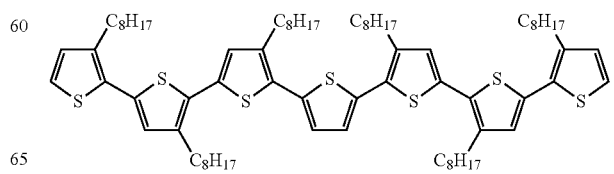

8) Synthesis of 5,5"-diformaldehyde-3,3"-dioctyl-2, 2':5',2"-trithiophene (3T(CHO)₂)

To DMF (3.00 mL, 38.70 mmol) was slowly added POCl₃ (0.71 mL, 7.74 mmol) at 0° C. The mixture was stirred for 10 min. Under argon gas protection, the resultant solution was added to a mixed solution of 3T (1.22 g, 2.58 mmol) and 1,2-dichloroethane (30 mL). The mixture was heated to 60° C. and reacted for 12 h, and then cooled to room temperature. The resultant product was poured into 200 mL of ice water, neutralized with sodium carbonate and extracted with dichloromethane (100 mL×3). The organic phase was washed with water (100 mL), saturated saline (100 mL) and water (100 mL), successively. The organic phase was dried over anhydrous sodium sulfate. After the solvent was removed under reduced pressure, the product was separated with chromatographic column, in which a mixed solution of petroleum ether and dichloromethane (1:1 vol/vol) was eluant, to give a coral solid (1.13 g, yield: 83%).

The structure of product was indicated as follows:

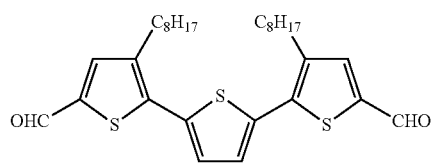

9) Synthesis of 5,5""-diformaldehyde-3,3',3,3""-tetraoctyl-2,5':2',5":2",2'":5"',2""-pentathiophene (5T(CHO)₂)

The process was similar to the synthesis of 3T(CHO)₂. A dark orange solid was obtained with yield of 85%.
The structure of product was indicated as follows:

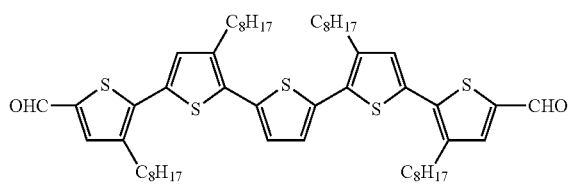

10) Synthesis of 5,5"""-diformaldehyde-3,3',3",3"",3"""',3""""'-hexaoctyl-2,5':2',5":2",2'":5"',2"":5"",2""": 5""",2"""'-heptathiophene (7T(CHO)₂)

The process was similar to the synthesis of 3T(CHO)₂. A brown solid (1.13 g) was obtained with yield of 81%.
The structure of product was indicated as follows:

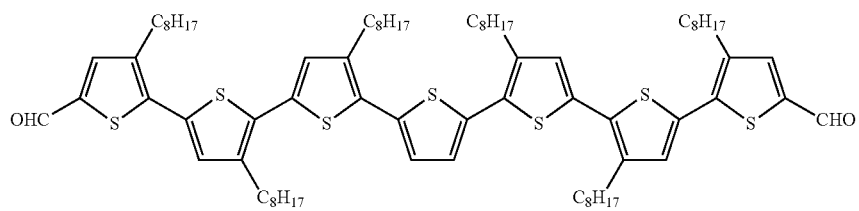

11) Synthesis of Compound TBT

To a 250 mL of two-ported flask were added 4,7-dibromobenzothiadiazole (6.00 g, 20.4 mmol), 2-tributylstannyl-4-octylthiophene (55 g, 113.3 mmol) and Pd(PPh₃)₂Cl₂ (320 mg, 0.46 mmol). Under argon gas protection, 120 mL of anhydrous freshly distilled tetrahydrofuran was added. The mixture was heated under reflux for 24 h. The reaction was stopped. The resultant product was poured into 100 mL of water and extracted with dichloromethane (100 mL×3). The organic phase was washed with water (100 mL) and dried over anhydrous sodium sulfate. After the solvent was removed under reduced pressure, the resultant product was separated with chromatographic column, in which petroleum ether was eluant, to give a red solid (8.8 g, yield: 82%).

The structure of product was indicated as follows:

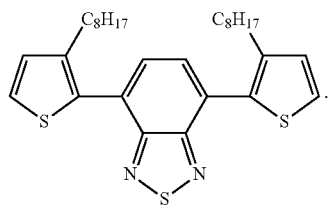

12) Synthesis of Compound BrTBTBr

To a 100 mL of two-ported flask were added the compound TBT (0.96 g, 1.83 mmol) and 60 mL of chloroform. NBS (0.65 g, 3.66 mmol) was added in batch in an ice saline bath. The mixture was reacted at this temperature for 1 h. The ice bath was removed. The resultant mixture was reacted at room temperature overnight. The resultant product was poured into 100 mL of water and extracted with dichloromethane (100 mL×3). The organic phase was washed with water (100 mL) and dried over anhydrous sodium sulfate. After the solvent was removed under reduced pressure, the resultant product was separated with chromatographic column, in which petroleum ether was eluant, to give a red solid (1.08 g, yield: 86%).

The structure of product was indicated as follows:

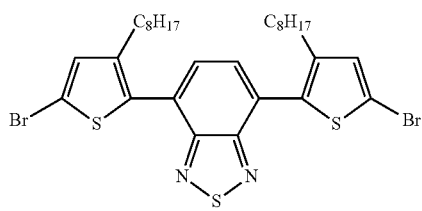

13) Synthesis of Compound 2TB2T

To a 100 mL of two-ported flask were added the compound BrTBTBr (1.02 g, 1.49 mmol), 2-tributylstannyl-4-octylthiophene (2.18 g, 4.48 mmol) and Pd(PPh₃)₂Cl₂ (105 mg, 0.15 mmol). Under argon gas protection, 65 mL of anhydrous freshly distilled tetrahydrofuran was added. The mixture was heated under reflux for 40 h. The reaction was stopped. The resultant product was poured into 100 mL of water and extracted with dichloromethane (100 mL×3). The organic phase was washed with water (100 mL) and dried over anhydrous sodium sulfate. After the solvent was removed under reduced pressure, the resultant product was separated with chromatographic column, in which petroleum ether was eluant, to give a purple solid (1.26 g, yield: 94%).

The structure of product was indicated as follows:

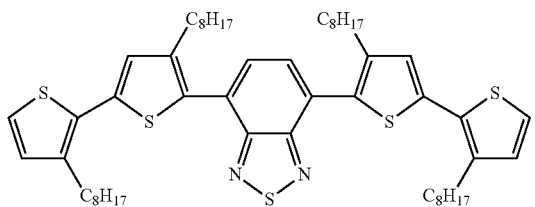

14) Synthesis of Compound Br2TB2TBr

To a 100 mL of two-ported flask were added the compound 2TB2T (0.86 g, 0.94 mmol) and 70 mL of chloroform.NBS (0.29 g, 1.61 mmol) was added in batch in an ice saline bath. The mixture was reacted at this temperature for 1 h. The ice bath was removed. The resultant mixture was reacted at room temperature overnight. The resultant product was poured into 100 mL of water and extracted with dichloromethane (100 mL×3). The organic phase was washed with water (100 mL) and dried over anhydrous sodium sulfate. After the solvent was removed under reduced pressure, the resultant product was separated with chromatographic column, in which petroleum ether was eluant, to give a red solid (0.79 g, yield: 46%).

The structure of product was indicated as follows:

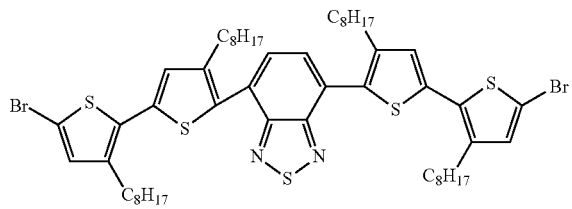

15) Synthesis of Compound 3TB3T

To a 250 mL of two-ported flask were added the compound Br2TB2TBr (130 mg, 0.12 mmol), 3-butylstannyl-4-octylthiophene (357 mg, 0.36 mmol) and Pd(PPh₃)₂Cl₂ (8.5 mg, 0.01 mmol). Under argon gas protection, 60 mL of anhydrous freshly distilled tetrahydrofuran was added. The mixture was heated under reflux for 40 h. The reaction was stopped. The resultant product was poured into 100 mL of water and extracted with dichloromethane (100 mL×3). The organic phase was washed with water (100 mL) and dried over anhydrous sodium sulfate. After the solvent was removed under reduced pressure, the resultant product was separated with chromatographic column, in which petroleum ether was eluant, to give a black solid (139 mg, yield: 89%).

The structure of product was indicated as follows:

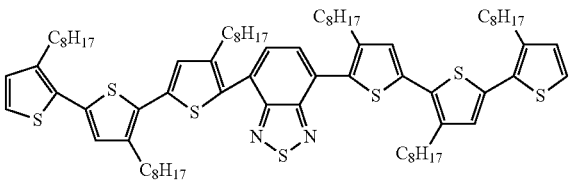

16) Synthesis of 5TCHO

To DMF (4.24 mL, 55.0 mmol) was slowly added POCl₃ (0.84 mL, 9.2 mmol) at 0° C. The mixture was stirred for 10 min. Under argon gas protection, one tenth of resultant solution was added dropwise to a mixed solution of 5T (0.79 g, 0.92 mmol) and 1,2-dichloroethane (30 mL). The mixture was heated to 70° C. and reacted for 24 h, and then cooled to room temperature. The resultant product was poured into 200 mL of iced water, neutralized with sodium carbonate and extracted with dichloromethane (100 mL×3). The organic phase was washed with water (100 mL), saturated saline (100 mL) and water (100 mL), successively. The organic phase was dried over anhydrous sodium sulfate. After the solvent was removed under reduced pressure, the product was separated with chromatographic column, in which a mixed solution of petroleum ether and dichloromethane (1:1 vol/vol) was eluant, to give a red solid (0.46 g, yield: 56%).

The structure of product was indicated as follows:

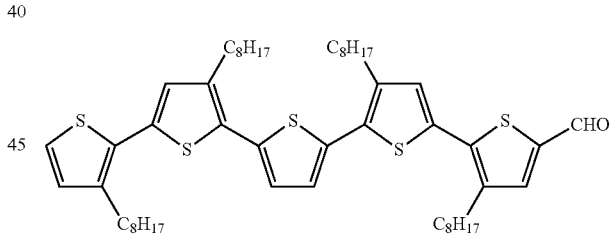

17) Synthesis of Br5TCHO

To a 100 mL of two-ported flask filled with 5TCHO (0.32 g, 0.36 mmol) were added 30 mL of chloroform and 30 mL of glacial acetic acid. NBS (64 mg, 0.36 mmol) was added in batch in about 20 min. After stirring at room temperature for 3 h, the reactants were poured into 100 mL of water and extracted with dichloromethane (100 mL×3). The organic phase was washed with aqueous sodium carbonate solution (2 M, 100 mL), saturated saline (100 mL) and water (100 mL), successively. The organic phase was dried over anhydrous sodium sulfate. After the solvent was removed under reduced pressure, the resultant product was separated with chromatographic column, in which petroleum ether was eluant, to give a red solid (0.31 g, yield: 89%).

The structure of product was indicated as follows:

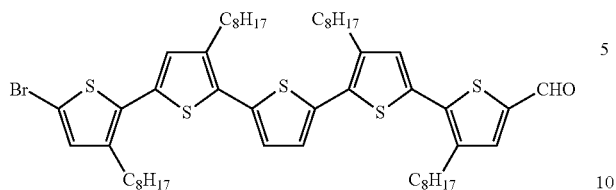

18) Synthesis of Compound 3TB3T(CHO)

The process was same as the synthesis of 5TCHO. A brown solid (1.08 g) was obtained with yield of 70%.

The structure of product was indicated as follows:

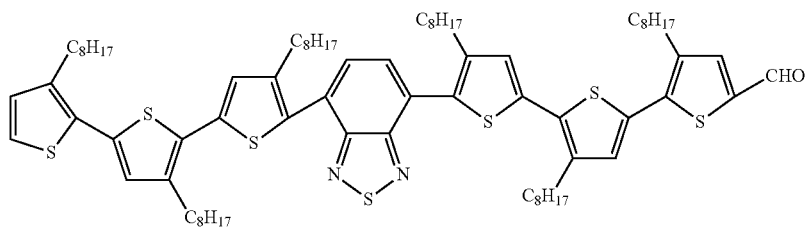

19) Synthesis of Compound Br3TB3T(CHO)

The process was same as the synthesis of Br5TCHO. A brown solid (0.82 g) was obtained with yield of 81%.

The structure of product was indicated as follows:

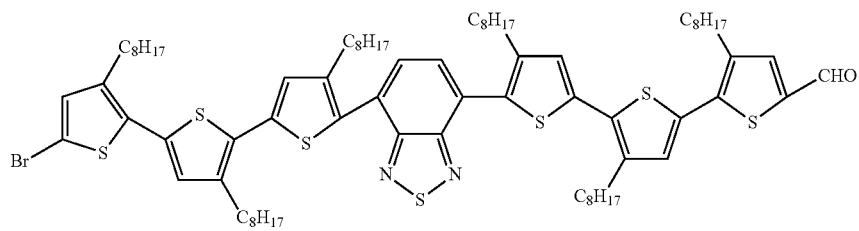

20) Synthesis of Compound D3TBT

Under argon gas protection, to a two-ported flask filled with p-dibromothiophene (0.40 g, 1.34 mmol), mono-tributylstannylthiophene (2.46 g, 3.23 mmol) and 40 mL of dry toluene was added triphenylphosphine palladium (0.078 g, 0.068 mmol). The mixture was refluxed at 110° C. overnight. The reaction solution was poured into 100 mL of water and extracted with dichloromethane (30 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane-petroleum ether was eluant, to give a orange red solid (0.60 g, yield: 41%).

The structure of product was indicated as follows:

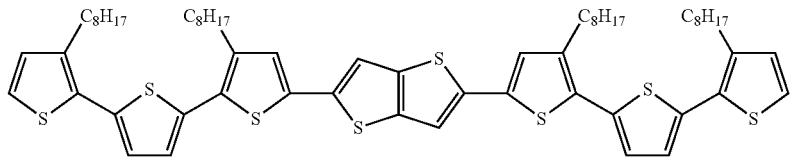

21) Synthesis of Compound 3T(TT)3T(CHO)₂

To DMF (3.19 mL, 41.25 mmol) was slowly added dropwise POCl₃ (0.76 mL, 8.32 mmol) at 0° C. The mixture was stirred for 10 min. Under argon gas protection, the resultant solution was added dropwise to a mixed solution of D3TBT (0.60 g, 0.55 mmol) and 1,2-dichloroethane (25 mL). The mixture was heated to 60° C. and reacted for 12 h, and then cooled to room temperature. The resultant product was poured into 100 mL of iced water, neutralized with sodium carbonate and extracted with dichloromethane (30 mL×3). The organic phase was washed with water (100 mL), saturated saline (100 mL) and water (100 mL), successively. The organic phase was dried over anhydrous sodium sulfate. After the solvent was removed under reduced pressure, the product was separated with chromatographic column, in which a mixed solution of petroleum ether and dichloromethane (1:1 vol/vol) was eluant, to give a black solid (0.40 g, yield: 63%).

The structure of product was indicated as follows:

(MALDI-FTICR): $C_{40}H_{50}N_2O_4S_3$ [M]⁺, calculated: 718.2933; found: 718.2937.

The structure of product was indicated as follows:

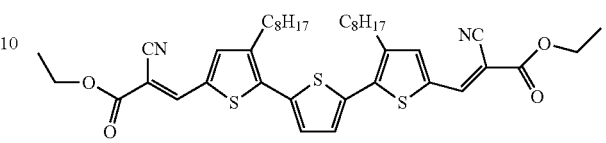

Example 3

The process was identical to Example 2. A blackish green solid was obtained with yield of 80%. ¹H NMR (400 MHz, CHCl₃): δ 8.15 (s, 2H), 7.49 (s, 2H), 7.13 (s, 2H), 7.09 (s, 2H), 4.29 (q, J=6.6 Hz, 4H), 2.74 (t, J=6.6 Hz, 8H), 1.61 (m, 8H), 1.32 (t, J=6.5 Hz, 6H), 1.21 (m, 40H), 0.80 (t, J=6.1 Hz, 12H). HRMS (MALDI-FTICR): $C_{64}H_{86}N_2O_4S_5$ [M]⁺, calculated: 1106.5191; found: 1106.5188.

The structure of product was indicated as follows:

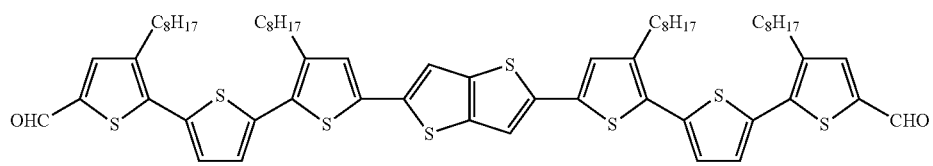

Example 2

Under argon gas protection, to a 100 mL of two-ported flask filled with diformyltrithiophene 3T(CHO)₂ (200 mg, 0.38 mmol) and 50 mL of chloroform were added three drops of triethylamine and 0.1 mL of ethyl cyanoacetate. The mixture was stirred and refluxed overnight under argon gas protection. After cooling to room temperature, the product was poured into 200 mL of water. The resultant mixture was stood, sucked and filtered. The solid was washed with ethanol. The resultant solid was separated with chromatographic column, in which dichloromethane was eluant, to give a brown solid (226 mg, yield: 83%). ¹H NMR (400 MHz, CHCl₃): δ 8.23 (s, 2H), 7.61 (s, 2H), 7.33 (s, 2H), 4.34-4.40 (q, J=7.0, 4H), 2.83 (t, J=7.5 Hz, 4H), 1.69 (m, 4H), 1.40 (t, J=7.0 Hz, 6H), 1.27 (m, 20H), 0.87 (t, J=6.1 Hz, 6H). HRMS

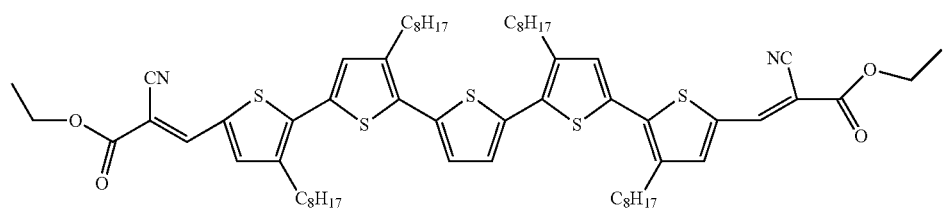

Example 4

The process was identical to Example 2. A blackish green solid (180 mg) was obtained with yield of 75%. ¹H NMR (400 MHz, CHCl₃): δ 8.14 (s, 2H), 7.49 (s, 2H), 7.12 (s, 2H), 7.05 (s, 2H), 6.96 (s, 2H), 4.27-4.31 (q, J=7.1 Hz, 4H), 2.75 (t, J=7.8 Hz, 12H), 1.58-1.68 (m, 12H), 1.32 (t, J=7.1 Hz, 6H), 1.21 (m, 60H), 0.80 (t, J=6.1 Hz, 18H). HRMS (MALDI-FTICR): $C_{88}H_{122}N_2O_4S_7$ [M]⁺, calculated: 1494.7450; found: 1494.7460.

The structure of product was indicated as follows:

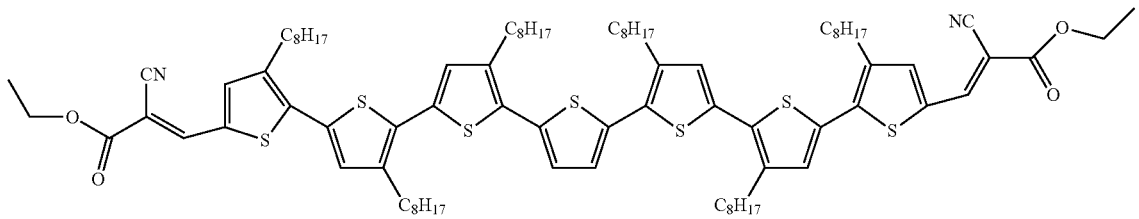

Example 5

The process was identical to Example 2 except that ethyl cyanoacetate was replaced with octyl cyanoacetate. The yield was 81%. $^1$H NMR (400 MHz, CHCl$_3$): δ 8.20 (s, 2H), 7.56 (s, 2H), 7.19 (s, 2H), 7.12 (s, 2H), 7.03 (s, 2H), 4.29 (t, J=6.7 Hz, 4H), 2.83 (m, 12H), 1.71 (m, 16H), 1.42-1.29 (m, 80H), 0.88 (t, J=5.9 Hz, 24H). MALDI-TOF MS (m/z): C$_{100}$H$_{146}$N$_2$O$_4$S$_7$ [M]$^+$, calculated: 1662.93; found: 1662.93.

The structure of product was indicated as follows:

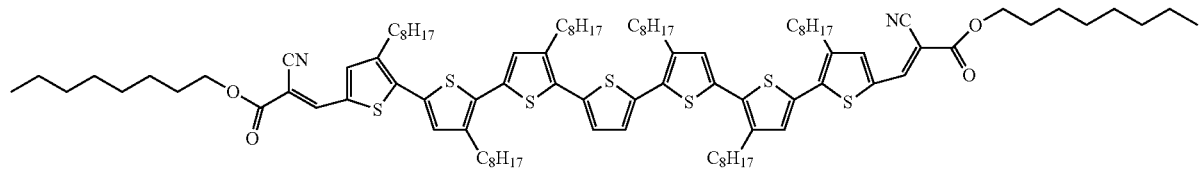

Example 6

The process was identical to Example 2 except that ethyl cyanoacetate was replaced with 2-ethylhexyl cyanoacetate. The yield was 78%. $^1$H NMR (400 MHz, CHCl$_3$): δ 8.20 (s, 2H), 7.57 (s, 2H), 7.19 (s, 2H), 7.12 (s, 2H), 7.03 (s, 2H), 4.22 (d, J=Hz, 4H), 2.83 (m, 12H), 1.71 (m, 14H), 1.42 (m, 16H), 1.31 (m, 60H), 0.94 (t, J=8.1 Hz, 12H), 0.88 (t, J=5.9 Hz, 18H). MALDI-TOF MS (m/z): C$_{100}$H$_{146}$N$_2$O$_4$S$_7$ [M]$^+$, calculated: 1662.93; found: 1662.93.

The structure of product was indicated as follows:

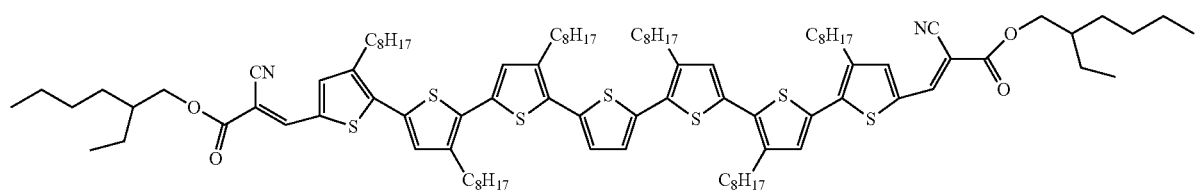

Example 7

To a 100 mL of two-ported flask were added 9 (0.16 g, 0.12 mmol) and 40 mL of chloroform. Under argon gas protection 0.1 mL of triethylamine was added and then 0.4 mL of malononitrile was added dropwise. The mixture was reacted at room temperature overnight. The resultant product was poured into 100 mL of water and extracted with dichloromethane (100 mL×3). The organic phase was washed with water (100 mL) and dried over anhydrous sodium sulfate. After the solvent was removed under reduced pressure, the product was separated with chromatographic column, in which a mixed solution of petroleum ether and dichloromethane (1:1 vol/vol) was eluant, to give a black solid (0.13 g, yield: 76%). $^1$H NMR (400 MHz, CHCl$_3$): δ 8.40 (s, 2H), 7.98 (s, 2H), 7.84 (s, 2H), 7.11 (d, J=7.7 Hz, 2H), 7.07 (br, 2H), 4.37 (q, J=7.0 Hz, 4H), 2.83 (m, 12H), 1.71 (m, 12H), 1.40 (t, J=7.0 Hz, 6H), 1.29 (m, 60H), 0.89 (br, 18H). MS (MALDI-TOF): C$_{86}$H$_{112}$N$_6$S$_7$ [M]$^+$, calculated: 1452.70; found: 1452.67.

The structure of product was indicated as follows:

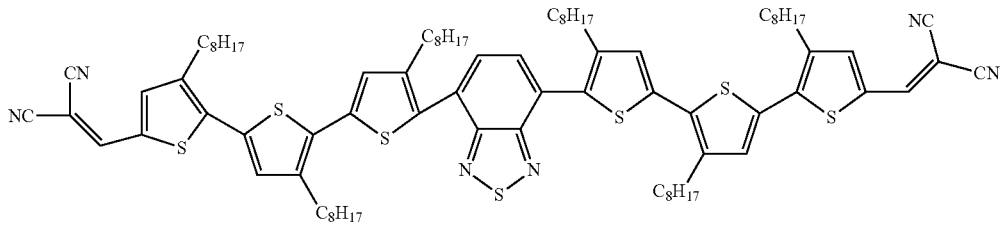

Example 8

Under argon gas protection, to a two-ported flask filled with diformylheptathiophene 7T(CHO)$_2$ (0.26 g, 0.20 mmol), 1,3-diethyl-2-thiobarbituric acid (0.20 g, 1.00 mmol) and 50 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane was eluant, to give a black solid (0.23 g, yield: 70%). MALDI-TOF MS (m/z): $C_{95}H_{134}N_4O_4S_8$ [M]$^+$, calculated: 1650.82; found: 1650.83. The structure of product was indicated as follows:

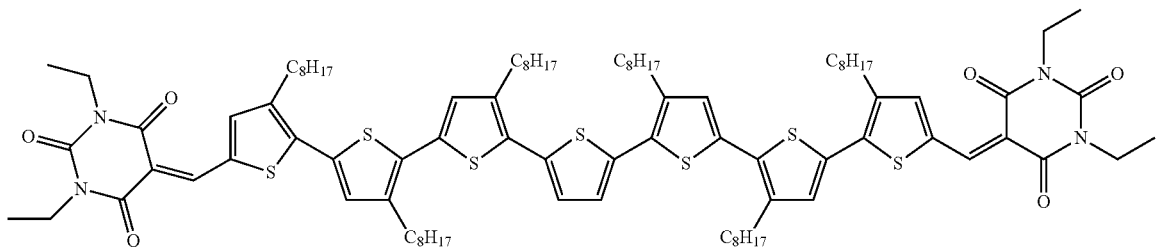

Example 9

Under argon gas protection, to a two-ported flask filled with diformylheptathiophene 7T(CHO)$_2$ (0.26 g, 0.20 mmol), diethyl malonate (0.16 g, 1.00 mmol) and 50 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane was eluant, to give a dark red solid (0.24 g, yield: 75%). MALDI-TOF MS (m/z): $C_{92}H_{132}O_8S_7$ [M]$^+$, calculated: 1588.80; found, 1588.81.

The structure of product was indicated as follows:

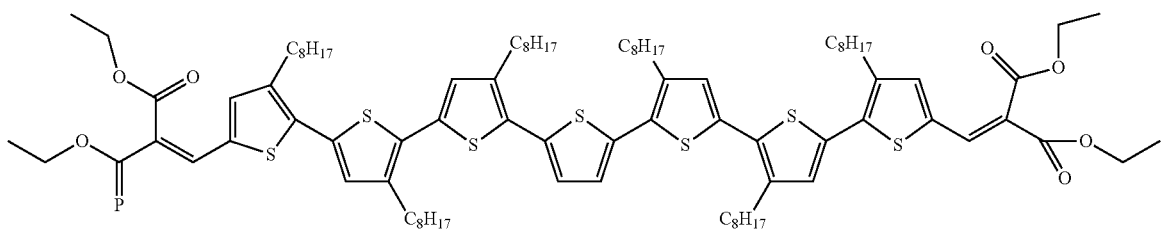

Example 10

1) Synthesis of (3TB3T)T(3TB3T)(CHO)$_2$

To a 100 mL of two-ported flask were added 50 mL of toluene, Br3TB3T(CHO) (0.28 g, 0.20 mmol) and 2,5-di(trimethylstannyl)thiophene (41 mg, 0.10 mmol). Under argon gas protection, Pd(PPh$_3$)$_4$ (20 mg, 0.017 mmol) was added. The mixture was heated to 90° C. and refluxed. After 24 h, the reactants were poured into 100 mL of water and extracted with dichloromethane (100 mL×3). The organic phase was washed with saturated saline (100 mL) and water (100 mL), successively. The organic phase was dried over anhydrous sodium sulfate. After the solvent was removed under reduced pressure, the product was separated was eluant column, in which a mixed solution of petroleum ether and dichloromethane (1:1 vol/vol) was eluant, to give a black solid (0.21 g, yield: 72%).

2) Synthesis of Target Compound

Under argon gas protection, to a 100 mL of two-ported flask filled with (3TB3T)T(3TB3T)(CHO)$_2$ (0.22 g, 0.08 mmol), ethyl cyanoacetate (0.3 mL) and 60 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the product was separated with chromatographic column, in which dichloromethane and petroleum ether (1:1 vol/vol) was eluant, to give a black solid (0.19 g, yield: 82%). MS (MALDI-TOF): C$_{172}$H$_{234}$N$_6$O$_4$S$_{15}$ [M]$^+$, calculated: 2927.41; found: 2927.43.

The structure of product was indicated as follows:

Example 11

1) Synthesis of 11T(CHO)$_2$

To a 100 mL of two-ported flask were added 50 mL of toluene, Br5TCHO (0.39 g, 0.40 mmol) and 2,5-di(trimethylstannyl)thiophene (0.08 g, 0.20 mmol). Under argon gas protection, Pd(PPh$_3$)$_4$ (20 mg, 0.017 mmol) was added. The mixture was heated to 90° C. and refluxed. After 24 h, the reactants were poured into 100 mL of water and extracted with dichloromethane (100 mL×3). The organic phase was washed with saturated saline (100 mL) and water (100 mL), successively. The organic phase was dried over anhydrous sodium sulfate. After the solvent was removed under reduced pressure, the product was separated with chromatographic column, in which a mixed solution of petroleum ether and dichloromethane (1:1 vol/vol) was eluant, to give a brown solid (0.30 g, yield: 81%).

2) Synthesis of Target Compound

Under argon gas protection, to a 100 mL of two-ported flask filled with diformyl oligothiophene 11T(CHO)$_2$ (0.28 g, 0.15 mmol), ethyl cyanoacetate (0.3 mL) and 60 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the product was separated with chromatographic column, in which dichloromethane and petroleum ether (1:1 vol/vol) was eluant, to give a black solid (0.26 g, yield: 84%). MS (MALDI-TOF): C$_{120}$H$_{162}$N$_2$O$_4$S$_{11}$ [M]$^+$, calculated: 2046.95; found: 2046.97.

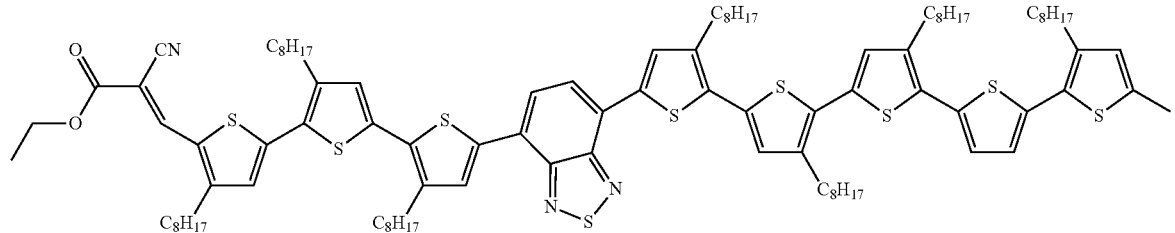

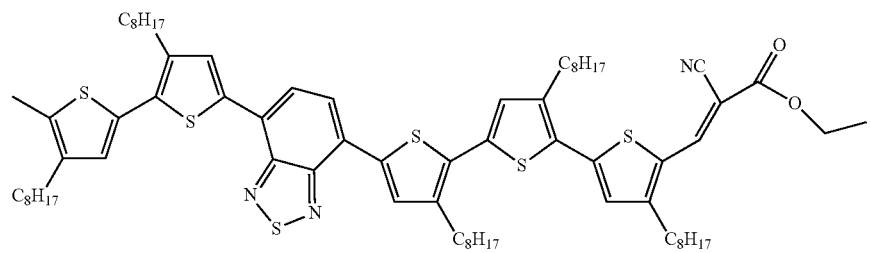

The structure of product was indicated as follows:

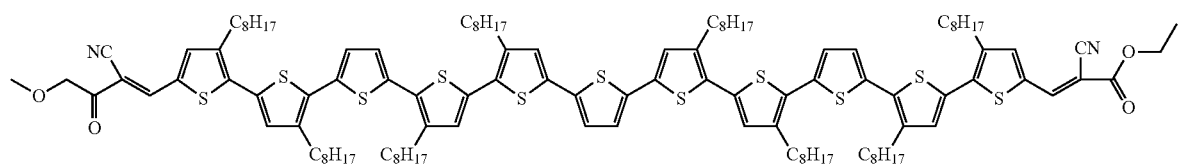

Example 12

1) Synthesis of 5T(BDT)5T (CHO)$_2$

To a 100 mL of two-ported flask were added 60 mL of toluene, Br5TCHO (194 g, 0.20 mmol) and 2,6-di(trimethylstannyl)-4,8-di(2-ethylhexyl)benzodithiophene (0.08 g, 0.10 mmol). Under argon gas protection, Pd(PPh$_3$)$_4$ (20 mg, 0.017 mmol) was added. The mixture was heated to 90° C. and refluxed. After 24 h, the reactants were poured into 100 mL of water and extracted with dichloromethane (100 mL×3). The organic phase was washed with saturated saline (100 mL) and water (100 mL), successively. The organic phase was dried over anhydrous sodium sulfate. After the solvent was removed under reduced pressure, the product was separated with chromatographic column, in which a mixed solution of petroleum ether and dichloromethane (1:1 vol/vol) was eluant, to give a red brown solid (0.16 g, yield: 73%).

2) Synthesis of Target Compound

Under argon gas protection, to a 100 mL of two-ported flask filled with diformyl oligothiophene 5T(BDT)5T (CHO)$_2$ (0.11 g, 0.05 mmol), octyl cyanoacetate (0.2 mL) and 40 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the product was separated with chromatographic column, in which dichloromethane and petroleum ether (2:1 vol/vol) was eluant, to give a black solid (0.10 g, yield: 77%). $^1$H NMR (400 MHz, CHCl$_3$): δ 8.20 (s, 2H), 7.56 (s, 2H), 7.26 (s, 2H), 7.20 (s, 2H), 7.14 (br, 8H), 4.28 (t, J=6.5 Hz, 4H), 4.20 (br, 4H), 2.82 (br, 16H), 1.86 (s, 2H), 1.71 (m, 24H), 1.29 (m, 112H), 1.07 (t, J=7.0 Hz, 6H), 1.00 (br, 6H), 0.89 (br, 30H). MS (MALDI-TOF): [M]$^+$, calculated: 2577.36; found: 2577.82.

The structure of product was indicated as follows:

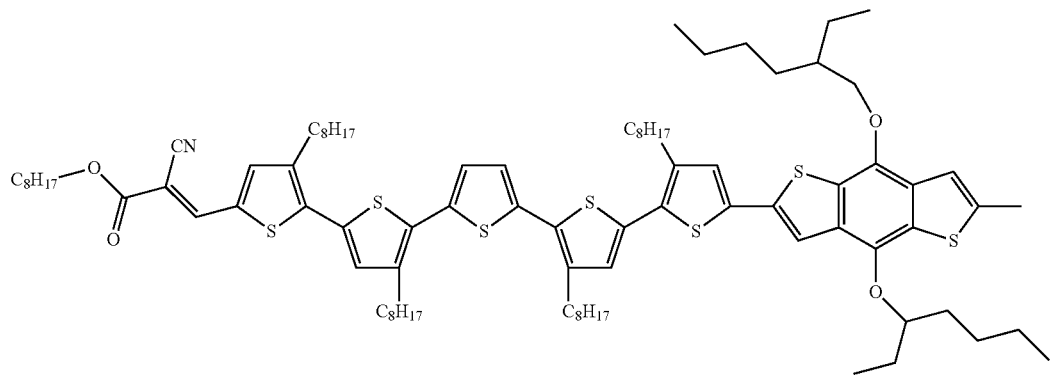

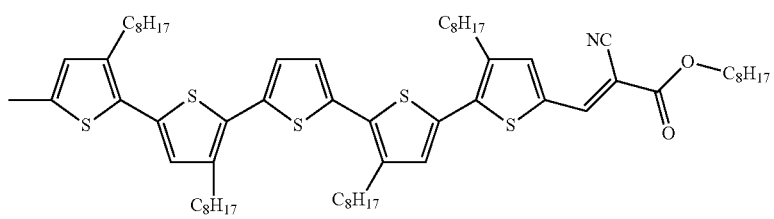

Example 13

1) Synthesis of 5TB5T(CHO)$_2$

To a 100 mL of two-ported flask was added 50 mL of toluene and degassed for 10 min. To the flask were added Br5TCHO (0.29 g, 0.30 mmol), 4,7-bis(4,4,5,5-tetramethyl-1,3,2-dioxoborane)benzothiadiazole (58 mg, 0.15 mmol) and 8 mL of an aqueous solution of K$_2$CO$_3$ (2M). Under argon gas protection, Pd(PPh$_3$)$_4$ (20 mg, 0.017 mmol) was added. The mixture was heated to 90° C. and refluxed. After 24 h, the reactants were poured into 100 mL of water and extracted with dichloromethane (100 mL×3). The organic phase was washed with saturated saline (100 mL) and water (100 mL), successively. The organic phase was dried over anhydrous sodium sulfate. After the solvent was removed under reduced pressure, the product was separated with chromatographic column, in which a mixed solution of petroleum ether and dichloromethane (1:1 vol/vol) was eluant, to give a dark red solid (0.21 g, yield: 72%).

2) Synthesis of Target Compound

Under argon gas protection, to a 100 mL of two-ported flask filled with 5TB5T(CHO)$_2$ (0.38 g, 0.20 mmol), ethyl cyanoacetate (0.3 mL) and 60 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane was eluant, to give a black solid (0.37 g, yield: 88%). $^1$H NMR (400 MHz, CHCl$_3$): δ 8.18 (s, 2H), 7.94 (d, J=Hz, 2H), 7.75 (d, J=Hz, 2H), 7.52 (s, 2H), 7.17 (s, 2H), 7.09 (m, 6H), 7.92-7.97 (m, 1H), 4.34 (q, J=Hz, 4H), 2.80 (br, 16H), 1.70 (m, 16H), 1.29 (m, 86H), 0.89 (m, 24H). MS (MALDI-TOF): C$_{122}$H$_{162}$N$_4$O$_4$S$_{11}$ [M]$^+$, calculated: 2098.95; found: 2099.02.

The structure of product was indicated as follows:

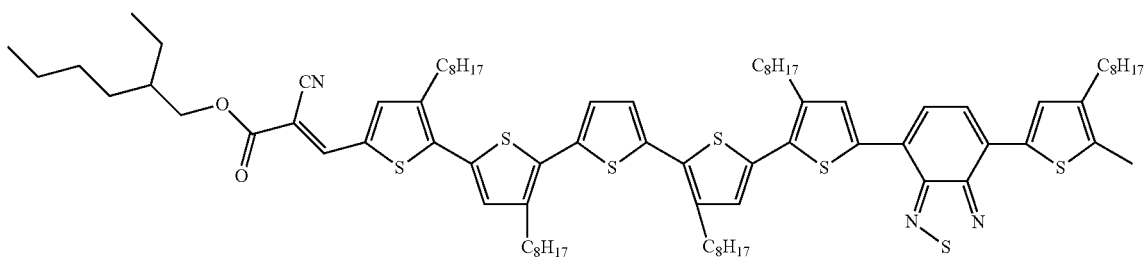
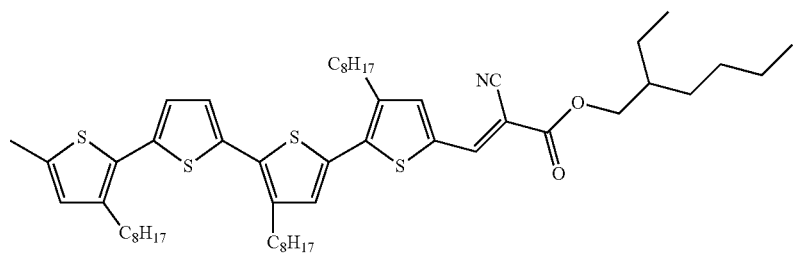

Example 14

To a 50 mL of single-ported flask were added diformaldehyde heptathiophene 7T(CHO)$_2$ (50 mg, 0.038 mmol) and 30 mL of acetic acid. The mixture was stirred to disperse homogeneously. To the flask were added 3-ethyl rhodanine (20 mg, 0.12 mmol) and ammonium acetate (20 mg, 0.12 mmol). The resultant mixture was stirred and heated under reflux overnight. The mixture was cooled to room temperature, poured into 200 mL of water, and extracted by adding 50 mL of dichloromethane. The organic phase was washed by adding 50 mL of water (three times). The organic phase was dried over anhydrous magnesium sulfate, filtered and rotary dried. The product was separated by column chromatography with dichloromethane and petroleum ether (1:1) as eluant to give a brown solid (60 mg, yield: 98.4%). $^1$H NMR (400 MHz, CHCl$_3$): δ 7.764 (s, 2H) 7.209 (s, 2H), 7.100 (s, 4H), 7.011 (s, 2H), 4.21 (q, 4H, J=7.0 Hz), 2.74 (t, 12H, J=6.7 Hz), 1.709 (m, 12H), 1.300 (m, 60H), 0.882 (t, 18H, J=6.6 Hz). HRMS (MALDI-FTICR): C$_{88}$H$_{122}$N$_2$O$_2$S$_{11}$ [M]$^+$, calculated: 1592.64; found: 1591.10.

The structure of product was indicated as follows:

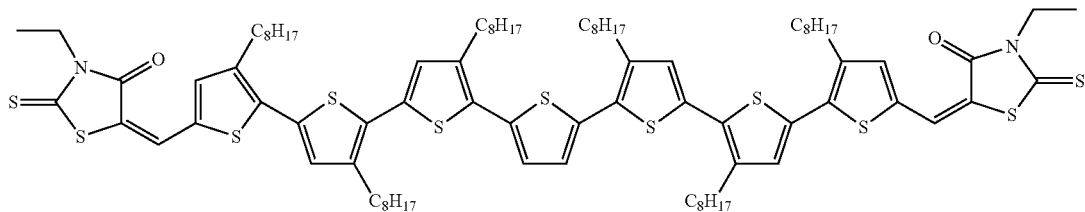

Example 15

To a 50 mL of single-ported flask were added diformylheptathiophene (100 mg, 0.077 mmol), hexafluoroacetylacetone (77 mg, 0.37 mmol), and then 20 mL of acetic acid and 5 mL of chloroform. The mixture was stirred to dissolve. The mixture was heated under reflux with stirring overnight. After cooling to room temperature, the mixture was extracted by adding 50 mL of dichloromethane. The organic phase was washed with 50 mL of water (once), 50 mL of saturated aqueous sodium bicarbonate solution (once), and 50 mL of water (once). The organic phase was dried over anhydrous magnesium sulfate, filtered and rotary dried. The product was separated by column chromatography with dichloromethane and petroleum ether (2:1) as eluant to give a blackish green solid (120 mg, yield: 93.0%). $^1$H NMR (400 MHz, CHCl$_3$): δ 7.878 (s, 2H) 7.396 (s, 2H), 7.155 (s, 4H), 6.976 (s, 2H), 2.757 (t, 12H, J=6.7 Hz), 1.630 (m, 12H), 1.215 (m, 60H), 0.810 (t, 18H, J=6.6 Hz). HRMS (MALDI-FTICR): $C_{88}H_{112}F_{12}O_4S_7$ [M], calculated: 1686.26; found: 1685.32.

The structure of product was indicated as follows:

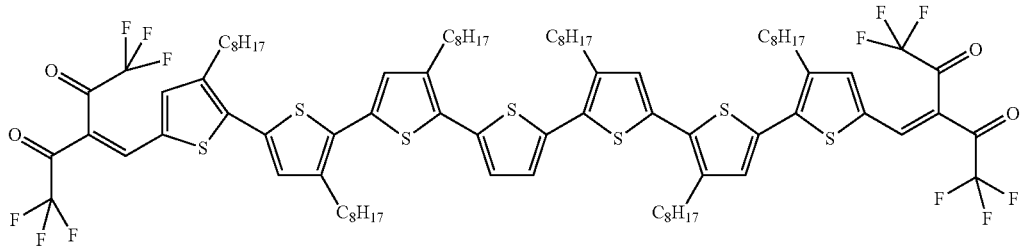

Example 16

To a 25 mL of two-ported flask were added diformylheptathiophene (50 mg, 0.038 mmol), n-butylamine (44 mg, 0.6 mmol), and then 10 mL of dichloromethane. The mixture was stirred to dissolve. Anhydrous sodium sulfate (1 g, 7 ml) was added. The mixture was stirred at room temperature for 24 h. The reaction system was rotary dried. 15 mL of benzene was added to dissolve the product. To the solution were added trifluoroethyl acetoacetate (73 mg, 0.4 mmol) and acetic anhydride (0.1 g, 0.98 mmol). After heating under reflux for 4 h, the mixture was cooled to room temperature and rotary dried. The resultant product was redissolved in 50 mL of dichloromethane. The product was washed with 50 mL of water (three times). The organic phase was dried over anhydrous magnesium sulfate and separated by column chromatography to give a dark green solid (32 mg, yield: 52.6%). $^1$H NMR (400 MHz, CHCl$_3$): δ 7.853 (s, 2H) 7.409 (s, 1H), 7.342 (s, 1H) 7.134 (s, 4H), 7.021 (s, 2H), 4.32 (dd, 4H, J=6.9 Hz, J=32.3 Hz) 2.803 (t, 12H, J=6.7 Hz), 1.685 (m, 18H), 1.259 (m, 60H), 0.878 (t, 18H, J=6.6 Hz). HRMS (MALDI-FTICR): $C_{90}H_{122}F_6O_6S_7$ [M]$^+$, calculated: 1638.37; found: 1637.72.

The structure of product was indicated as follows:

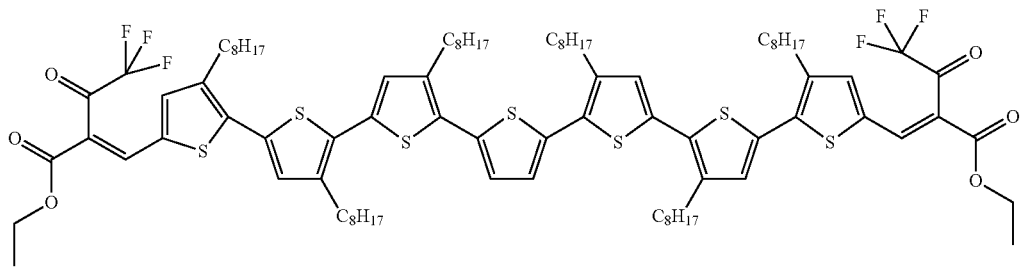

Example 17

Under argon gas protection, to a two-ported flask filled with diformylheptathiophene 7T(CHO)$_2$ (0.13 g, 0.10 mmol), 1,3-dimethyl-barbituric acid (0.156 g, 1.00 mmol) and 50 mL of dry trichloromethane was added dropwise three drops of pyridine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane-ethyl acetate was eluant, to give a blue black solid (0.12 g, yield: 79%). MALDI-TOF MS (m/z): $C_{90}H_{124}N_4O_6S_7$ [M]$^+$, calculated: 1580.76; found: 1580.71.

The structure of product was indicated as follows:

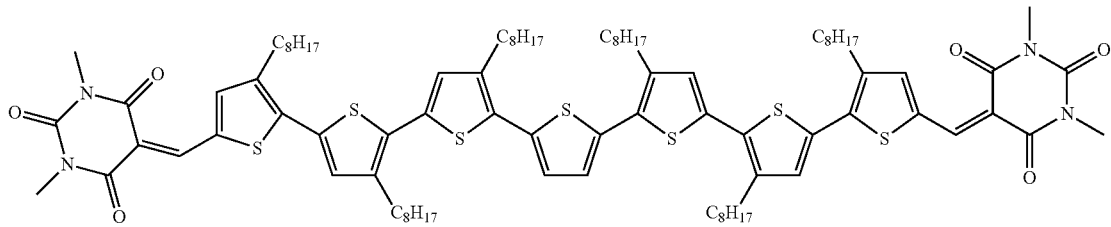

Example 18

Under argon gas protection, to a two-ported flask filled with diformylheptathiophene 7T(CHO)$_2$ (0.13 g, 0.10 mmol), 2,2,2-trifluoroethyl 2-cyanoacetate (0.167 g, 1.00 mmol) and 50 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane-petroleum ether was eluant, to give a blackish green solid (0.11 g, yield: 70%). MALDI-TOF MS (m/z): $C_{88}H_{116}F_6N_2O_4S_7$ [M]$^+$, calculated: 1603.69; found: 1603.71.

The structure of product was indicated as follows:

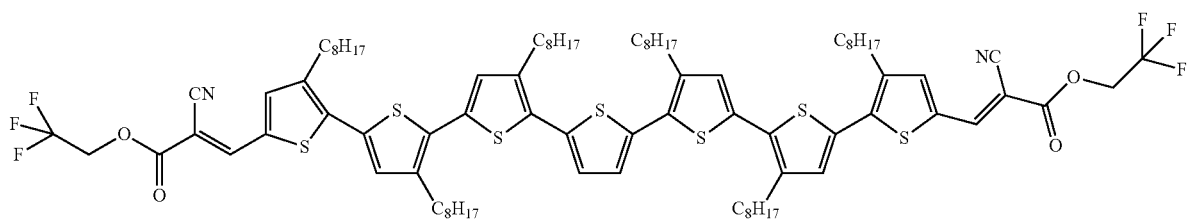

Example 19

Under argon gas protection, to a two-ported flask filled with diformylheptathiophene 7T(CHO)$_2$ (0.13 g, 0.10 mmol), 2,2,3,3,3-pentafluoropropyl 2-cyanoacetate (0.217 g, 1.00 mmol) and 50 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane-petroleum ether was eluant, to give a blackish green solid (0.12 g, yield: 70%). MALDI-TOF MS (m/z): $C_{90}H_{116}F_{10}N_2O_4S_7$ [M]$^+$, calculated: 1702.68; found: 1702.70.

The structure of product was indicated as follows:

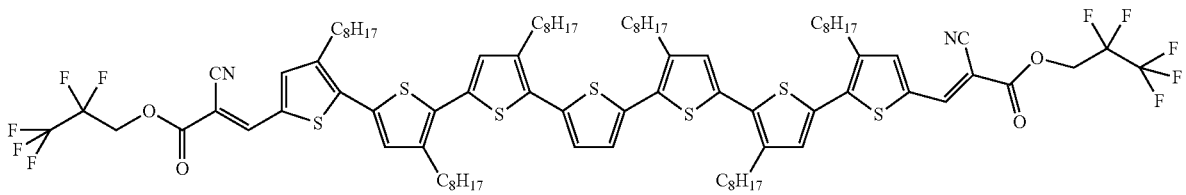

Example 20

Under argon gas protection, to a two-ported flask filled with diformylheptathiophene 7T(CHO)$_2$ (0.13 g, 0.10 mmol), 2,2,3,3,4,4,5,5,6,6,7,7,8,8,8-pentadecafluorooctyl 2-cyanoacetate (0.467 g, 1.00 mmol) and 50 mL of dry trichloromethane was added dropwise three drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane-petroleum ether was eluant, to give a blackish green solid (0.16 g, yield: 73%). MALDI-TOF MS (m/z): $C_{100}H_{116}F_{30}N_2O_4S_7$ [M]$^+$, calculated: 2203.65; found: 2203.71.

The structure of product was indicated as follows:

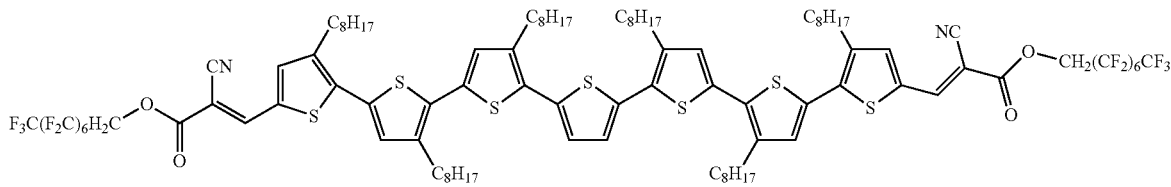

Example 21

Under argon gas protection, to a 100 mL of two-ported flask filled with diformylheptathiophene 7T(CHO)$_2$ (0.13 g, 0.10 mmol), (E)-5-(3-ethyl-5-carbonylthiazolin-2-ylide)-3-octyl-2,4-dicarbonylthiazoline (0.356 g, 1.00 mmol), ammonium acetate (0.077 g, 1 mmol) were added 30 mL of dry chlorobenzene and 20 mL of glacial acetic acid. The mixture was stirred at room temperature overnight. The mixture was poured into 100 mL of water and extracted with dichloromethane (30 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which dichloromethane-petroleum ether was eluant, to give a blue black solid (0.16 g, yield: 80%). MALDI-TOF MS (m/z): $C_{110}H_{156}N_4O_4S_{13}$ [M]$^+$, calculated: 2013.85; found: 2013.83.

The structure of product was indicated as follows:

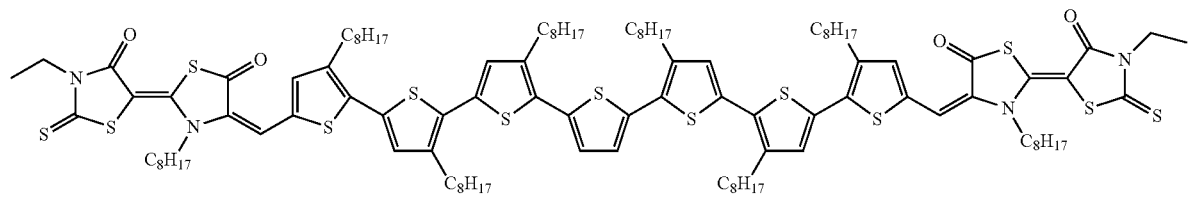

Example 22

Under argon gas protection, to a 50 mL of two-ported flask filled with diformyl bithiophenetrithienothiophene DFD3TBT (230 mg, 0.20 mmol) and 25 mL of trichloromethane was added 0.8 mL of n-octyl cyanoacetate. The mixture was stirred under reflux overnight. After cooling to room temperature, the mixture was poured into 100 mL of water and extracted with dichloromethane (30 mL×3). The organic phase was washed with water (100 mL), saturated saline (100 mL) and water (100 mL), successively. The organic phase was dried over anhydrous sodium sulfate. After the solvent was removed under reduced pressure, the product was separated with chromatographic column, in which a mixed solution of petroleum ether and dichloromethane (2:1 vol/vol) was eluant. $^1$H NMR (400 MHz, CHCl$_3$): 8.21 (s, 2H), 7.60 (s, 2H), 7.31 (m, 4H), 7.14 (d, J=3.6 Hz, 2H), 7.07 (s, 2H), 3.64 (t, J=6.4 Hz, 4H), 2.84 (t, J=7.6 Hz, 4H), 2.79 (t, J=7.6 Hz, 4H), 1.68 (m, 12H), 1.28 (m, 60H), 0.89 (m, 18H).

The structure of product was indicated as follows:

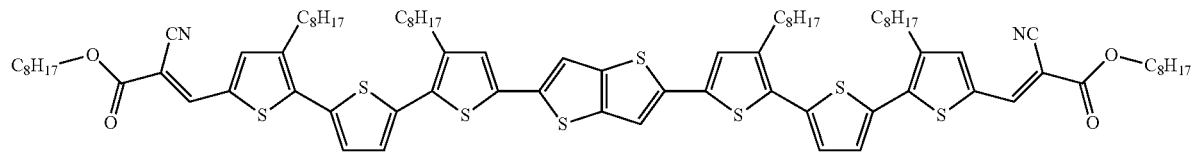

Example 23

Under argon gas protection, to a two-neck flask filled with bis(formyltrithiophene)silole (147 mg, 0.104 mmol), octyl cyanoacetate (10-folds molar equivalent) and 50 mL of dry trichloromethane was added dropwise several drops of triethylamine. The mixture was stirred at room temperature overnight. The mixture was poured into 100 mL of water and extracted with dichloromethane (20 mL×3). The organic phase was washed with water (50 mL), saturated saline (50 mL) and water (50 mL), successively. The organic phase was dried over anhydrous sodium sulfate. After the solvent was removed under reduced pressure, the resultant product was separated with chromatographic column, in which petroleum ether-dichloromethane (1:1) was eluant, to give a brown solid (yield: 90%). MALDI-TOF MS (m/z): C$_{90}$H$_{124}$N$_4$O$_6$S$_7$ [M]$^+$, calculated: 1773.9; found: 1773.9.

The structure of product was indicated as follows:

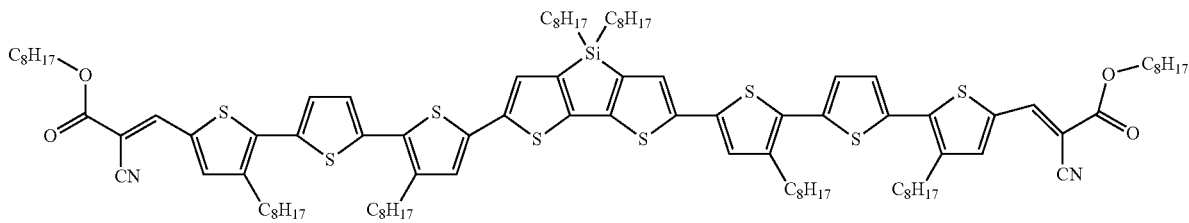

Example 24

Under argon gas protection, to a two-ported flask filled with 3T(BDT)3T(CHO)2 (1.0 g, 0.71 mmol), octyl cyanoacetate (10-folds molar equivalent) and 70 mL of dry trichloromethane was added dropwise several drops of triethylamine. The mixture was stood at room temperature for 40 h and then was poured into 100 mL of water and extracted with dichloromethane (50 mL×3). The organic phase was washed with water (100 mL), saturated saline (100 mL) and water (100 mL), successively. The organic phase was dried over anhydrous sodium sulfate. After the solvent was removed under reduced pressure, the resultant product was separated with chromatographic column, in which petroleum ether-dichloromethane (2:3) was eluant, to give a black solid (yield: 70%). MALDI-TOF MS (m/z): $C_{106}H_{148}N_2O_4S_8$ $[M]^+$, calculated: 1768.92; found: 1768.93.

The structure of product was indicated as follows:

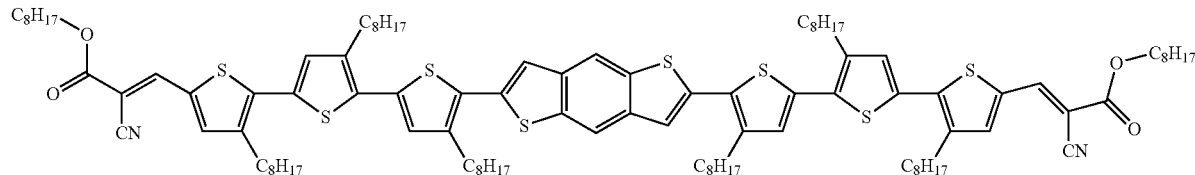

Example 25

Under argon gas protection, bis(formyltrithiophene)oxyisooctyl benzobithiophene, 3-ethylrhodamine (10-folds molar equivalent) and ammonium acetate (2 mg, 0.012 mmol) were stirred and heated under reflux overnight. The mixture was cooled to room temperature, poured into 200 mL of water and extracted by adding 80 mL of dichloromethane. The organic phase was washed by adding 80 mL of water (three times). The organic phase was dried over anhydrous magnesium sulfate, filtered and rotary dried. The product was separated by column chromatography with dichloromethane and petroleum ether (2:1) as eluant. The yield is 70%. MALDI-TOF MS (m/z): $C_{94}H_{124}N_2O_4S_{12}$ $[M]^+$, calculated: 1728.62; found: 1728.61.

The structure of product was indicated as follows:

Example 26

Under argon gas protection, bis(formaldehydetrithiophene)silole (170 mg, 0.1 mmol), 3-ethylrhodamine (10-fold molar equivalent) and ammonium acetate (20 mg, 0.012 mmol) were stirred and heated under reflux overnight. The mixture was cooled to room temperature, poured into 200 mL of water and extracted by adding 80 mL of dichloromethane. The organic phase was washed by adding 50 mL of water (three times). The organic phase was dried over anhydrous magnesium sulfate, filtered and rotary dried. The product was separated by column chromatography with dichloromethane and petroleum ether (1:1) as eluant to give a brown solid (yield: 82%). MALDI-TOF MS (m/z): $C_{92}H_{124}N_2O_2S_{12}Si$ $[M]^+$, calculated: 1701.61; found: 1701.60.

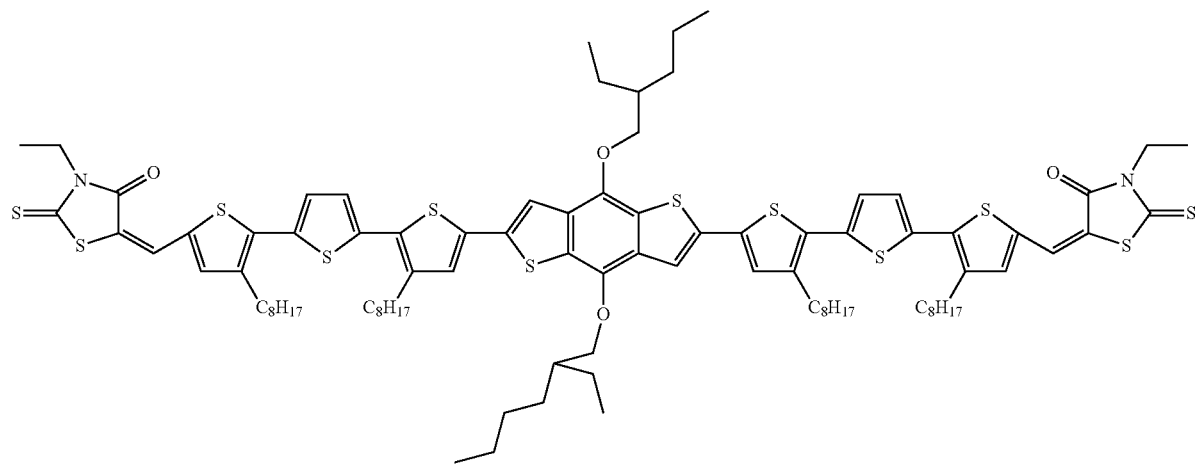

The structure of product was indicated as follows:

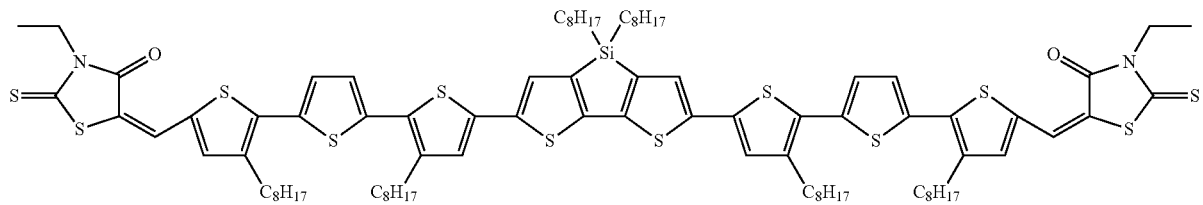

Example 27

The process was identical to Example 2 except that ethyl cyanoacetate was replaced with malononitrile. The yield was 83%. MALDI-TOF MS (m/z): $C_{106}H_{148}N_2O_4S_8$ [M]$^+$, calculated: 1400.69; found: 1400.69.

The structure of product was indicated as follows:

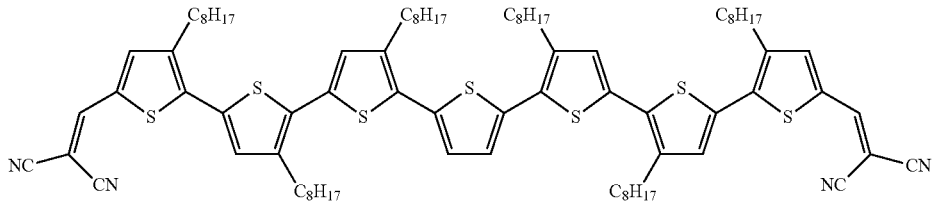

Under argon gas protection, to a two-ported flask filled with intermediate HOC3T(BDT)3TCHO (1.0 g, 0.71 mmol), octyl cyanoacetate (10-fold molar equivalent) and 70 mL of dry trichloromethane was added dropwise several drops of triethylamine. The mixture was stood at room temperature for 40 h. The mixture was poured into 100 mL of water and extracted with dichloromethane (50 mL×3). The organic phase was washed with water (100 mL), saturated saline (100 mL) and water (100 mL), successively. The organic phase was dried over anhydrous sodium sulfate. After the solvent was removed under reduced pressure, the resultant product was separated with chromatographic column, in which petroleum ether-dichloromethane (2:3) was eluant, to give a black solid (yield: 70%). MALDI-TOF MS (m/z): $C_{106}H_{148}N_2O_4S_8$ [M]$^+$, calculated: 1768.92; found: 1768.93.

Example 28

Under argon gas protection, to a two-ported flask filled with 3T(OEH-BDT)3T(CHO)$_2$ (360 mg, 0.2 mmol), octyl cyanoacetate (10-fold molar equivalent) and 100 mL of dry trichloromethane was added dropwise several drops of triethylamine. The mixture was stood at room temperature overnight. The mixture was poured into 100 mL of water and extracted with dichloromethane (30 mL×3). The organic phase was washed with water (60 mL), saturated saline (60 mL) and water (60 mL), successively. The organic phase was dried over anhydrous sodium sulfate. After the solvent was removed under reduced pressure, the resultant product was separated with chromatographic column, in which petroleum ether-dichloromethane (1:2) was eluant, to give a brown solid (yield: 91%). MALDI-TOF MS (m/z): $C_{106}H_{148}N_2O_4S_8$ [M]$^+$, calculated: 1800.91; found: 1800.90.

The structure of product was indicated as follows:

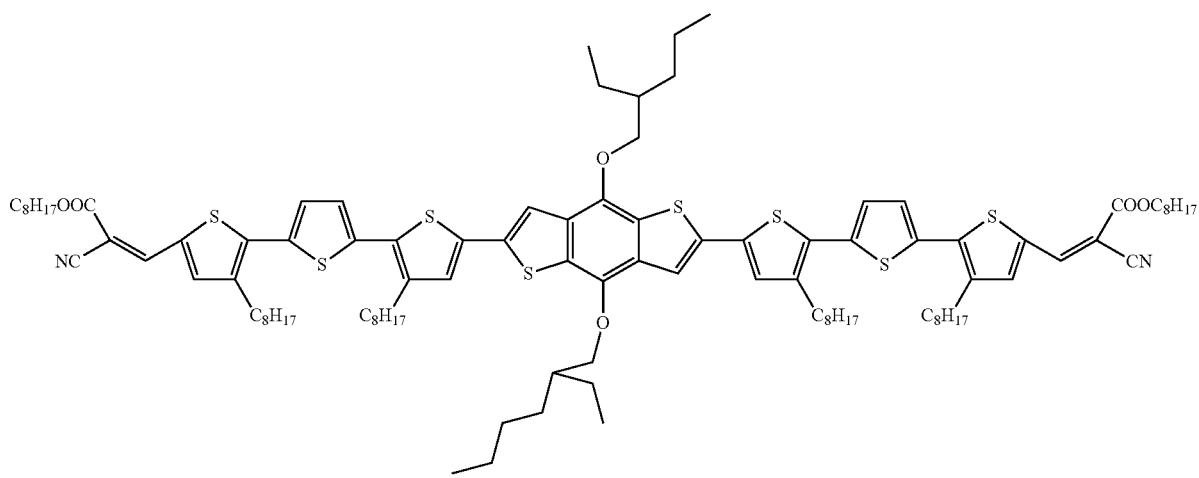

Example 29

Under argon gas protection, to a two-ported flask filled with intermediate 5T(OEH-BDT)5T (CHO)$_2$ (0.18 g, 0.08 mmol), octyl cyanoacetate (10-fold molar equivalent) and 60 mL of dry trichloromethane was added dropwise several drops of triethylamine. The mixture was stood at room temperature for 48 h. The mixture was poured into 100 mL of water and extracted with dichloromethane (50 mL×3). The organic phase was washed with water (80 mL), saturated saline (80 mL) and water (80 mL), successively. The organic phase was dried over anhydrous sodium sulfate. After the solvent was removed under reduced pressure, the resultant product was separated with chromatographic column, in which petroleum ether-dichloromethane (2:3) was eluant, to give a black solid (yield: 76%). MALDI-TOF MS (m/z): $C_{154}H_{220}N_2O_6S_{12}$ [M]$^+$, calculated: 2577.36; found: 2577.35.

The structure of product was indicated as follows:

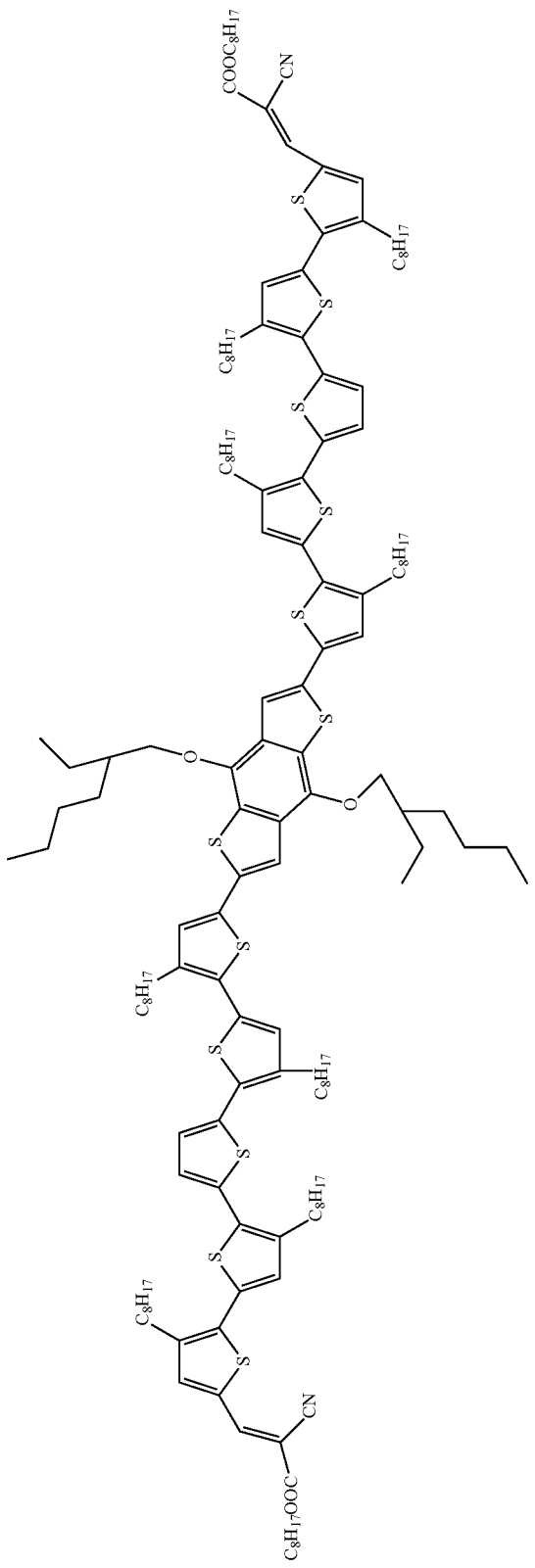

Example 30

The process was identical to Example 14, except that 3-ethyl rhodamine was replaced with 3-octyl rhodaminef. The yield of reaction was 90%. MALDI-TOF MS (m/z): $C_{100}H_{145}N_2O_2S_{11}$ [M]$^+$, calculated: 1758.83; found: 1758.82.

The structure of product was indicated as follows:

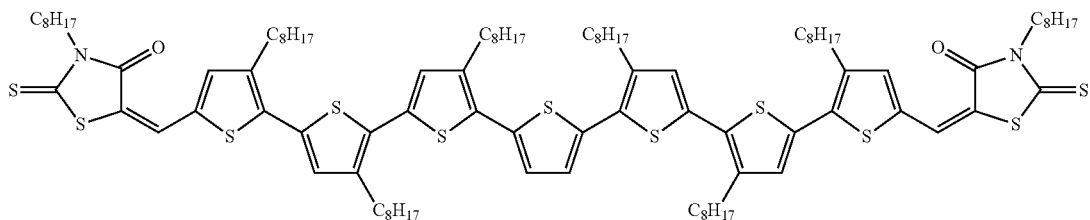

Example 31

The process was identical to Example 14, except that 3-ethyl rhodamine was replaced with 3-methyl rhodamine. The yield of reaction was 96%. MALDI-TOF MS (m/z): $C_{86}H_{118}N_2O_2S_{11}$ [M]$^+$, calculated: 1562.61; found: 1562.

The structure of product was indicated as follows:

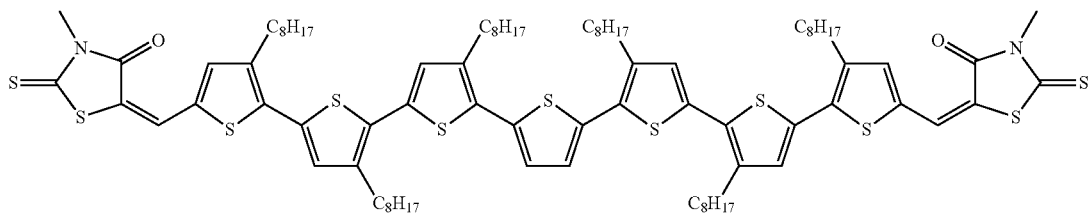

Example 32

The process was identical to Example 14, except that 7T(CHO)$_2$ was replaced with 3T(DPP)3T(CHO)$_2$. The yield of reaction was 76%. MALDI-TOF MS (m/z): $C_{82}H_{105}N_3O_2S_{11}$ [M]$^+$, calculated: 1547.50; found: 1547.52.

The structure of product was indicated as follows:

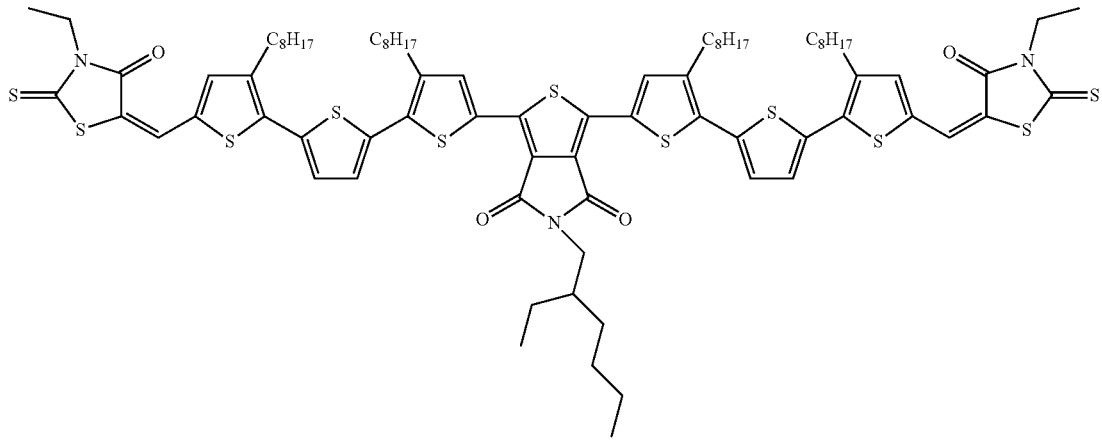

Example 33

The process was identical to Example 2, except that 7T(CHO)$_2$ was replaced with 3T(DPP)3T(CHO)$_2$. The yield of reaction was 76%. MALDI-TOF MS (m/z): C$_{82}$H$_{105}$N$_3$O$_2$S$_{11}$ [M]$^+$, calculated: 1547.50; found: 1547.52.

The structure of product was indicated as follows:

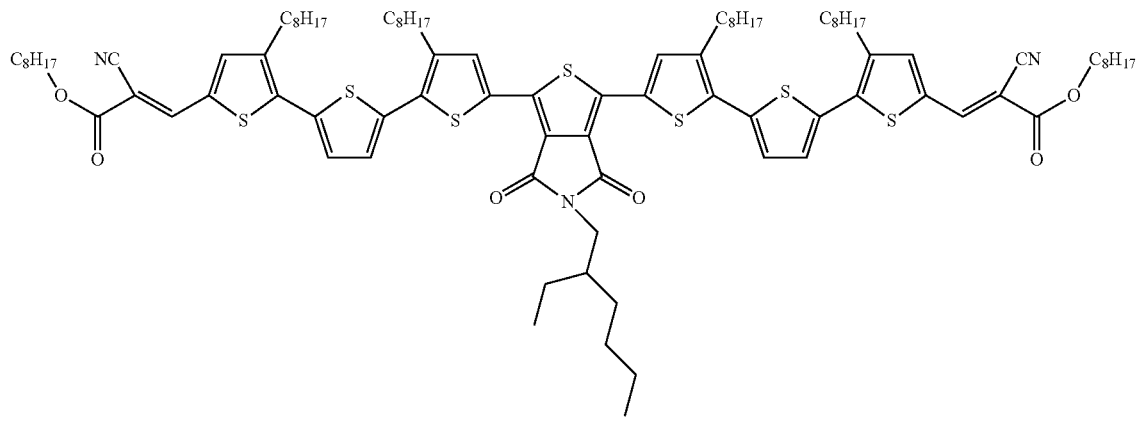

Example 34

The process was identical to Example 14, except that 7T(CHO)$_2$ was replaced with 5T(CHO)$_2$. The yield of reaction was 96%. MALDI-TOF MS (m/z): C$_{65}$H$_{90}$N$_2$O$_2$S$_9$ [M]$^+$, calculated: 1218.44; found: 1218.45.

The structure of product was indicated as follows:

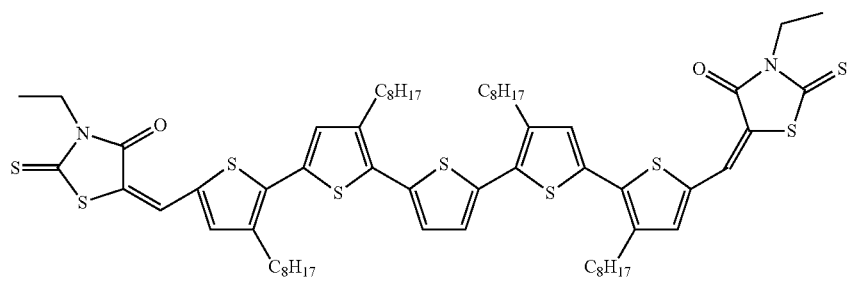

Example 35

The process was identical to Example 14, except that 3-ethyl rhodamine was replaced with 3-(1-acetylethylester) methyl rhodamine. The yield of reaction was 87%. MALDI-TOF MS (m/z): C$_{92}$H$_{126}$N$_2$O$_6$S$_{11}$ [M]$^+$, calculated: 1706.65; found: 1706.64.

The structure of product was indicated as follows:

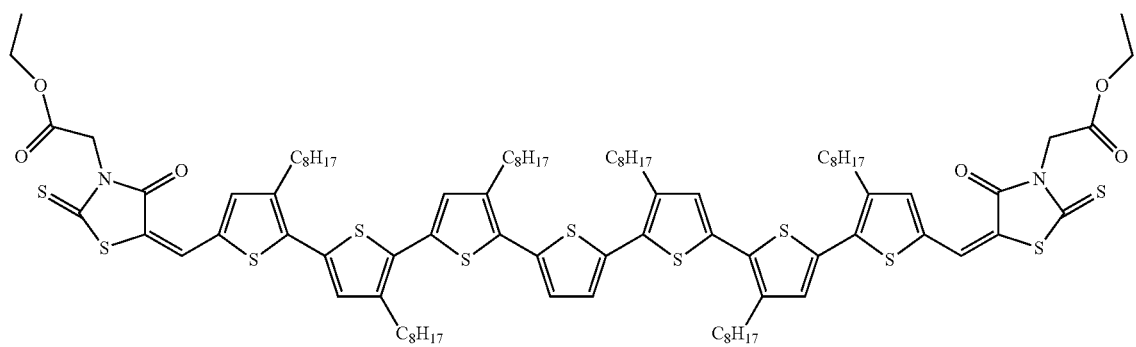

Example 36

The process was identical to Example 2, except that ethyl cyanoacetate was replaced with 1-sulfonylbutyl-2,3,3-trimethylindolium. The yiled of reaction was 87%. MALDI-TOF MS (m/z): $C_{106}H_{146}N_2O_6S_9$ [M]$^+$, calculated: 1830.86; found: 1830.87.

The structure of product was indicated as follows:

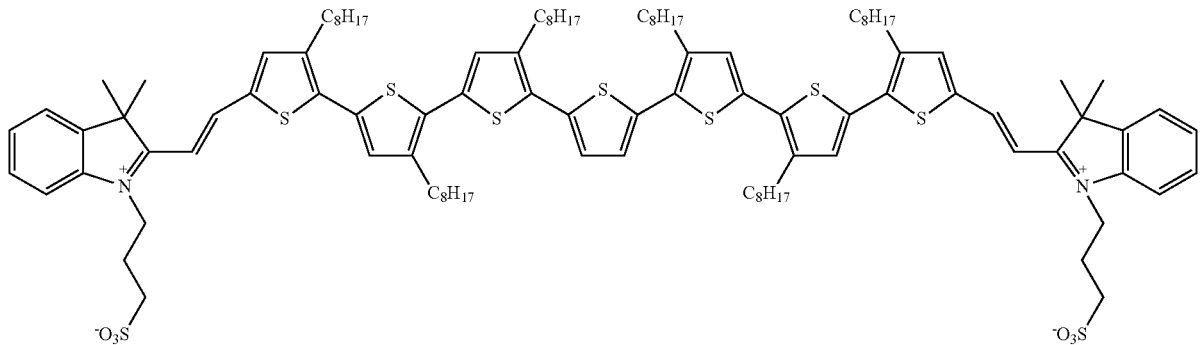

Example 37

The process was similar to Example 14, except that 7T(CHO)$_2$ was replaced with diformaldehyde benzothiazole dithiophene. The yield of reaction was 79%. MALDI-TOF MS (m/z): $C_{42}H_{50}N_4O_2S_7$ [M]$^+$, calculated: 866.19; found: 866.19.

The structure of product was indicated as follows:

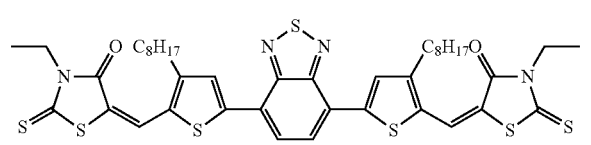

Example 38

Thermal Stability Tests on Donor-Receptor Type Obligothiophenes Comprising Receptor Terminals in Examples 2 to 6

The thermal stability of donor-receptor type obligothiophenes comprising receptor terminals was tested by thermogravimetric analysis (TG) on TA instrument SDT-TG Q600 Thermogravimetric Analyzer and by differential scanning calorimetry (DSC) on TA instrument DSC-2910 Analyzer. The heating scanning rate is 10° C./min under nitrogen flow.

Example 39

Cyclic Voltammetry Tests on Compounds in Examples 4 to 6

Figure 3:
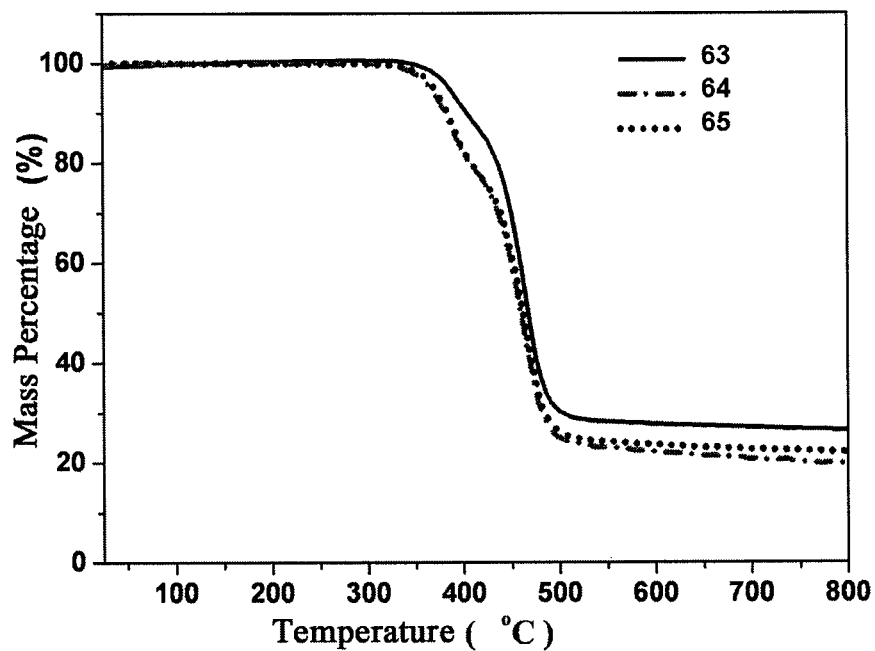
FIG. 3 is cyclic voltammetry curves of the compounds in Examples 4, 5 and 6 in the present application.

The energy level structure of a molecule can be learnt by cyclic voltammetry to estimate the magnitude of the Highest Occupied Molecular Orbital (HOMO) and the Lowest Unoccupied Molecular Orbital (LUMO). Electrochemical property tests were carried out on LK98B II Electrochemical Workstation, in which the electrolytic tank was a three-electrode system (glassy carbon electrode was used as working electrode, platinum wire electrode was used as auxiliary electrode and calomel electrode was used as reference electrode), ferrocene was used as internal standard, dried dichloromethane was used as solvent, 0.1 M tetrabutylammonium hexafluorophosphate (n-Bu$_4$NPF$_6$) was used as supporting electrolyte and the scanning rate was 100 mV s$^{-1}$. Under argon gas protection, the cyclic voltammetry curves obtained by scanning were shown in FIG. 3. The HOMO and LUMO energy levels of molecules were calculated according to the reference (Li, Y. F.; Cao, Y.; Gao, J.; Wang, D. L.; Yu, G.; Heeger, A. J. Synth. Met. 1999, 99, 243.):

Example 4: E(HOMO)=−5.09 eV, E(LUMO)=−3.33 eV.

Example 5: E(HOMO)=−5.13 eV, E(LUMO)=−3.29 eV.

Example 6: E(HOMO)=−5.10 eV, E(LUMO)=−3.26 eV.

Example 40

Figure 4:
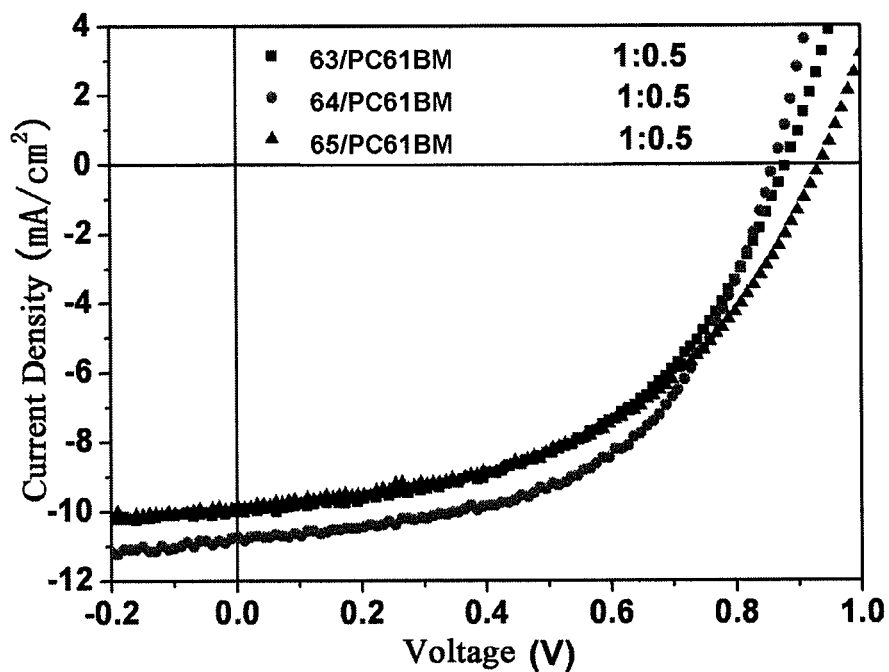
FIG. 4 is current density versus voltage curves of the compounds in Examples 4, 5 and 6 in the present application.

Manufacturing Solar Cell Devices with Compounds in Examples 4 to 6 as Electron Donors The structure of the devices was ITO/PEDOT:PSS/donor: PC$_{61}$BM/Ca/Al, in which the donor was any one of compounds in Examples 4-6. The process for manufacturing the device was outlined as follows. First of all, an ITO (indium tin oxide, anode) glass was pre-treated. The specific steps are the ITO glass was scrubbed with a detergent and cleaned with deionized water. The ITO glass was then ultrasonically cleaned with acetone and isopropanol each for 20 min, successively. Then, the ITO glass was placed in an oven to dry. A layer of PEDOT:PSS (Baytron PVP Al 4083) was spin coated on the pre-treated ITO glass as anode modified layer (40 nm). After PEDOT:PSS was completely dried by heating at 120° C. for 20 min, a solution of a mixture of donor:PC$_{61}$BM in chloroform (mass ratio of donor:PC$_{61}$BM was 1:0.5 and the concentration of donor was 8 mg/mL) was spin coated on the surface of PEDOT:PSS as an active layer (140 nm). Ca (20 nm) and metal electrode Al (80 nm) were vapor deposited. The vacuum degree was kept below 4×10$^{-4}$ Pa during vapor deposition. The devices were tested for their properties by computer-controlled Keithley 2400 digital Source Meter under standard sunlight (AM 1.5 G) illumination. The current density versus voltage curves of the devices were shown in FIG. 4 and the property parameters were listed in Table 1.

TABLE 1

Comparison of Properties of Solar Cells
Manufactured with Compounds in Examples 4-6
(Light Intensity was 100 mW/cm² Measured under AM1.5G Illumination)

| | Device Parameters | | | |
|---|---|---|---|---|
| | Short-Circuit Current Density $J_{sc}$ (mA cm$^{-2}$) | Open-Circuit Voltage $V_{oc}$ (V) | Filling Factor FF (%) | Energy Conversion Efficiency PCE (%) |
| Example 4/PC$_{61}$BM (1:0.5) | 9.94 | 0.88 | 51.0 | 4.46 |
| Example 5/PC$_{61}$BM (1:0.5) | 10.74 | 0.86 | 55.0 | 5.08 |
| Example 6/PC$_{61}$BM (1:0.5) | 9.91 | 0.93 | 49.1 | 4.52 |

As seen from Table 1, in the bulk heterojunction solar cell devices which were treated with a solution prepared with the compounds of the present application, the ultraviolet visible absorption reaches 800 nm; the open-circuit voltage of solar devices reaches 0.85 V or more; the short-circuit current reaches 9 mA/cm² or more; and the maximum photovoltaic conversion efficiency reaches 5% or more.

Example 41

Ultraviolet Visible Spectrum Tests on Donor-Receptor Type Oligothiophene Comprising a Receptor Terminal in Example 14

Figure 5:
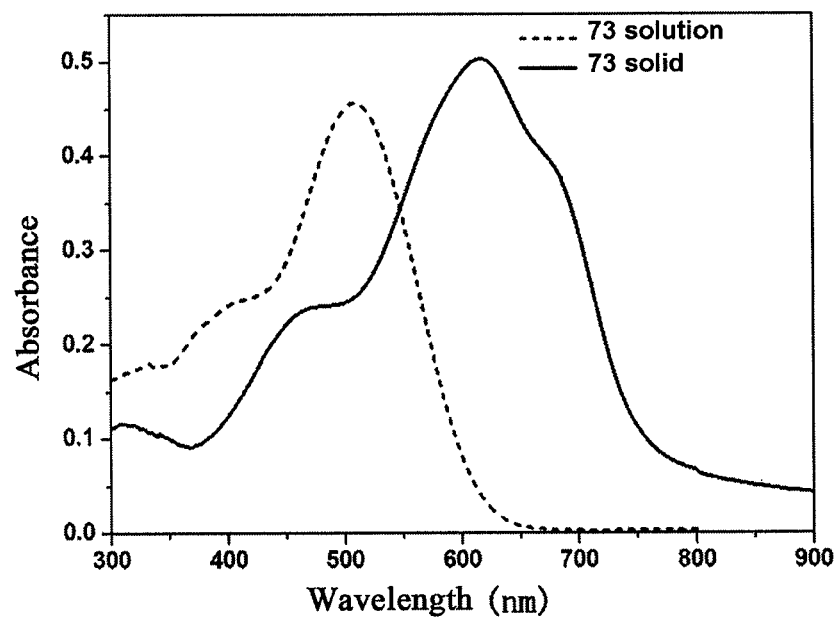
FIG. 5 shows ultra violet-visible absorption spectra of the solution and the thin film of the compound in Example 14 in the present application.

The compound in Example 14 was formulated to 10$^{-5}$ mol/L and 10$^{-2}$ mol/L of chloroform solutions, respectively. The former solution was measured for its ultraviolet absorption. The latter solution was spin coated on quartz plate at 1200 rpm and the resultant film was measured for its ultraviolet absorption. All the measurements were conducted under scanning range of 300-1000 nm and the measuring instrument of Jasco V-570 UV/VIS/NIR Spectrophotometer. The ultraviolet visible absorption spectra were shown in FIG. 5.

Example 42

Cyclic Voltammetry Tests on Solution and Film of Compound in Example 14

Figure 6:
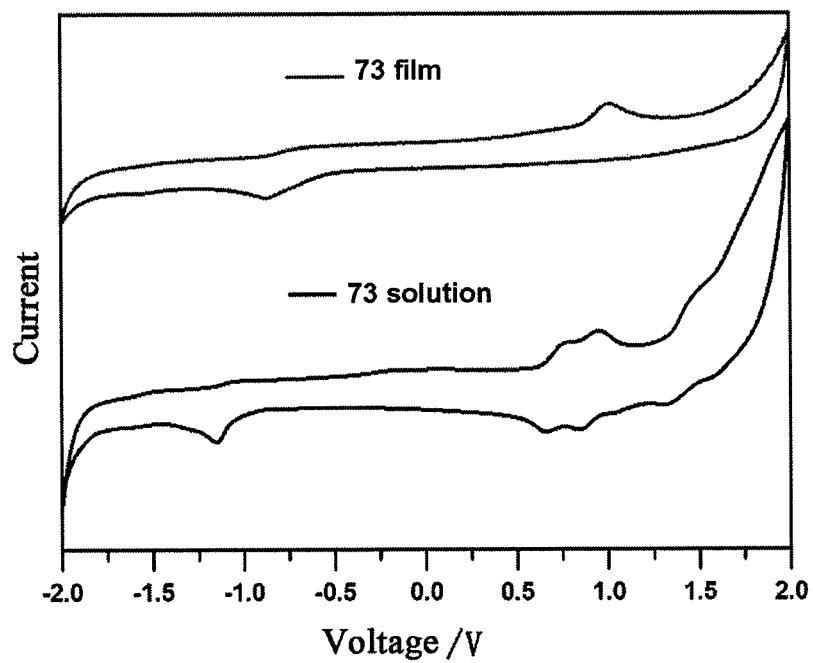
FIG. 6 shows cyclic voltammetry curves of the solution and the thin film of the compound in Example 14 in the present application.

The energy level structure of a molecule can be learnt by cyclic voltammetry to estimate the magnitude of the Highest Occupied Molecular Orbital (HOMO) and the Lowest Unoccupied Molecular Orbital (LUMO). Electrochemical property tests were carried out on LK98B II Electrochemical Workstation, in which the electrolytic tank was a three-electrode system (glassy carbon electrode was used as working electrode, platinum wire electrode was used as auxiliary electrode and calomel electrode was used as reference electrode), ferrocene was used as internal standard, dried dichloromethane was used as solvent, 0.1 M tetrabutylammonium hexafluorophosphate (n-Bu$_4$NPF$_6$) was used as supporting electrolyte, and the scanning rate was 100 mV·s$^{-1}$; in the test for electrochemistry of film, dried acetonitrile was used as solvent, 0.1 M tetrabutylammonium hexafluorophosphate (n-Bu$_4$NPF$_6$) was used as supporting electrolyte, and the measurement was conducted on a film formed by dropping a solution of the compound in Example 14 on a glassy carbon electrode. Under argon gas protection, the cyclic voltammetry curves obtained by scanning were shown in FIG. 6.

The HOMO and LUMO energy levels of the solution and film of the compound in Example 14 were calculated according to the reference (Li, Y. F.; Cao, Y.; Gao, J.; Wang, D. L.; Yu, G.; Heeger, A. J. Synth. Met. 1999, 99, 243.):

The compound in Example 14 (in solution)
E (HOMO)=−5.00 eV E(LUMO)=−3.28 eV
The compound in Example 14 (in film)
E (HOMO)=−5.21 eV E(LUMO)=−3.74 eV

Example 43

Manufacturing Solar Cell Device with Compounds in Example 14 as Electron Donor

Figure 7:
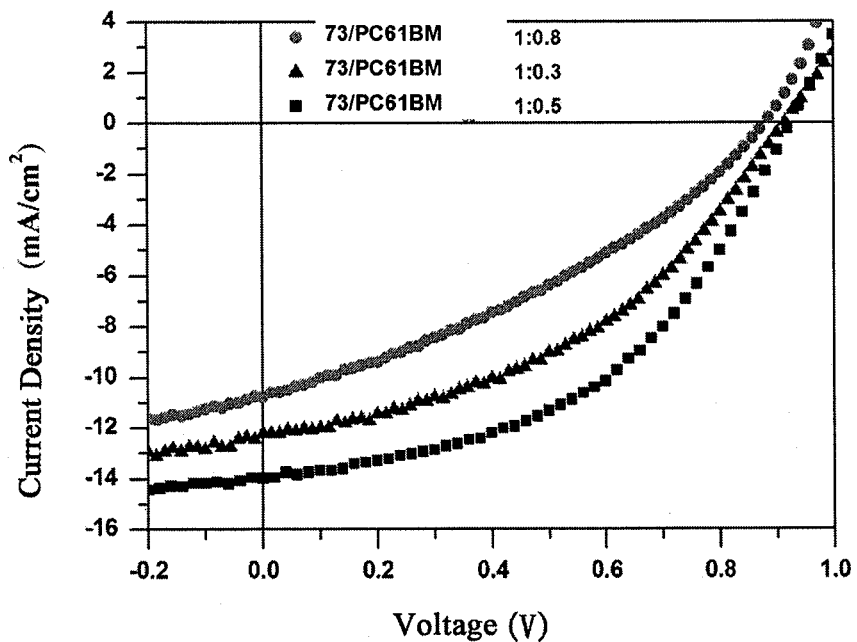
FIG. 7 shows current density versus voltage curves of the compound in Example 14 in the present application with various donor-receptor ratios.

The structure of the devices was ITO/PEDOT:PSS/donor:PC$_{61}$BM/LiF/Al, in which donor is the compound of in Example 14. The process for manufacturing the device was outlined as follows. First of all, an ITO (indium tin oxide, anode) glass was firstly pre-treated. The specific steps are the ITO glass was scrubbed with a detergent and cleaned with deionized water. The ITO glass was then ultrasonically cleaned with acetone and isopropanol each for 20 min, successively. Then, the ITO glass was placed in an oven to dry. A layer of PEDOT:PSS (Baytron P VP Al 4083) was spin coated on pre-treated ITO glass as anode modified layer (40 nm). After PEDOT:PSS was completely dried by heating at 140° C. for 20 min and cooling, a solution of a mixture of the compound in Example 14:PC$_{61}$BM in chloroform (mass ratio of the compound in Example 14:PC$_{61}$BM was 1:0.8, 1:0.5 and 1:0.3, respectively and the concentration of the compound in Example 14 was 8 mg/mL) was spin coated on the surface of PEDOT:PSS as an active layer (140 nm). LiF (0.8 nm) and metal electrode Al (60 nm) were vapor deposited. The vacuum degree was kept below 3×10$^{-4}$ Pa during vapor deposition. The devices were tested for their properties by computer-controlled Keithley 2400 digital Source Meter under standard sunlight (AM 1.5 G) illumination. The current density versus voltage curves of devices were shown in FIG. 7 and the property parameters were listed in Table 2.

TABLE 2

Comparison of Properties of Solar Cells
Manufactured with Compound in Example
14 at Different Donor-Receptor Ratios
(Light Intensity was 100 mW/cm² Measured under AM1.5G Illumination)

| | Device Parameters | | | |
|---|---|---|---|---|
| | Short-Circuit Current Density $J_{sc}$ (mA cm$^{-2}$) | Open-Circuit Voltage $V_{oc}$ (V) | Filling Factor FF (%) | Energy Conversion Efficiency PCE (%) |
| Example 14/PC$_{61}$BM (1:0.8) | 10.77 | 0.87 | 34.0 | 3.15 |
| Example 14/PC$_{61}$BM (1:0.5) | 14.02 | 0.92 | 47.4 | 6.10 |
| Example 14/PC$_{61}$BM (1:0.3) | 12.43 | 0.91 | 43.0 | 4.74 |

As seen from table 2, in the bulk heterojunction solar cell devices which were treated with a solution prepared with the compound of the invention, the ultraviolet visible absorption reaches 780 nm; the open-circuit voltage of solar devices reaches 0.90 V or more; the short-circuit current reaches 14 mA/cm² or more; and the maximum photovoltaic conversion efficiency reaches 6% or more.

Example 44

Figure 8:
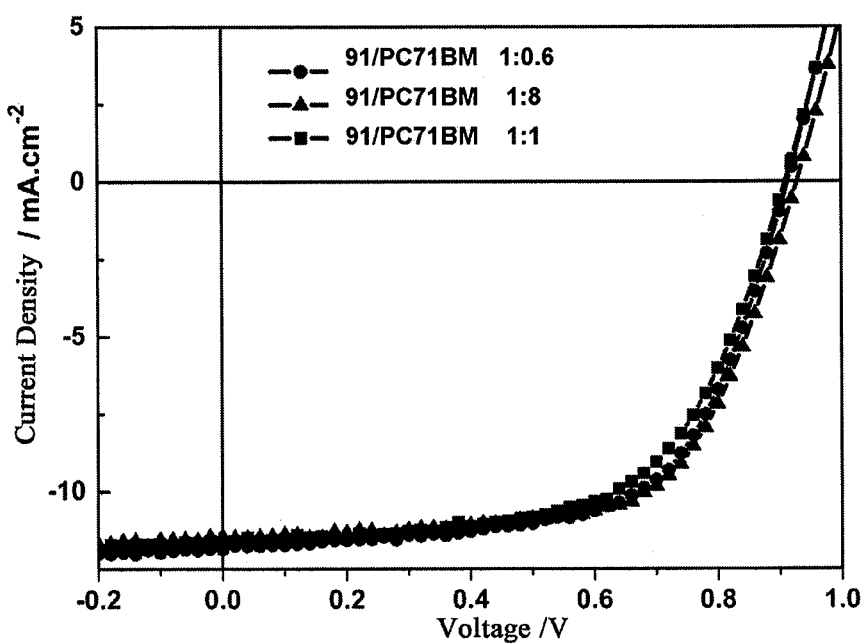
FIG. 8 shows current density versus voltage curves of the compound in Example 25 in the present application with various donor-receptor ratios.

Manufacture and Tests of Solar Cell Devices Having Compound in Example 25 as Electron Donor The structure of the devices was ITO/PEDOT:PSS/91: $PC_{71}BM$/LiF/Al. The cleaning process of an ITO glass and spin coating process of PSS-PEDOT were identical to those in Example 43. After PEDOT:PSS was completely dried by heating at 140° C. for 20 min and cooling, a solution of a mixture of 91:$PC_{71}BM$ in chloroform (mass ratio of 91:$PC_{71}BM$ was 1:0.6, 1:0.8 and 1:0.1, respectively) was spin coated on the surface of PEDOT:PSS as an active layer (80 nm). LiF (0.8 nm) and metal electrode Al (60 nm) were vapor deposited. The vacuum degree was kept below $3 \times 10^{-4}$ Pa during vapor deposition. The devices were tested for their properties by computer-controlled Keithley 2400 digital Source Meter under standard sunlight (AM 1.5 G) illumination. The current density versus voltage curves of devices were shown in FIG. 8 and the property parameters were listed in Table 3.

TABLE 3

Comparison of Properties of Solar Cells Manufactured with Compound in Example 25 at Different Donor-Receptor Ratios
(Light Intensity was 100 mW/cm² Measured under AM1.5G Illumination)

| | Device Parameters | | | |
|---|---|---|---|---|
| | Short-Circuit Current Density $J_{sc}$ (mA cm$^{-2}$) | Open-Circuit Voltage $V_{oc}$ (V) | Filling Factor FF (%) | Energy Conversion Efficiency PCE (%) |
| Example 25/$PC_{71}BM$ (1:0.6) | 0.91 | 11.87 | 0.62 | 6.74 |
| Example 25/$PC_{71}BM$ (1:0.8) | 0.93 | 11.44 | 0.65 | 6.88 |
| Example 25/$PC_{71}BM$ (1:1) | 0.91 | 11.63 | 0.61 | 6.41 |

Figure 9:
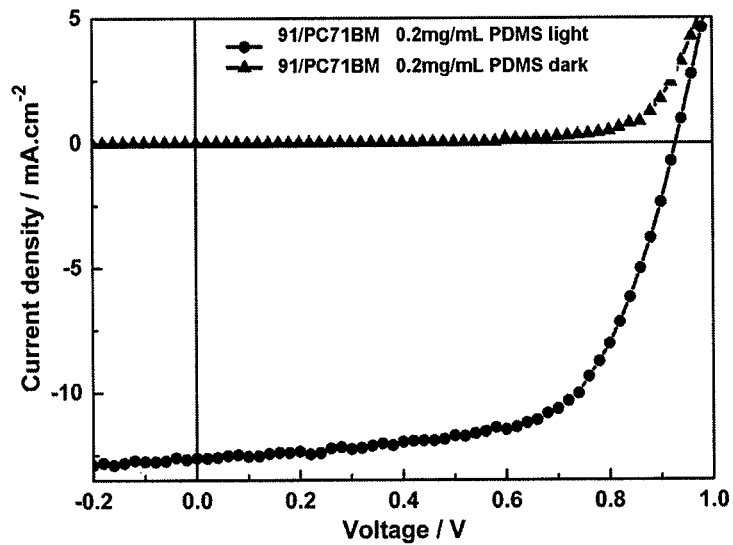
FIG. 9 shows current density versus voltage curves of the compound in Example 25 in the present application and $C_{71}PCBM$ with weight ratio of 1:0.8, wherein PDMS is added.
Figure 10:
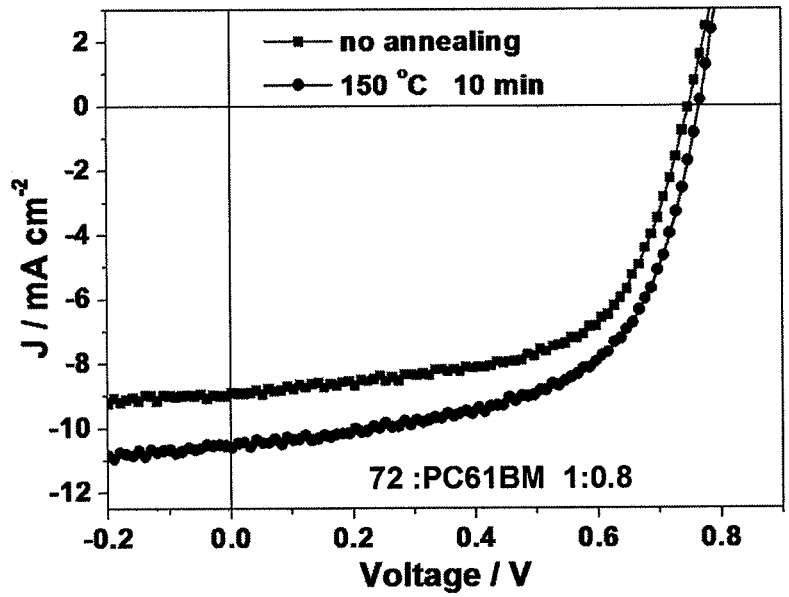
FIG. 10 shows current density versus voltage curves of the compound in Example 13 in the present application and $C_{61}PCBM$ with weight ratio of 1:0.8.
Figure 11:
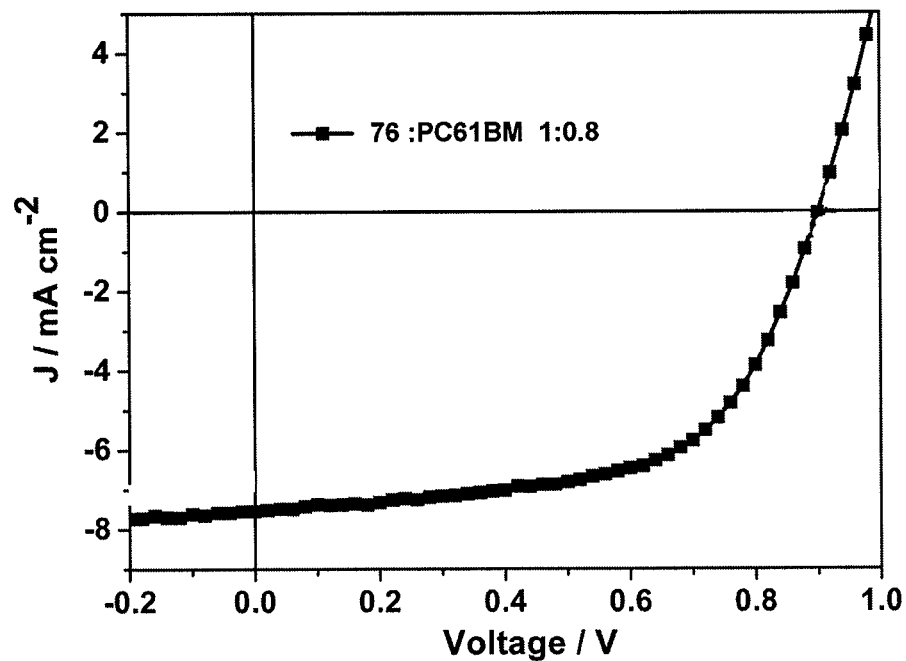
FIG. 11 shows current density versus voltage curves of the compound in Example 17 in the present application and $C_{61}PCBM$ with weight ratio of 1:0.8.
Figure 12:
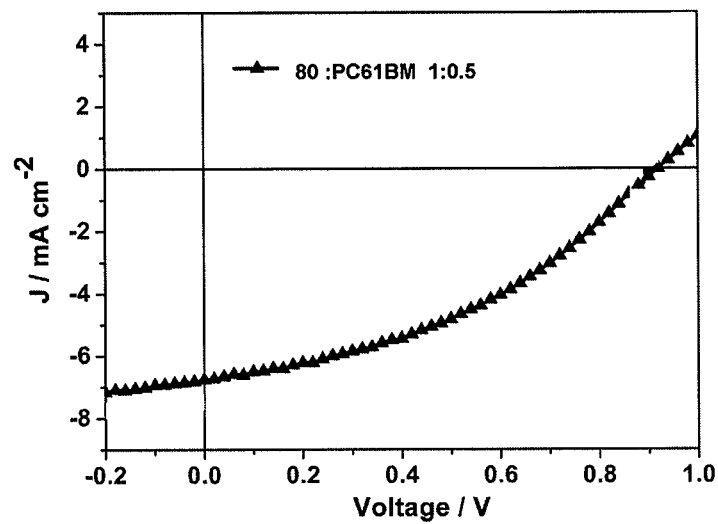
FIG. 12 shows current density versus voltage curves of the compound in Example 21 in the present application and $C_{61}PCBM$ with weight ratio of 1:0.5.
Figure 13:
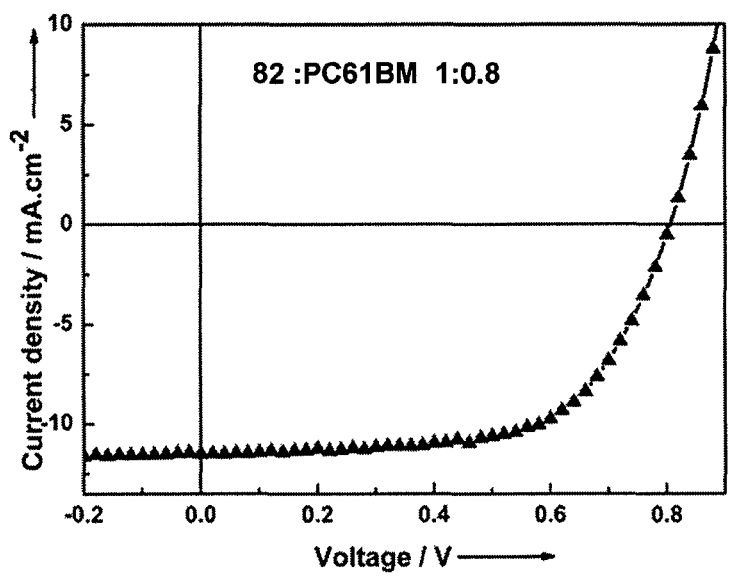
FIG. 13 shows current density versus voltage curves of the compound in Example 23 in the present application and $C_{61}PCBM$ with weight ratio of 1:0.8.
Figure 14:
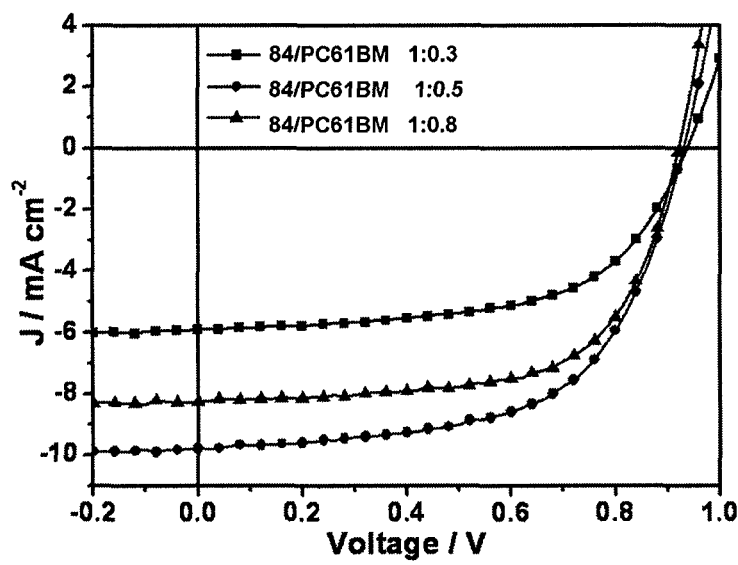
FIG. 14 shows current density versus voltage curves of the compound in Example 24 in the present application and $C_{61}PCBM$ with various weight ratios.
Figure 15:
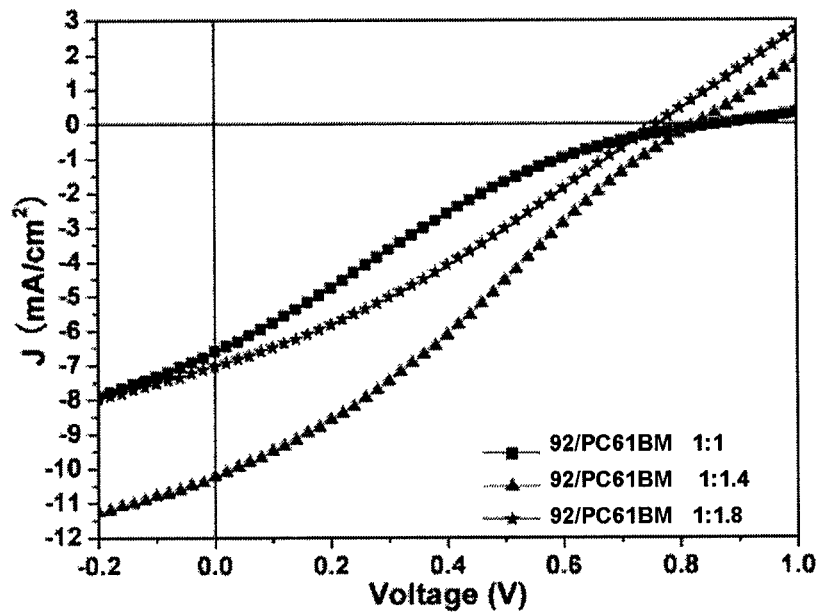
FIG. 15 shows current density versus voltage curves of the compound in Example 27 in the present application and $C_{61}PCBM$ with various weight ratios.
Figure 16:
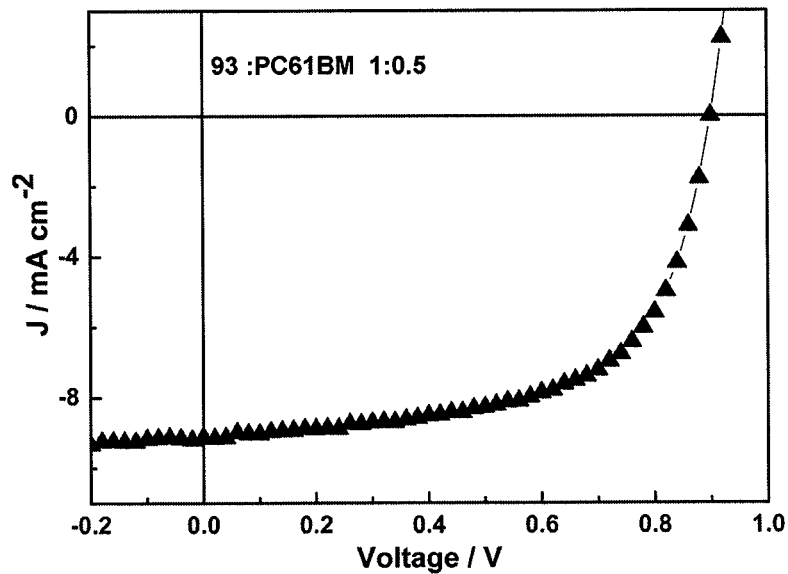
FIG. 16 shows current density versus voltage curves of the compound in Example 28 in the present application and $C_{61}PCBM$ with weight ratio of 1:0.5.
Figure 17:
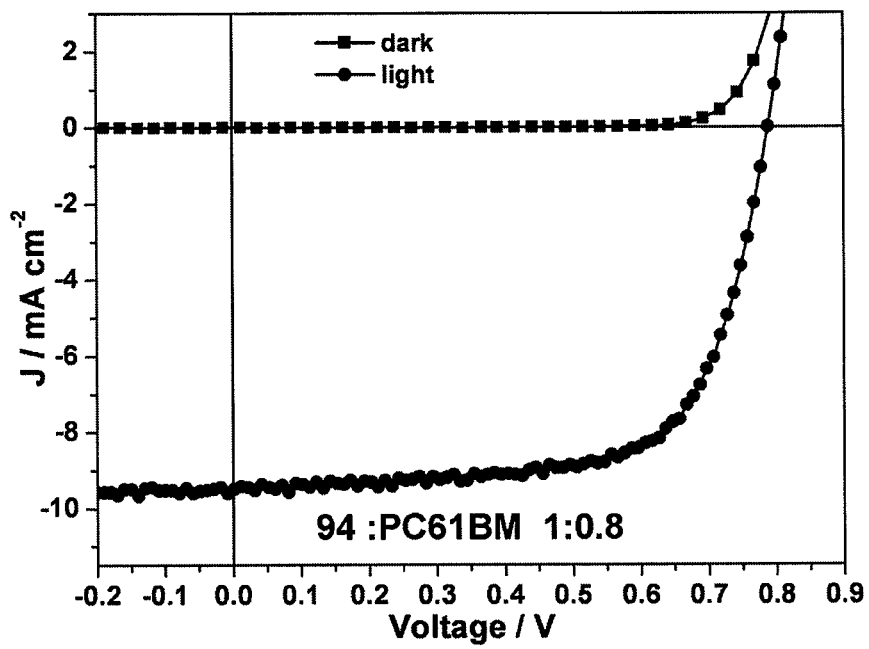
FIG. 17 shows current density versus voltage curves of the compound in Example 29 in the present application and $C_{61}PCBM$ with weight ratio of 1:0.8.
Figure 18:
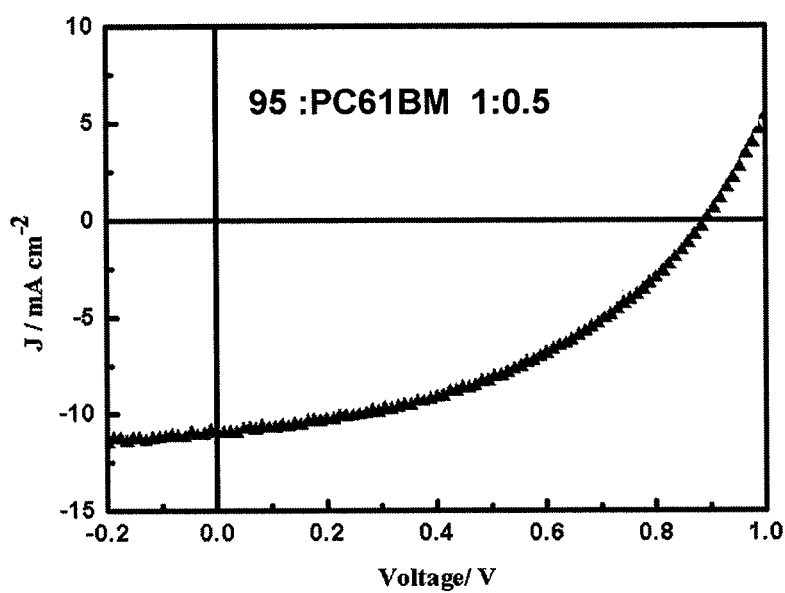
FIG. 18 shows current density versus voltage curves of the compound in Example 30 in the present application and $C_{61}PCBM$ with weight ratio of 1:0.5.
Figure 19:
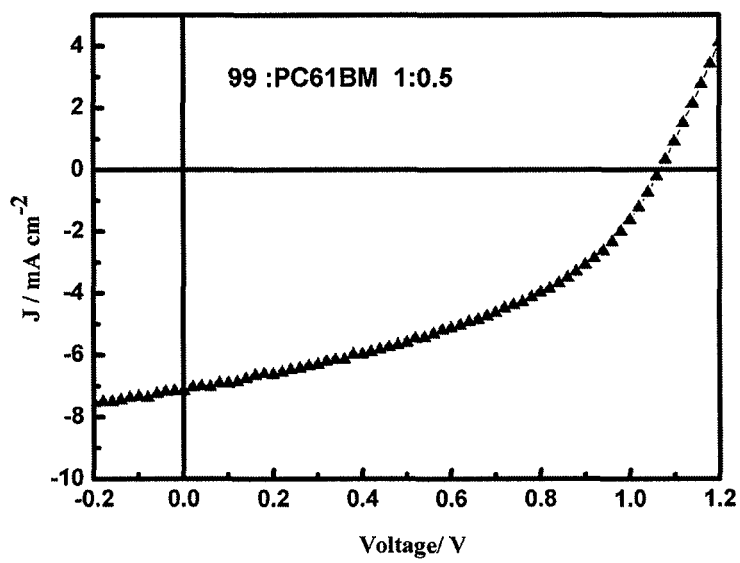
FIG. 19 shows current density versus voltage curves of the compound in Example 34 in the present application and $C_{61}PCBM$ with weight ratio of 1:0.5.
Figure 20:
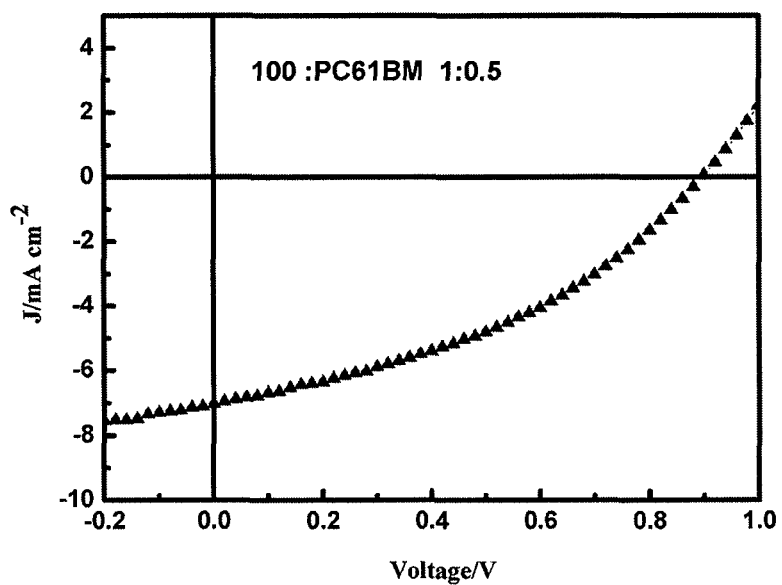
FIG. 20 shows current density versus voltage curves of the compound in Example 35 in the present application and $C_{61}PCBM$ with weight ratio of 1:0.5.

In addition, in the mixing process of the active layer of the above devices, addition of a small amount of polydimethylsiloxane (PDMS) made energy conversion efficiency further increase to 7.46%. The current density versus voltage curve was shown in FIG. 9 and the specific data were shown in Table 4.

TABLE 4

Comparison of Properties of Solar Cells Having Different Amounts of PDMS and Active Layer of Compound in Example 25-$C_{71}$PCBM (1:0.8)
(Light Intensity was 100 mW/cm² measured under AM1.5G Illumination)

| PDMS (mg/mL) | Short-Circuit Current Density $J_{sc}$ (mA cm$^{-2}$) | Open-Circuit Voltage $V_{oc}$ (V) | Filling Factor FF (%) | Energy Conversion Efficiency PCE (%) |
|---|---|---|---|---|
| 0.1 | 0.92 | 11.84 | 0.65 | 7.09 |
| 0.2 | 0.93 | 12.62 | 0.64 | 7.46 |
| 0.3 | 0.92 | 11.64 | 0.64 | 6.81 |

Example 45

Manufacturing Organic Solar Cell Devices with Compounds in Examples 13, 17, 21, 23, 24, 27, 28, 29, 30, 34 and 35 as Electron Donors The cleaning process of ITO glass and spin coating process of PSS-PEDOT were identical to those in Example 43. After PEDOT:PSS was completely dried by heating at 140° C. for 20 min and cooling, a solution of a mixture of donor:$PC_{61}BM$ in chloroform was spin coated on the surface of PEDOT:PSS as an active layer. LiF (0.8 nm) and metal electrode Al (60 nm) were vapor deposited. The vacuum degree was kept below $3 \times 10^{-4}$ Pa during vapor deposition. The devices were tested for their properties by computer-controlled Keithley 2400 digital Source Meter under standard sunlight (AM 1.5 G) illumination. The current density versus voltage curves of devices were shown in FIGS. 10 to 21 and the property parameters were listed in Table 5.

TABLE 5

Comparison of Properties of Organic Solar Cell Devices Manufactured with Compounds in Examples 13, 17, 21, 23, 24, 27, 28, 29, 30, 34 and 35 as Donors
(Light Intensity was 100 mW/cm² Measured under AM1.5G Illumination)

| Compounds | Short-Circuit Current Density $J_{sc}$ (mA cm$^{-2}$) | Open-Circuit Voltage $V_{oc}$ (V) | Filling Factor FF (%) | Energy Conversion Efficiency PCE (%) |
|---|---|---|---|---|
| Example 13 | 10.06 | 0.77 | 58.4 | 4.52 |
| Example 17 | 7.54 | 0.90 | 59.6 | 4.05 |
| Example 21 | 6.77 | 0.92 | 39.4 | 2.46 |
| Example 23 | 11.51 | 0.80 | 63.4 | 5.84 |
| Example 24 | 9.77 | 0.93 | 59.9 | 5.44 |
| Example 27 | 10.23 | 0.82 | 29.2 | 2.45 |
| Example 28 | 9.13 | 0.90 | 61.6 | 5.06 |
| Example 29 | 9.51 | 0.79 | 68.3 | 5.13 |
| Example 30 | 13.08 | 0.89 | 39.5 | 4.60 |
| Example 34 | 7.2 | 1.06 | 42.6 | 3.25 |
| Example 35 | 7.0 | 0.90 | 38.7 | 2.44 |

In view of the above, in the bulk heterojunction solar cell devices which were treated with a solution prepared with the compounds of the invention, the maximum photovoltaic conversion efficiency reaches 7% or more. Moreover, the compounds of the present invention have accurate molecular weights, controlled structures, easiness to purify, and is useful for manufacturing high performance organic solar cells having high open-circuit voltage, good stability, flexibility and large area.

From the foregoing it will be appreciated that, although specific embodiments of the invention have been described herein for purpose of illustration, various variants or modifications may be made by a person having ordinary skill in the art without deviating from the spirit and scope of the invention. These variants or modifications should fall within the scope of the pending claims in the present application.

The invention claimed is:

1. A donor-receptor type oligothiophene compound selected from the group consisting of general formulae (1) to (6):

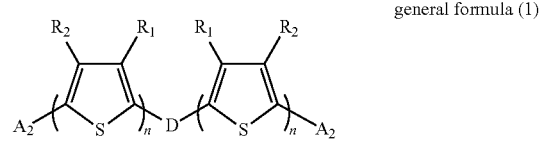

general formula (1)

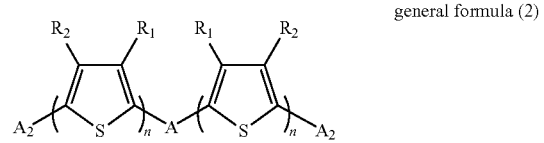

general formula (2)

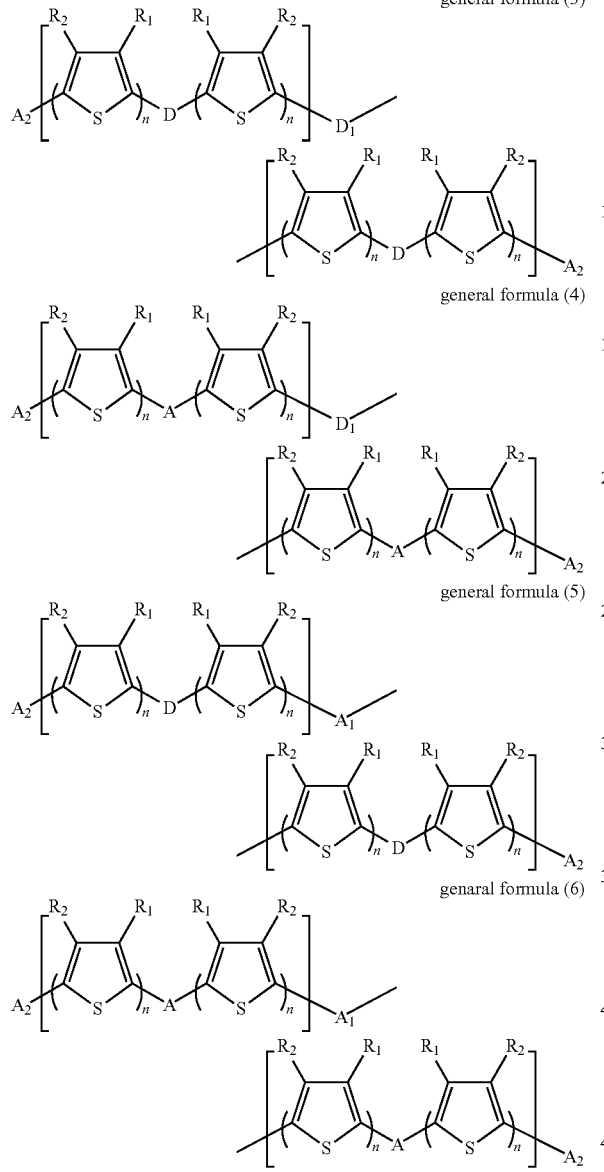

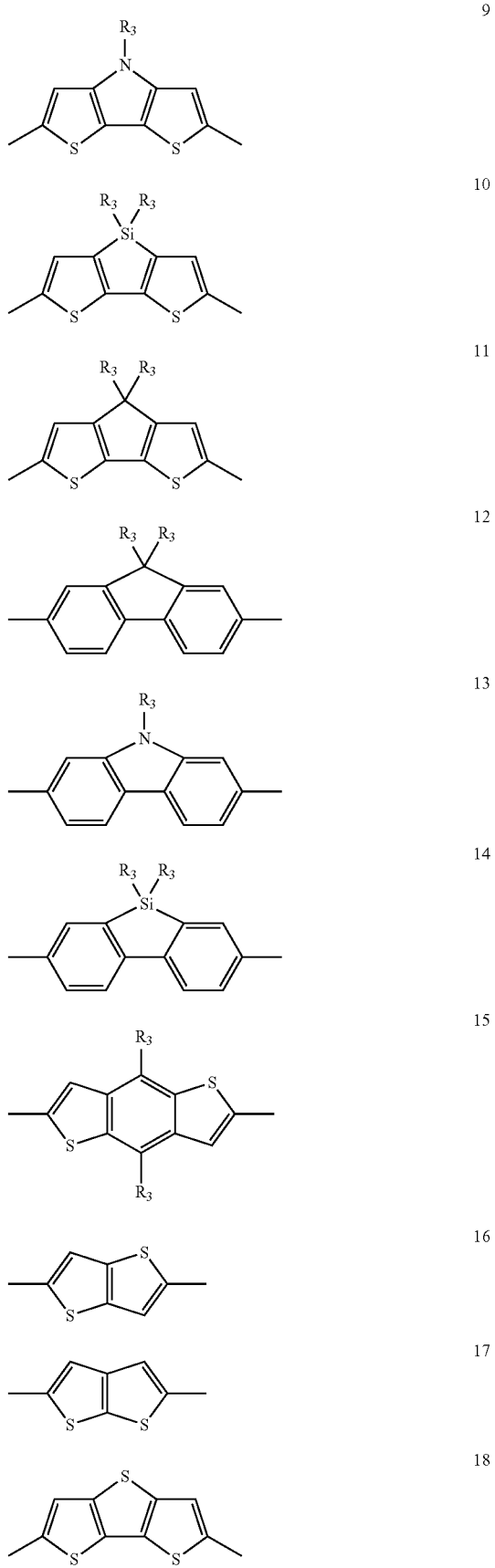

wherein n is an integer of 1 to 50;

$R_1$ and $R_2$ are each independently selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, wherein $R_1$ and $R_2$ may be identical or different, but $R_1$ and $R_2$ are not H simultaneously;

D and $D_1$ are each independently selected from the group consisting of group 7 to group 20:

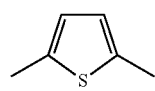

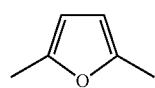

-continued

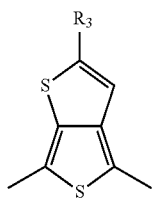
19

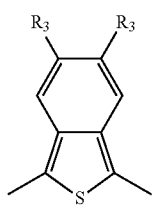
20 wherein R₃ is selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof;

A and $A_1$ are each independently selected from the group consisting of group 21 to group 30:

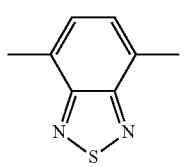
21

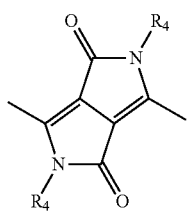
22

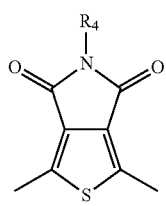
23

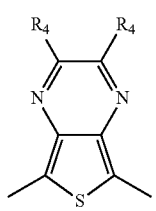
24

-continued

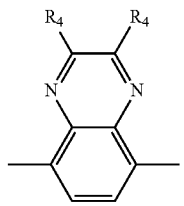
25

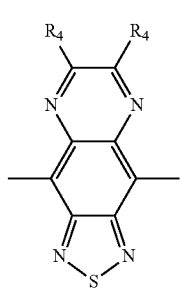
26

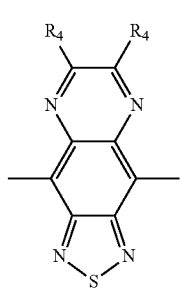
27

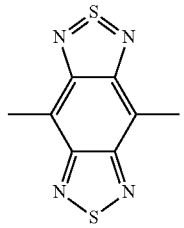
28

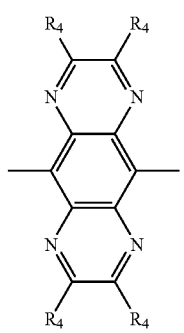
29

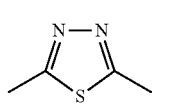
30

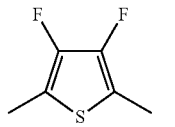

wherein $R_4$ is selected from the group consisting of $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof; and $A_2$ is selected from the group consisting of group 31 to group 60:

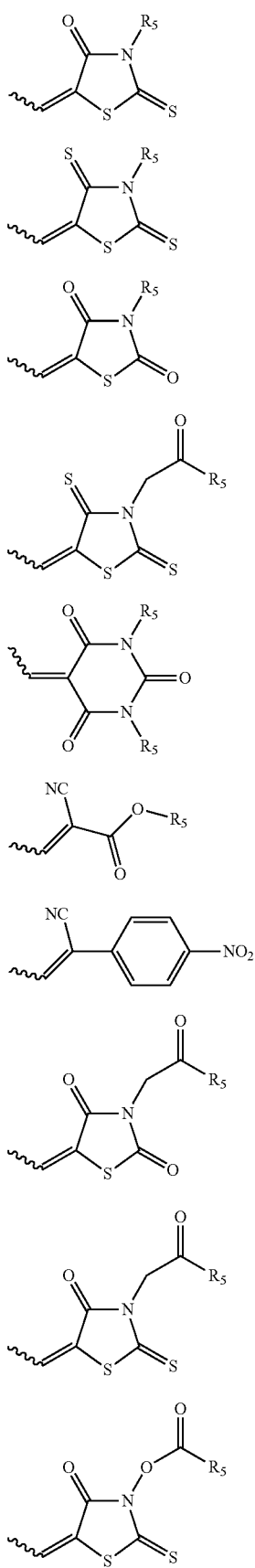
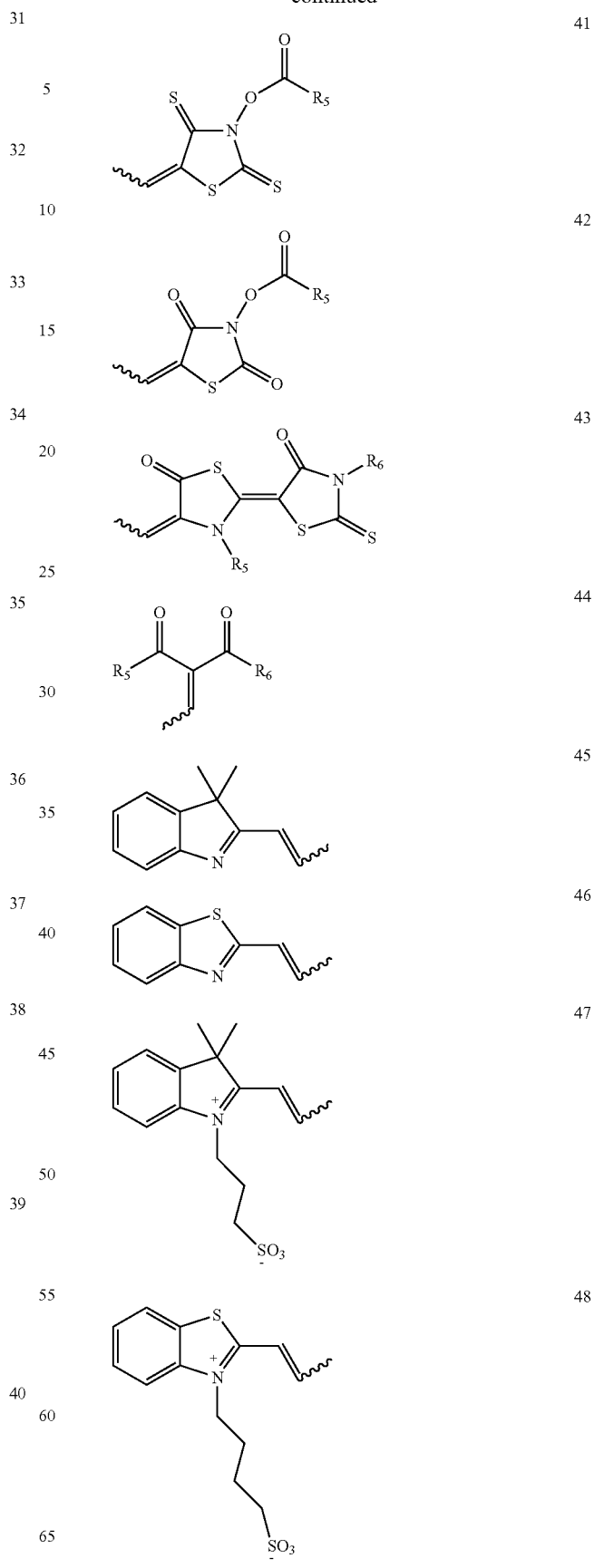

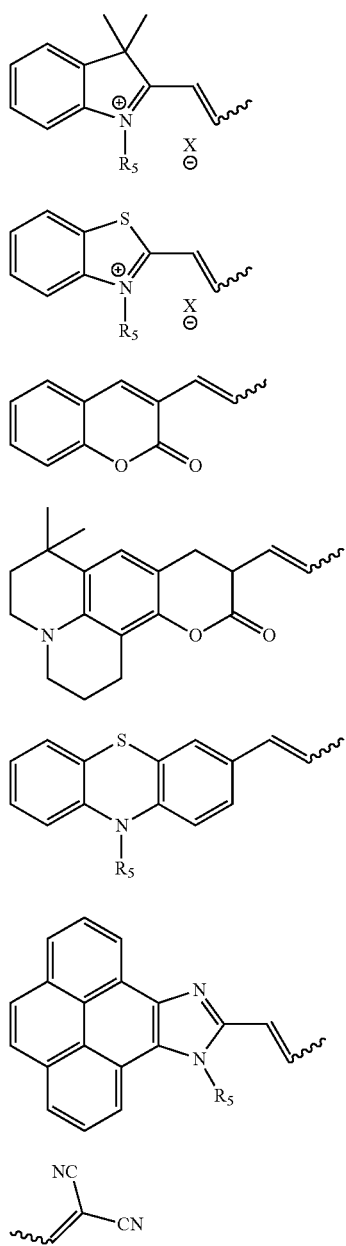

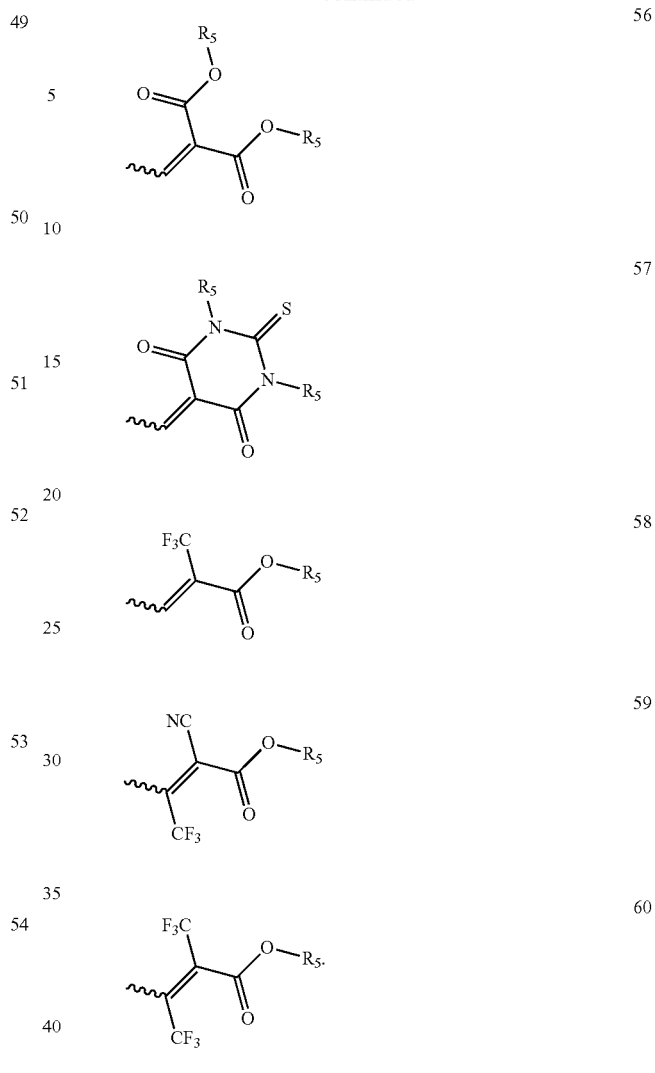

wherein, $R_5$ and $R_6$ are each independently selected from the group consisting of $C_1$-$C_{30}$ alkyl, $C_3$-$C_{30}$ cycloalkyl, $C_1$-$C_{30}$ alkoxy and halo-substituted derivatives thereof, and $X^-$ is an anion such that $A_2$ can be a neutral group, and when $A_2$ group 55, n in the general formula (1) is 4 or more.

2. The compound of claim 1, wherein the compound is selected from the group consisting of:

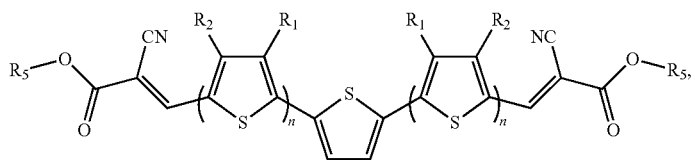

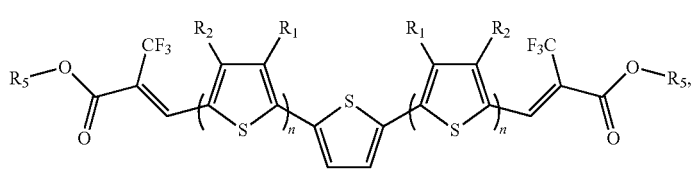

-continued
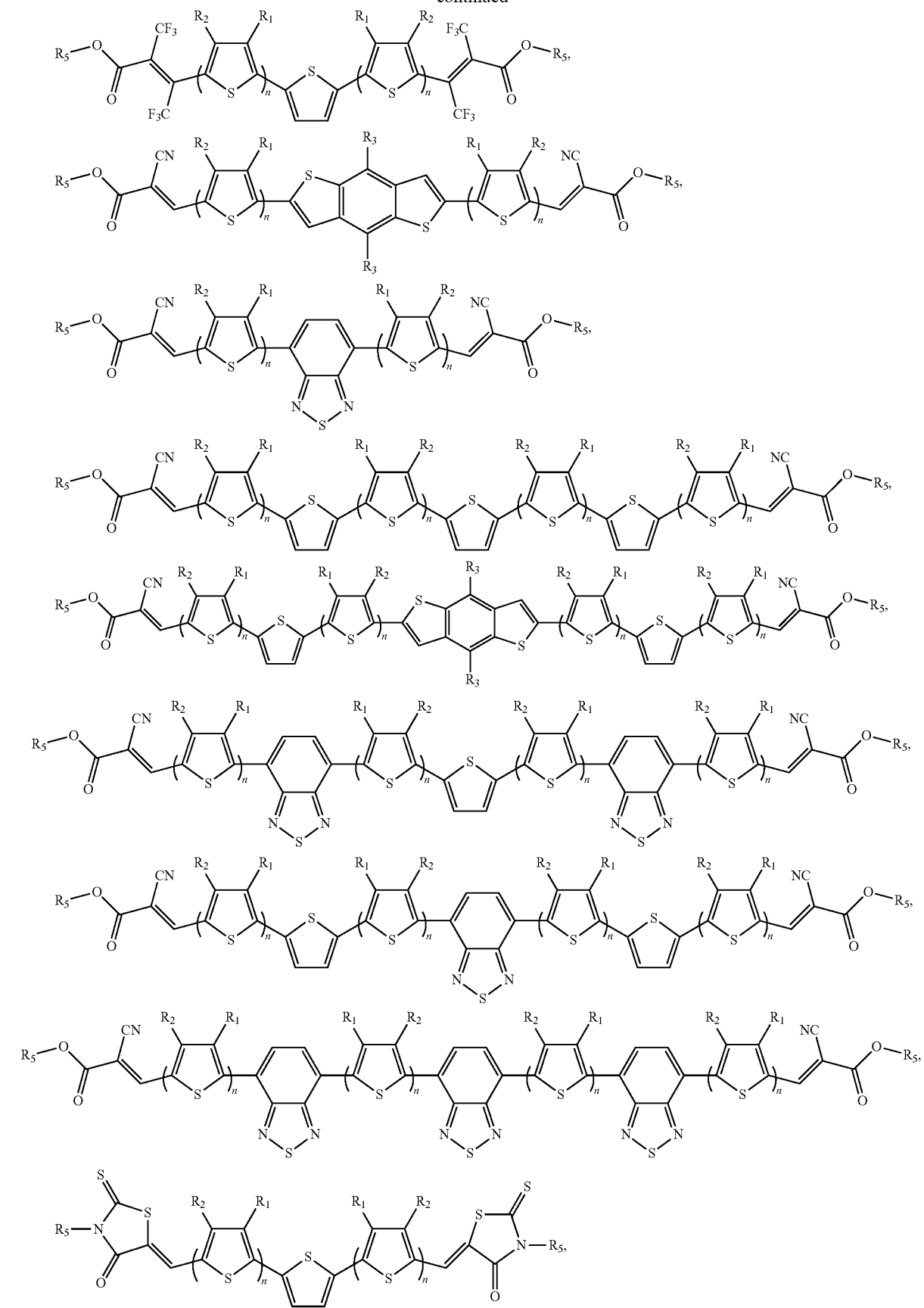

-continued
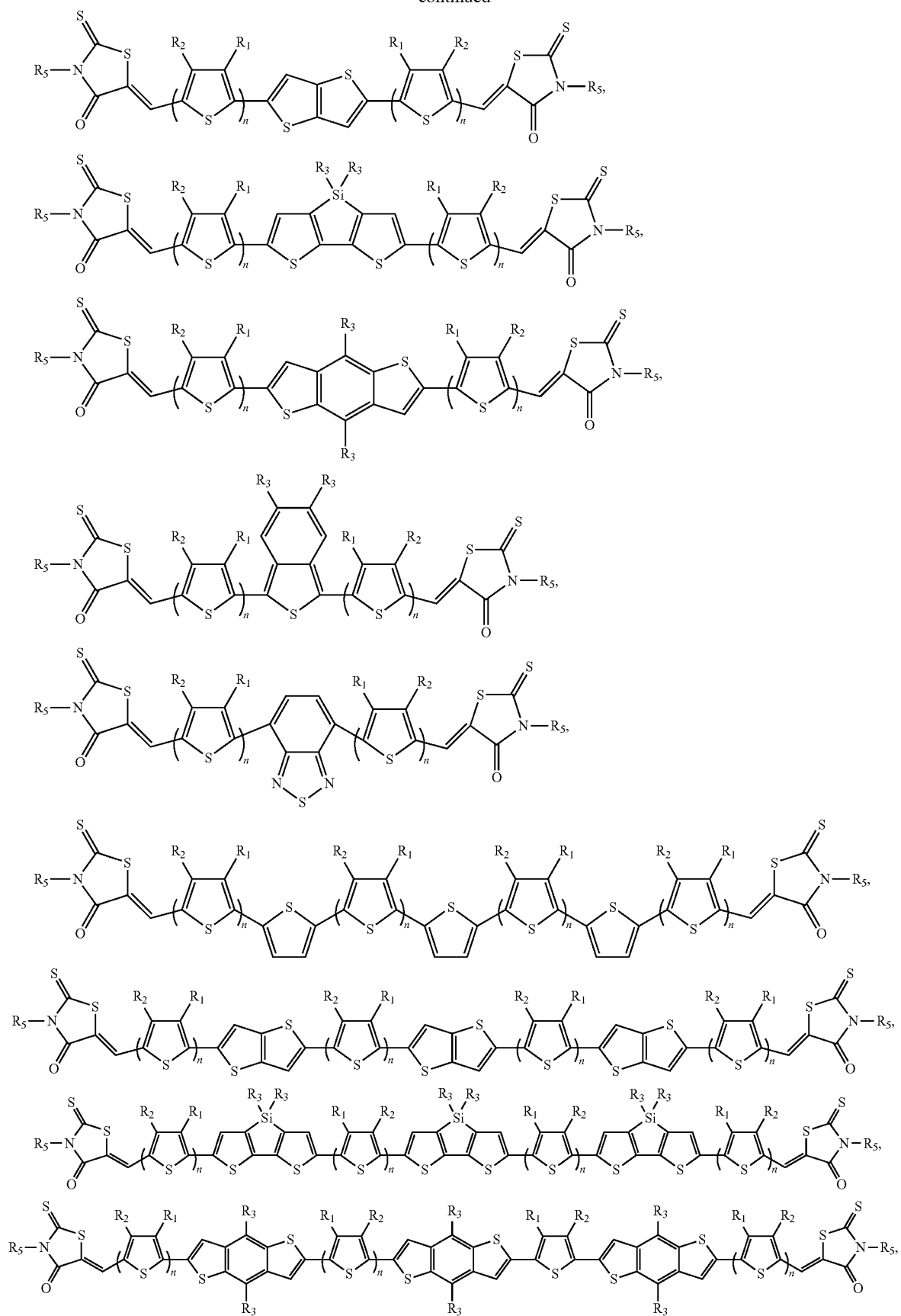

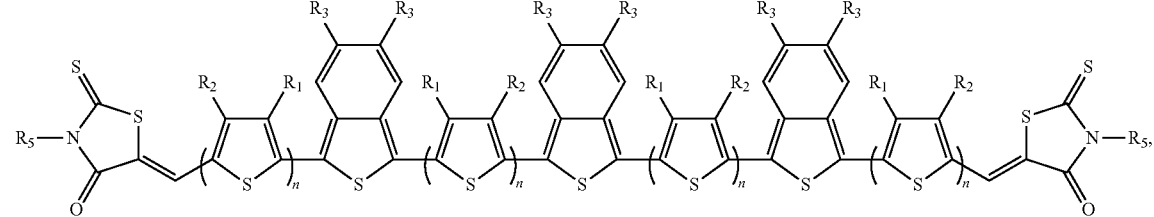
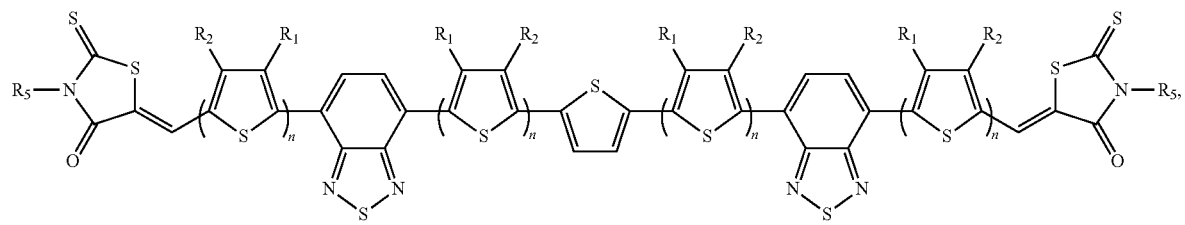
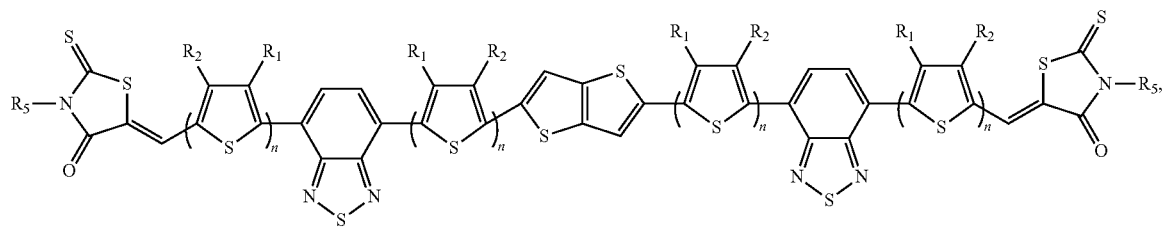
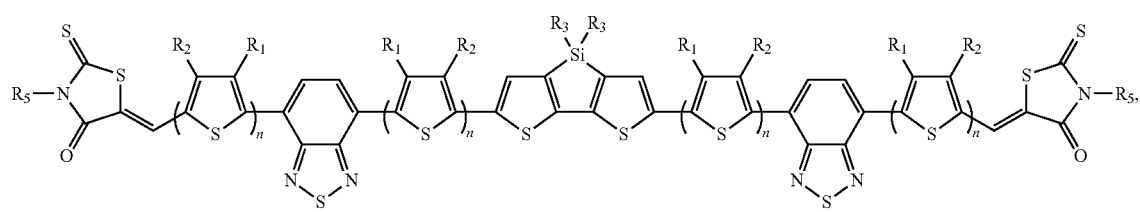
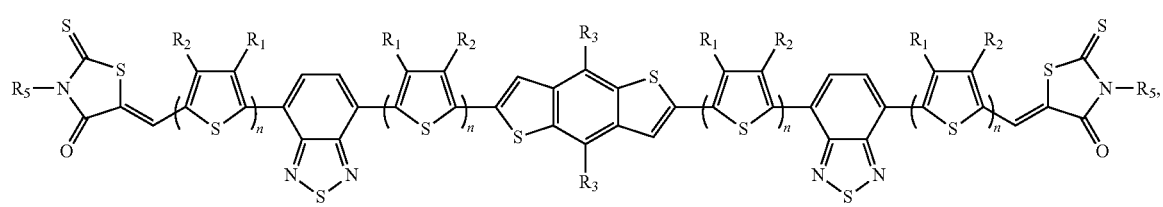
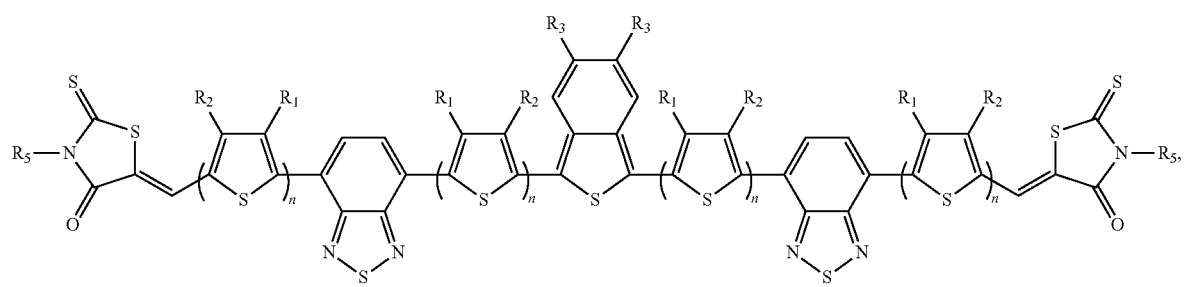
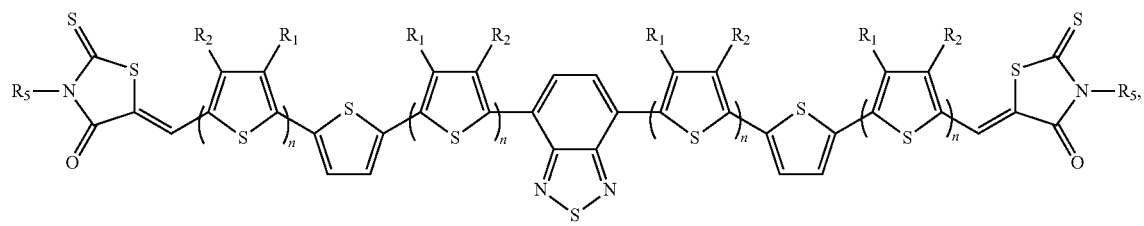

-continued

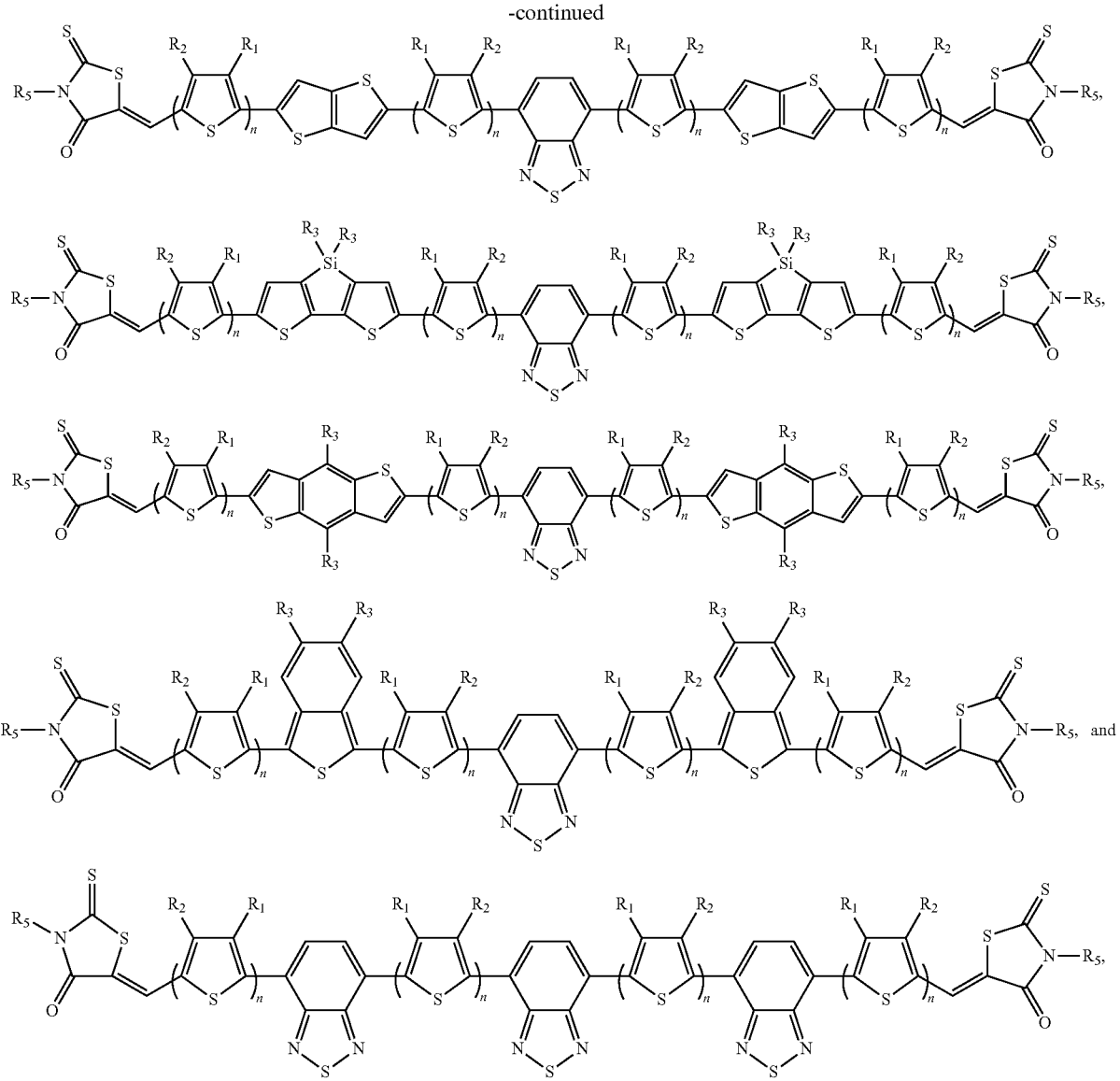

wherein n is an integer of 1 to 50;

$R_1$ and $R_2$ are each independently selected from the group consisting of H, $C_1$-$C_{30}$ alkyl, $C_3$-$C_{30}$ cycloalkyl, $C_1$-$C_{30}$ alkoxy, $C_1$-$C_{30}$ carboxylic ester group and halo-substituted derivatives thereof, wherein $R_1$ and $R_2$ may be identical or different, but $R_1$ and $R_2$ are not H simultaneously;

$R_3$ is selected from the group consisting of H, $C_1$-$C_{30}$ alkyl, $C_3$-$C_{30}$ cycloalkyl, $C_1$-$C_{30}$ alkoxy and halo-substituted derivatives thereof, and $R_5$ is selected from the group consisting of $C_1$-$C_{30}$ alkyl, $C_3$-$C_{30}$ cycloalkyl, $C_1$-$C_{30}$ alkoxy and halo-substituted derivatives thereof.

3. The compound of claim 1, wherein n is an integer of 1 to 30.

4. The compound of claim 1, wherein $X^-$ is selected from the group consisting of a halogen ion, $BF_4^-$, $PF_6^-$, $SO_3^-$ and $CF_3SO_3^-$.

5. The compound claim 1, which is selected from the group consisting of:

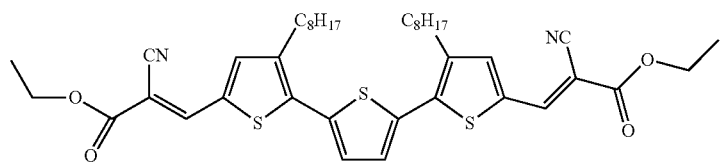

-continued
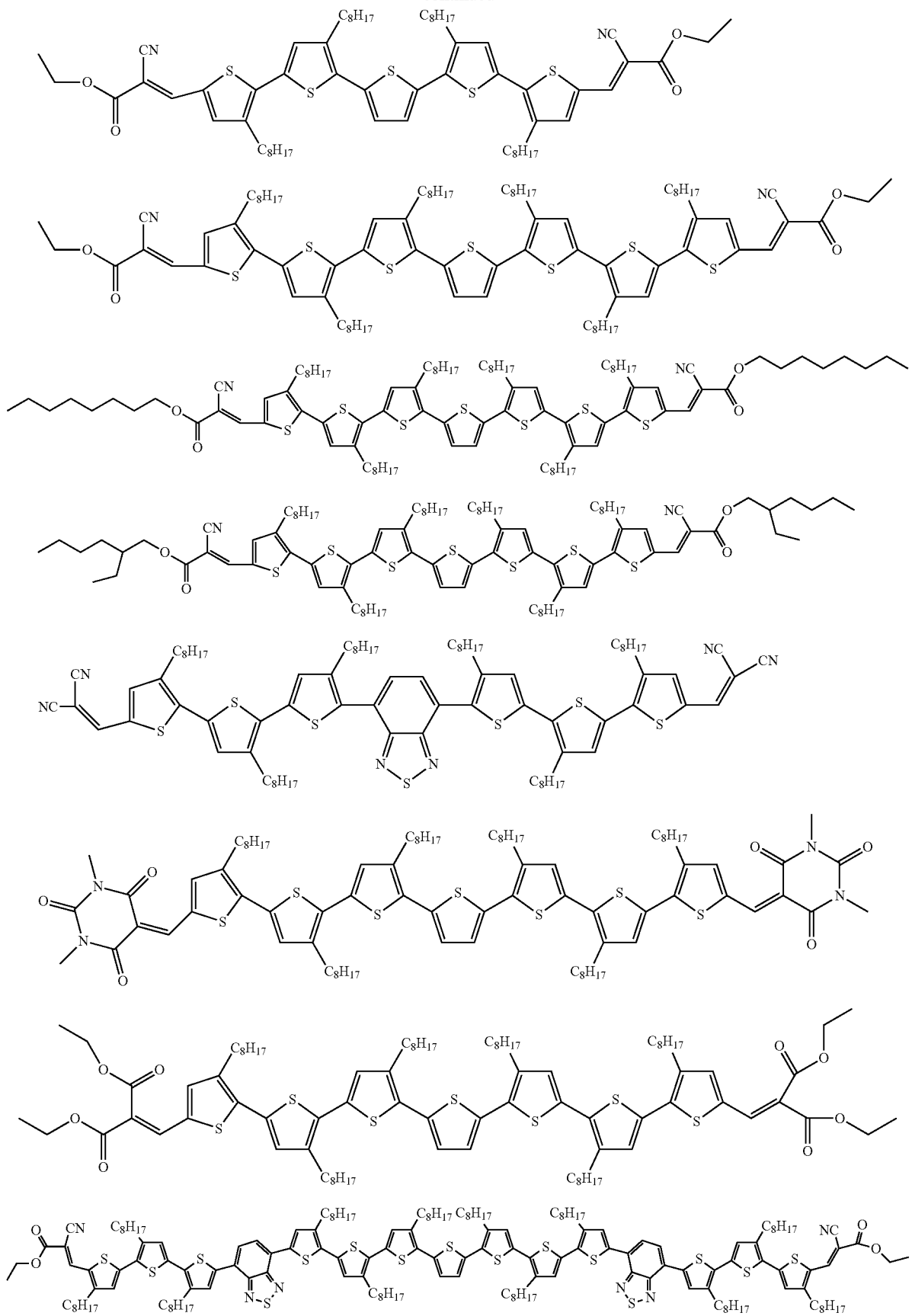

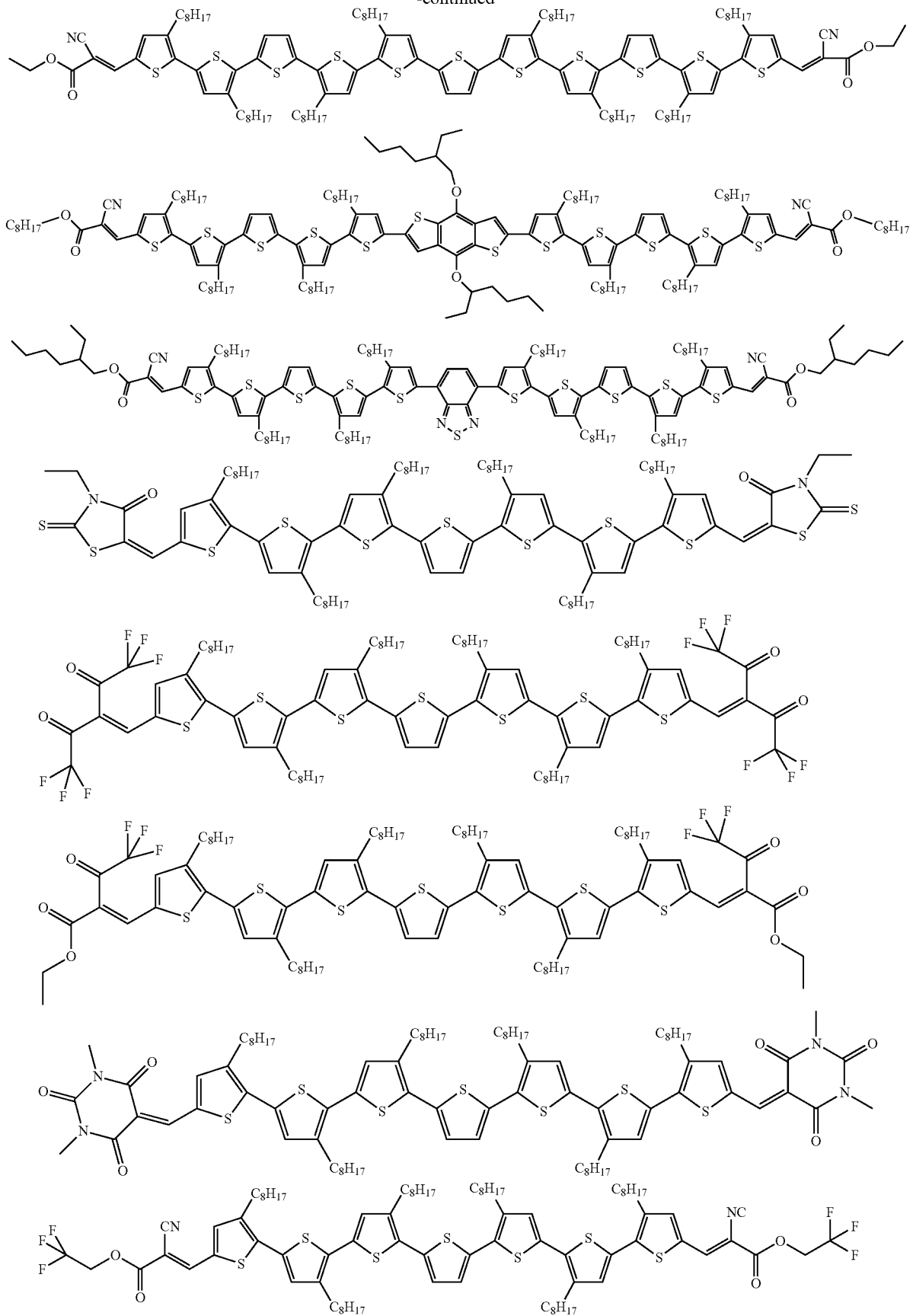

-continued
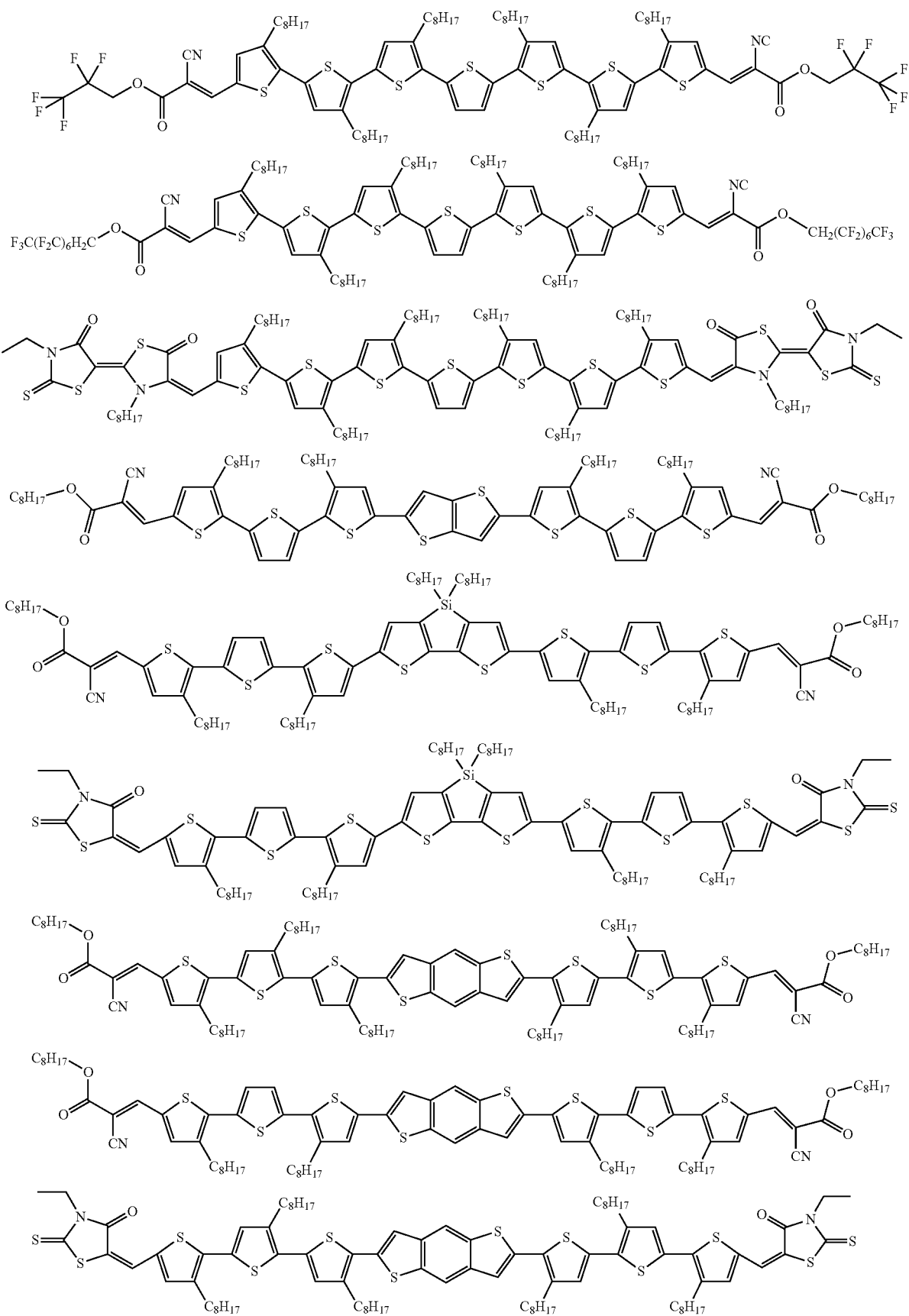

-continued
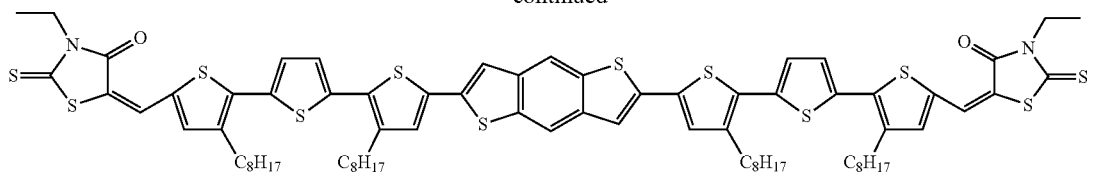
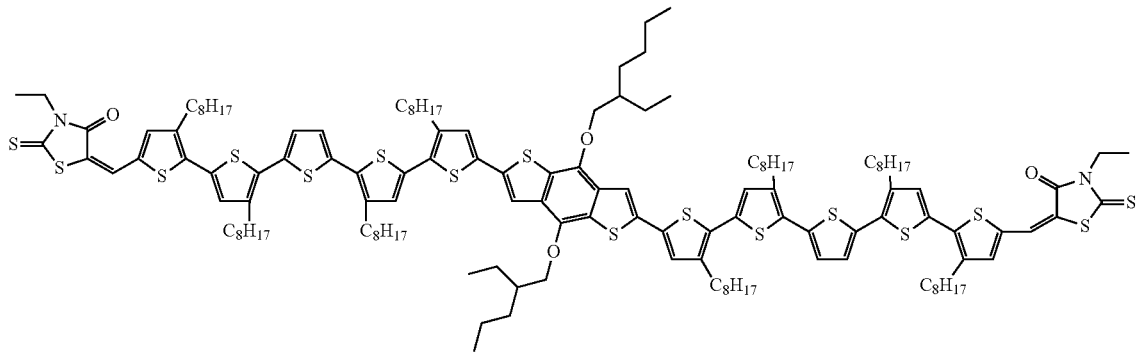
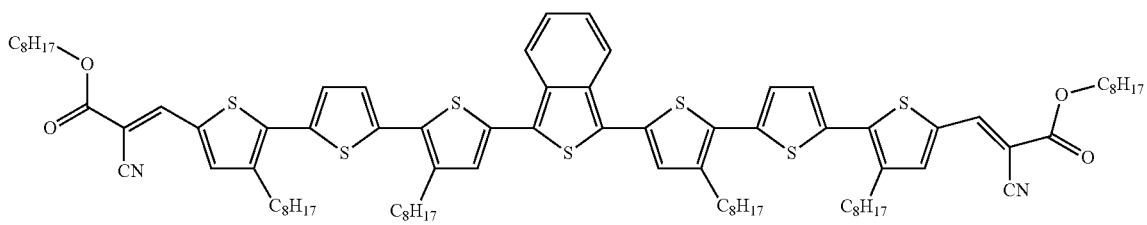
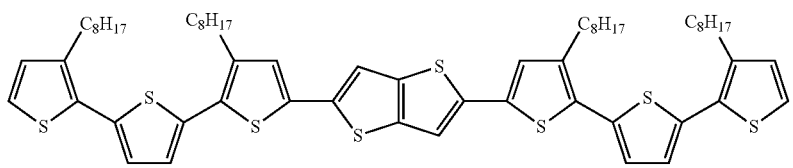
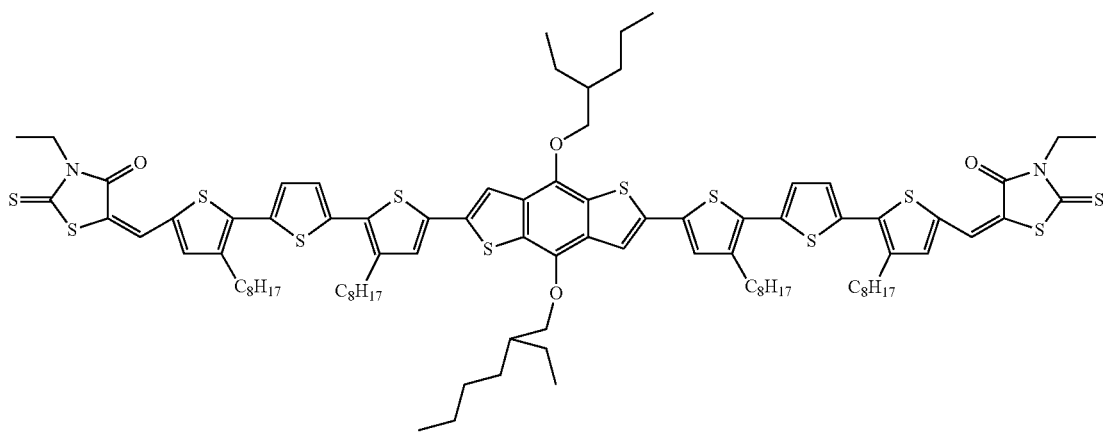
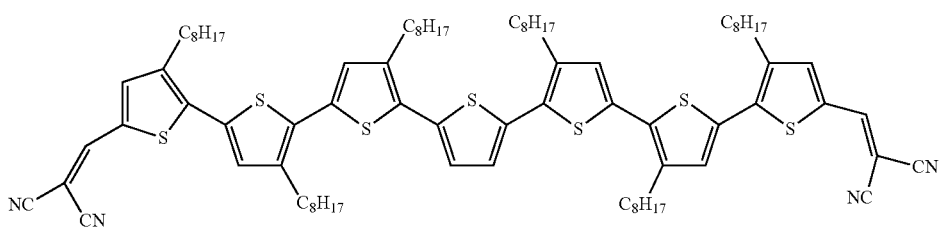

-continued
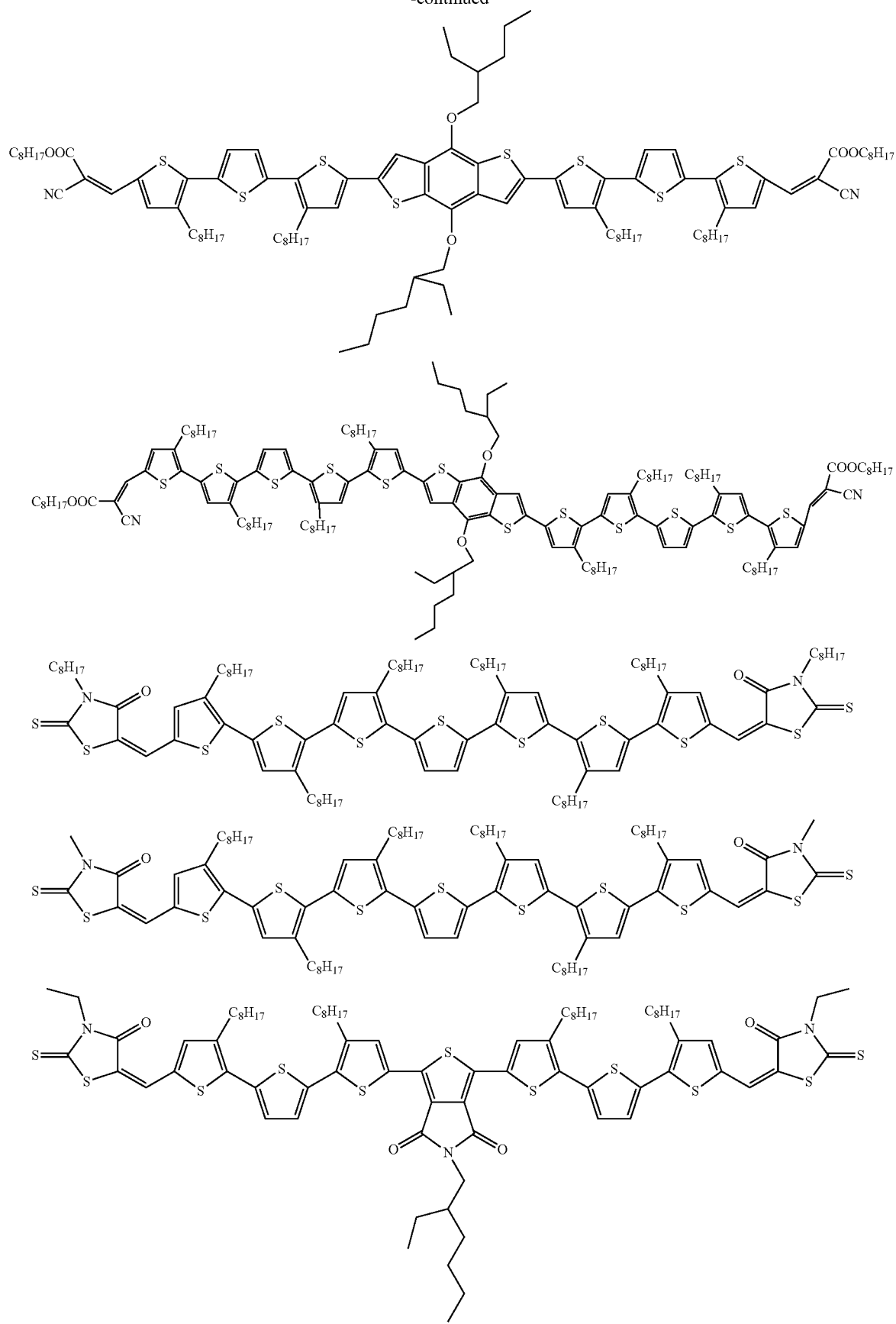

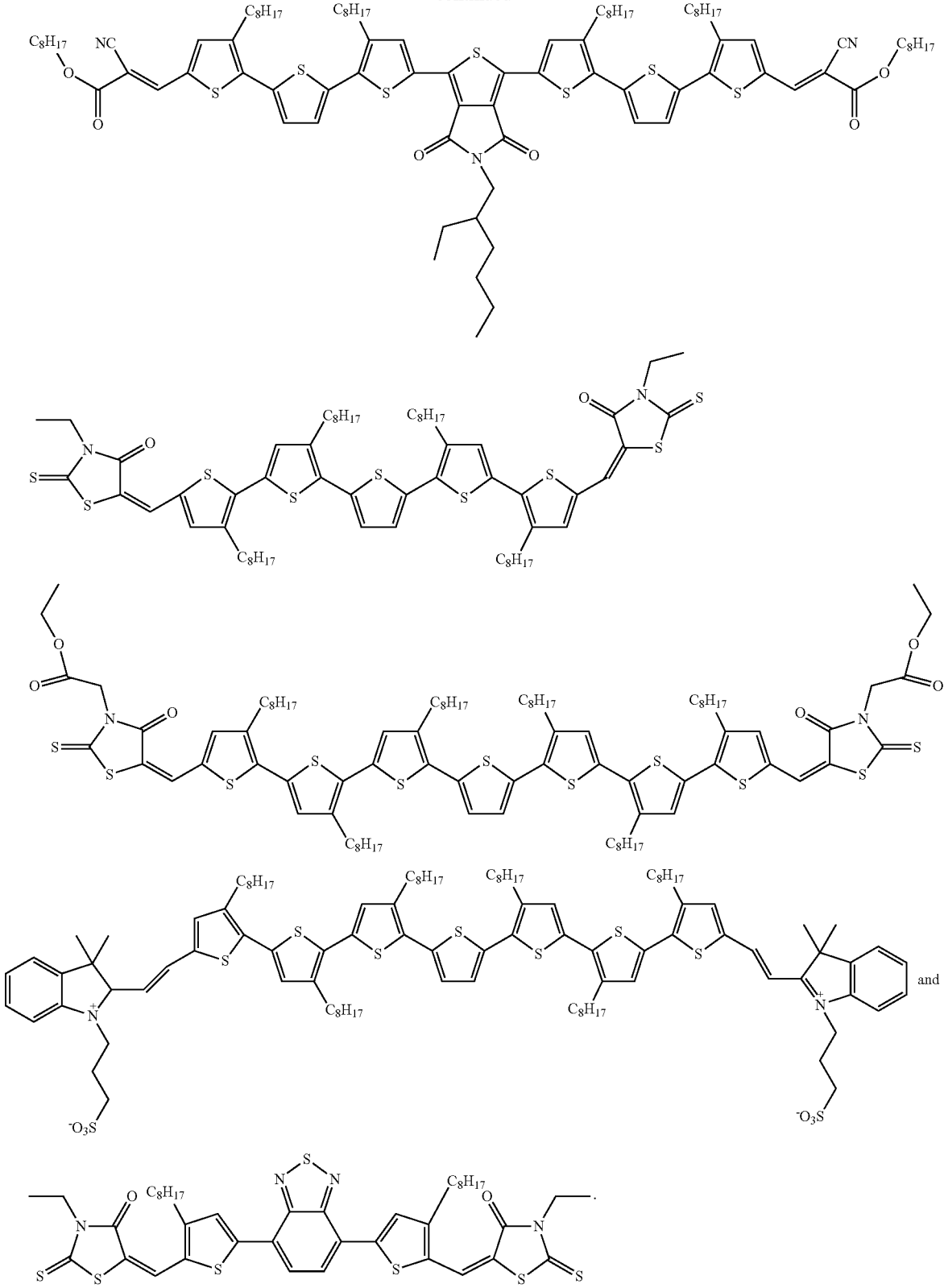
6. A process for preparing the compound of claim 1, comprising carrying out a Knoevenagel condensation reaction of a donor bridged oligothiophene comprising a receptor terminal with a receptor terminal monomer through a bisaldehyde group donor bridged oligothiophene in the presence of a solvent and a catalyst to obtain the compound.

7. The process of claim 6, wherein the catalyst is an alkaline compound.

8. The process of claim 6, wherein the process is carried out under a protective gas.

9. A process for preparing the compound of claim 1, comprising carrying out a Knoevenagel condensation reaction of a donor bridged oligothiophene comprising a small molecule dye terminal with an organic small molecule dye monomer through a bisaldehyde group donor bridged oligothiophene in the presence of a solvent and a catalyst to obtain the compound.

10. The process of claim 9, wherein the catalyst is an acidic catalyst.

11. The process of claim 9, wherein the solvent is an acidic solution.

12. The process of claim 9, wherein the catalyst is present in an excessive amount.

13. A triode device comprising an active layer comprising the compound of claim 1.

14. A photovoltaic device comprising an active layer comprising the compound of claim 1.

15. The photovoltaic device of claim 14, wherein the photovoltaic device is a solar cell device.

16. A process for manufacturing a field effect transistor, comprising providing a donor-receptor type oligothiophene compound comprising the terminal receptor unit of claim 1.

17. A process for manufacturing a photovoltaic device, comprising providing a donor-receptor type oligothiophene compound comprising the terminal receptor unit of claim 1.

18. The process of claim 17, wherein the photovoltaic device is a solar cell device.

19. The process of claim 18, comprising providing the compound for the manufacture of an active layer of the solar cell device.

20. A compound selected from the group consisting of:

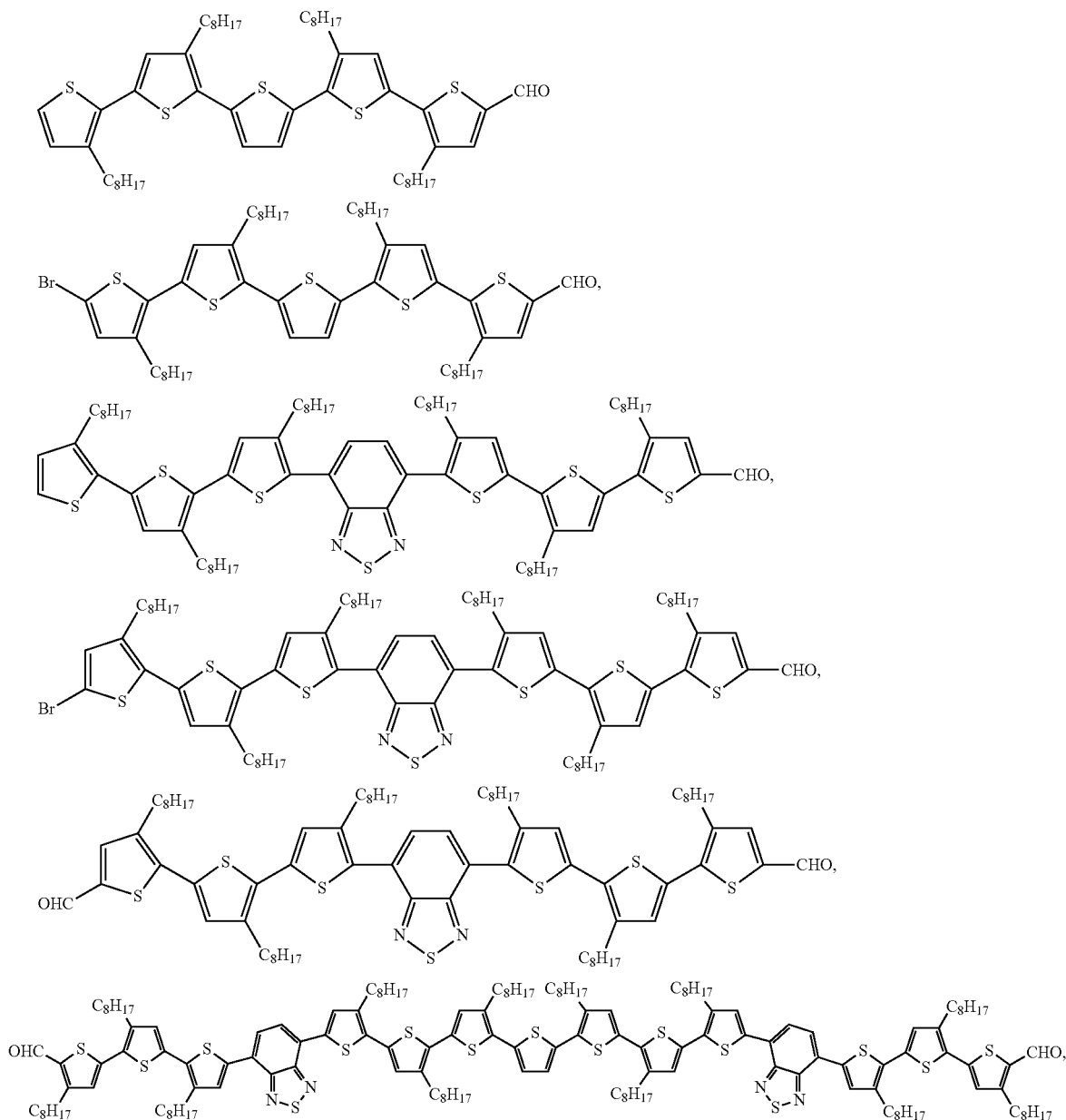

-continued
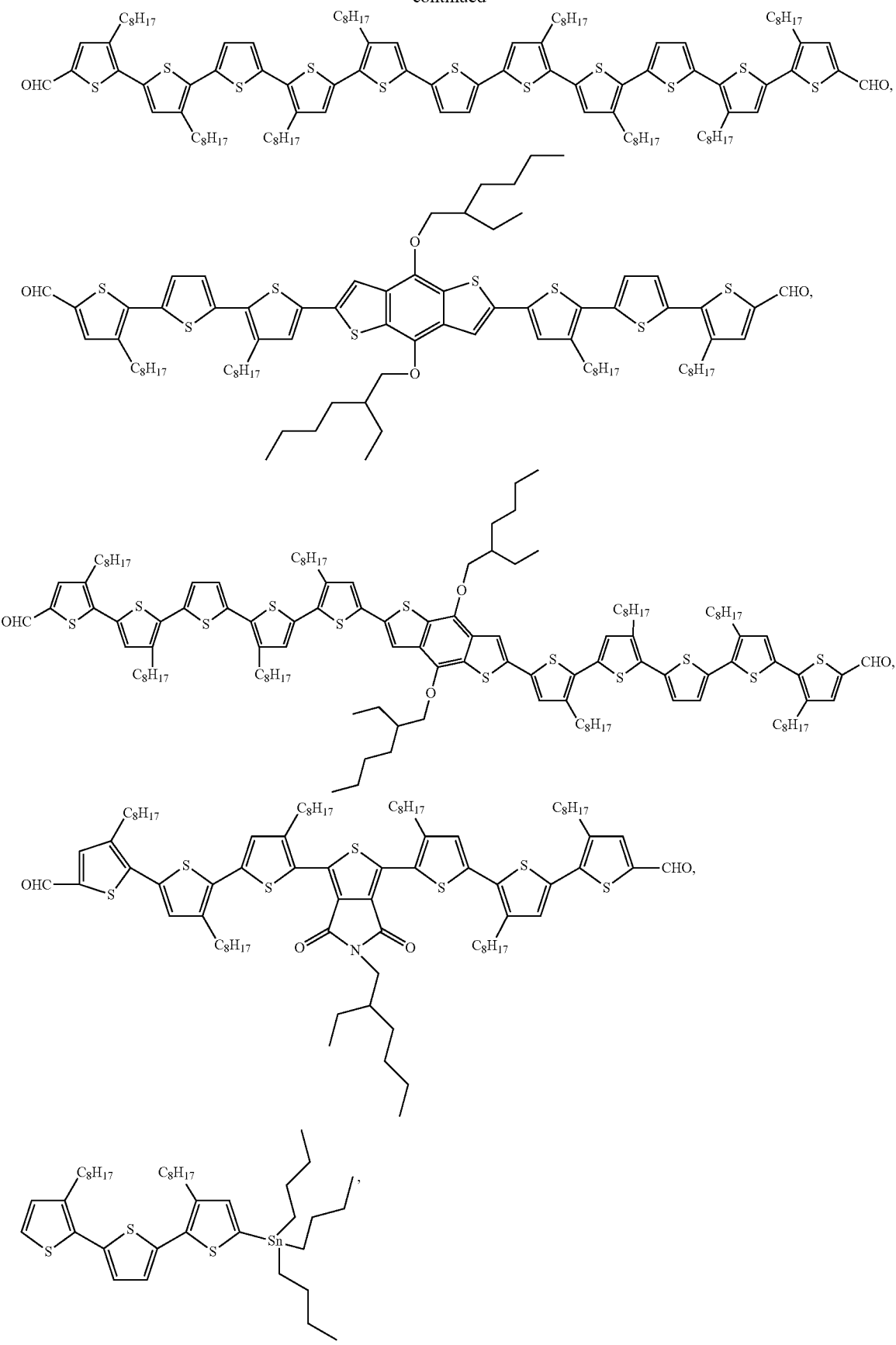

143                                              144
-continued
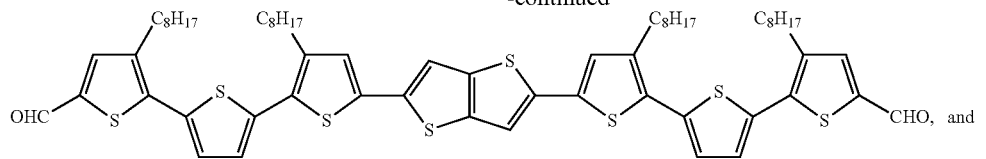
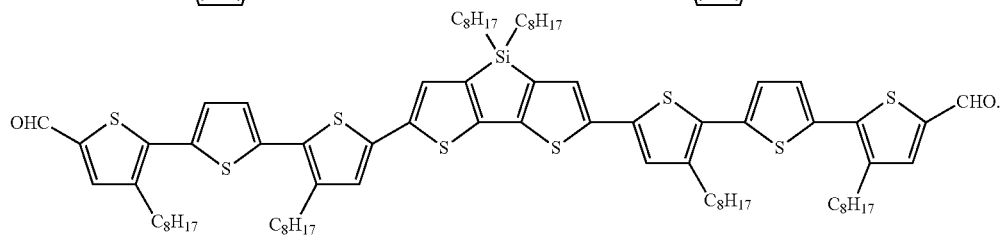
* * * * *